(12) United States Patent
Horowitz et al.

(10) Patent No.: US 8,131,480 B2
(45) Date of Patent: Mar. 6, 2012

(54) CONSTRUCTION OF DIVERSE SYNTHETIC PEPTIDE AND POLYPEPTIDE LIBRARIES

(75) Inventors: Lawrence Horowitz, Atherton, CA (US); Ramesh Bhatt, Belmont, CA (US); Aaron L. Kurtzman, San Carlos, CA (US)

(73) Assignee: Sea Lane Biotechnologies LLC, Atherton, CA (US)

( * ) Notice: Subject to any disclaimer, the term of this patent is extended or adjusted under 35 U.S.C. 154(b) by 1041 days.

(21) Appl. No.: 11/864,525

(22) Filed: Sep. 28, 2007

(65) Prior Publication Data

US 2009/0082213 A1    Mar. 26, 2009

Related U.S. Application Data

(60) Provisional application No. 60/849,035, filed on Oct. 2, 2006.

(51) Int. Cl.
*G01N 7/00*    (2006.01)
(52) U.S. Cl. ............... 702/19; 702/20; 703/11; 703/12; 707/700; 424/184.1; 536/24.1
(58) Field of Classification Search ........................ None
See application file for complete search history.

(56) References Cited

FOREIGN PATENT DOCUMENTS

| WO | WO 02/084277 A1 | 10/2002 |
|---|---|---|
| WO | WO 2005/098039 A2 | 10/2005 |
| WO | WO 2006/014498 A2 | 2/2006 |

OTHER PUBLICATIONS

Yu et al. Bioinformatics (Jul. 2005) vol. 21, Suppl 1, pp. i495-i501.*

* cited by examiner

*Primary Examiner* — Mary Zeman
(74) *Attorney, Agent, or Firm* — Arnold & Porter LLP; Ginger R. Dreger

(57) ABSTRACT

The present invention concerns the design and construction of diverse peptide and polypeptide libraries. In particular, the invention concerns methods of analytical database design for creating datasets using multiple relevant parameters as filters, and methods for generating sequence diversity by directed multisyntheses oligonucleotide synthesis. The present methods enable the reduction of large complex annotated databases to simpler datasets of related sequences, based upon relevant single or multiple key parameters that can be individually directly defined. The methods further enable the creation of diverse libraries based on this approach, using multisynthetic collections of discrete and degenerate oligonucleotides to capture the diverse collection of sequences, or portions thereof.

18 Claims, 40 Drawing Sheets
(34 of 40 Drawing Sheet(s) Filed in Color)

General Human antibody library steps

- Analyze Kabat CDR positional frequencies with unique filters for
  - Heavy chains
    - Light chain pairs. Ex. Kappa or lambda
    - CDR size matched. Ex. CDR1 = 6 or CDR2 = 13
    - CDR3 subfamily filtered. Ex. $V_H1$ vs. $V_H3$
  - Light chains
    - All CDR size matched. Ex. Select sequence entries only containing CDR1 = 7, CDR2=10, and CDR3 = 8 amino acids
    - Subfamily filtered. Ex. K1 or K3
- Positional analysis – determine positional frequency to generate CDR diversity sets
  - Set lower bounds for % usage of individual amino acids
  - Set lower bounds for sum % usage of most commonly used amino acids
  - Lower bounds can be defined by single or multiple CDR or even by individual positions

- Generate diversity sets
  - Use individually synthesized oligos to capture entire combinatorial positional diversity sets
  - Can use degenerate synthesis
  - Can include side products not found in diversity sets, with or without additional rulesets
- Select most frequently used frameworks in database for scaffold
  - $V_H1\ V_H3$
  - $V_K1\ V_K3$
  - $V_\lambda1\ V_\lambda2\ V_\lambda3$
- Clone diversity onto germline frameworks
- Additional filters possible might include
  - Antigen types such as secreted proteins, pathogenic targets, haptens, autoimmune sources, etc...
- Heavy chain isotypes such as IgG, IgM etc.

FIG. 1

Frequency analysis V$_K$1 CDR1, 2, and 3

* Absolute usage by position

| Threshold percent usage | 0 | 30 | 31 | 32 | 33 | 34 | 35 | 36 | 46 | 47 | 48 |
|---|---|---|---|---|---|---|---|---|---|---|---|
| # sequences | | 383 | 383 | 383 | 383 | 383 | 383 | 383 | 383 | 383 | 383 |
| | | | | | | | | | N | | L |
| A | | 3% | 1% | 2% | 0% | 43% | 0% | 0% | 0% | 0% | 0% |
| C | | 0% | 0% | 1% | 0% | 0% | 0% | 0% | 0% | 0% | 0% |
| D | | 4% | 2% | 8% | 0% | 0% | 0% | 0% | 0% | 0% | 0% |
| E | | 0% | 0% | 0% | 0% | 0% | 0% | 0% | 0% | 0% | 0% |
| F | | 0% | 0% | 8% | 0% | 0% | 0% | 7% | 1% | 2% | 0% |
| G | | 8% | 2% | 0% | 0% | 7% | 0% | 0% | 0% | 0% | 0% |
| H | | 0% | 2% | 1% | 0% | 2% | 0% | 1% | 0% | 0% | 0% |
| I | | 2% | 3% | 0% | 2% | 0% | 0% | 0% | 1% | 0% | 0% |
| K | | 2% | 3% | 0% | 3% | 0% | 0% | 0% | 0% | 0% | 95% |
| L | | 1% | 0% | 0% | 95% | 0% | 0% | 1% | 82% | 97% | 2% |
| M | | 0% | 0% | 0% | 1% | 0% | 0% | 0% | 0% | 0% | 2% |
| N | | 8% | 34% | 4% | 0% | 42% | 0% | 0% | 0% | 0% | 0% |
| P | | 0% | 0% | 0% | 0% | 0% | 0% | 0% | 0% | 0% | 0% |
| Q | | 0% | 5% | 2% | 0% | 0% | 0% | 0% | 1% | 0% | 0% |
| R | | 12% | 39% | 6% | 0% | 2% | 0% | 0% | 6% | 0% | 0% |
| S | | 54% | 6% | 6% | 0% | 2% | 0% | 0% | 4% | 0% | 0% |
| T | | 3% | 0% | 0% | 0% | 2% | 0% | 0% | 1% | 0% | 0% |
| V | | 1% | 0% | 2% | 2% | 2% | 0% | 0% | 4% | 0% | 1% |
| W | | 0% | 0% | 17% | 0% | 0% | 0% | 0% | 0% | 0% | 0% |
| Y | | 2% | 1% | 52% | 0% | 0% | 100% | 92% | 0% | 0% | 0% |
| % reprensented Sum percent threshold | 80 | 100% | 100% | 100% | 100% | 100% | 100% | 100% | 100% | 100% | 100% |
| | | | | | CDR1 | | | | | | |

FIG. 2 (Part 1)

| | 49 | 50 | 51 | 52 | 53 | 54 | 55 | 89 | 90 | 91 | 92 | 93 | 94 | 95 | 96 |
|---|---|---|---|---|---|---|---|---|---|---|---|---|---|---|---|
| | 383 | 383 | 383 | 383 | 383 | 383 | 383 | 383 | 383 | 383 | 383 | 383 | 383 | 383 | 383 |
| | | | | | | | | Q | G | | | | | | |
| | 0% | 55% | 90% | 1% | 0% | 0% | 5% | 0% | 0% | 5% | 1% | 2% | 5% | 1% | 0% |
| | 0% | 0% | 0% | 0% | 0% | 1% | 0% | 0% | 0% | 0% | 0% | 0% | 0% | 0% | 1% |
| | 0% | 13% | 0% | 0% | 0% | 0% | 1% | 0% | 0% | 2% | 11% | 4% | 1% | 0% | 1% |
| | 0% | 1% | 0% | 0% | 0% | 1% | 22% | 0% | 1% | 0% | 1% | 1% | 0% | 0% | 0% |
| | 4% | 9% | 0% | 0% | 0% | 0% | 0% | 1% | 0% | 2% | 2% | 0% | 9% | 0% | 7% |
| | 0% | 0% | 1% | 0% | 1% | 0% | 6% | 2% | 2% | 1% | 1% | 2% | 1% | 0% | 1% |
| | 1% | 0% | 0% | 0% | 1% | 0% | 0% | 0% | 0% | 7% | 7% | 3% | 1% | 0% | 2% |
| | 0% | 10% | 0% | 0% | 4% | 0% | 1% | 10% | 4% | 0% | 1% | 2% | 2% | 0% | 5% |
| | 0% | 0% | 0% | 0% | 1% | 0% | 1% | 0% | 0% | 4% | 2% | 0% | 0% | 0% | 2% |
| | 0% | 0% | 0% | 0% | 16% | 93% | 61% | 86% | 92% | 2% | 28% | 16% | 10% | 5% | 26% |
| | 0% | 1% | 1% | 1% | 1% | 0% | 1% | 0% | 1% | 0% | 0% | 0% | 0% | 0% | 0% |
| | 7% | 3% | 0% | 0% | 2% | 3% | 0% | 0% | 0% | 26% | 0% | 1% | 2% | 84% | 4% |
| | 0% | 3% | 5% | 94% | 48% | 1% | 0% | 0% | 0% | 5% | 6% | 61% | 4% | 2% | 3% |
| | 0% | 1% | 2% | 2% | 27% | 2% | 0% | 0% | 0% | 4% | 1% | 7% | 23% | 1% | 14% |
| | 0% | 1% | 0% | 0% | 1% | 1% | 0% | 0% | 0% | 1% | 1% | 0% | 4% | 7% | 1% |
| | 88% | 0% | 0% | 0% | 0% | 1% | 0% | 0% | 0% | 0% | 0% | 0% | 1% | 0% | 0% |
| | 0% | 0% | 5% | 2% | 0% | 2% | 0% | 0% | 0% | 40% | 36% | 0% | 3% | 0% | 3% |
| | 0% | 1% | 2% | 0% | 0% | 1% | 0% | 0% | 0% | 0% | 0% | 0% | 1% | 0% | 13% |
| | 0% | 0% | 0% | 0% | 0% | 1% | 0% | 0% | 0% | 0% | 0% | 0% | 33% | 0% | 18% |
| | 100% | 100% | 100% | 100% | 100% | 100% | 100% | 100% | 100% | 100% | 100% | 100% | 100% | 100% | 100% |

FIG. 2 (Part 2)

V_L kappa I Threshold analysis: part one

* No individual amino acids reported are below 10% usage
* Note that at least one position in each CDRs the sum usage is below 75%
   —To accommodate greater coverage we can reduce threshold percent usage

| | | 30 | 31 | 32 | 33 | 34 | 35 | 36 | 46 | 47 | 48 | 49 | 50 |
|---|---|---|---|---|---|---|---|---|---|---|---|---|---|
| # sequences | | 383 | 383 | 383 | 383 | 383 | 383 | 383 | 383 | 383 | 383 | 383 | 383 |
| Threshold percent usage | 10 | | | | | | | | | | | | |
| A | | | | | | 43% | | | | | | | 55% |
| C | | | | | | | | | | | | | |
| D | | | | | | | | | | | | | 13% |
| E | | | | | | | | | | | | | |
| F | | | | | | | | | | | | | |
| G | | | | | | | | | | | | | |
| H | | | | | | | | | | | | | |
| I | | | | | | | | | | | L | | |
| K | | | | | | | | | | | | | 10% |
| L | | | | | 95% | | | | 82% | 97% | 95% | | |
| M | | | | | | | | | | | | | |
| N | | | | | 34% | | 42% | | N | | | | |
| P | | | | | | | | | | | | | |
| Q | | | | | | | | | | | | | |
| R | | 12% | | | | | | | | | | | |
| S | | 54% | 39% | | | | | | | | | | |
| T | | | | 17% | | | | | | | | | |
| V | | | | 52% | | | 100% | 92% | | | | | |
| W | | | | | | | | | | | | | |
| Y | | | | | | | | | | | | 88% | |
| % represented | | 66% | 73% | 69% | 95% | 85% | 100% | 92% | 82% | 97% | 95% | 88% | 78% |
| Acceptable? | 80 | no | no | no | | | | | | | | | no |
| Sum percent threshold | | | | | | | | | | | | | |
| | | | | CDR1 | | | | | | | CDR2 | | |

FIG. 3 (Part 1)

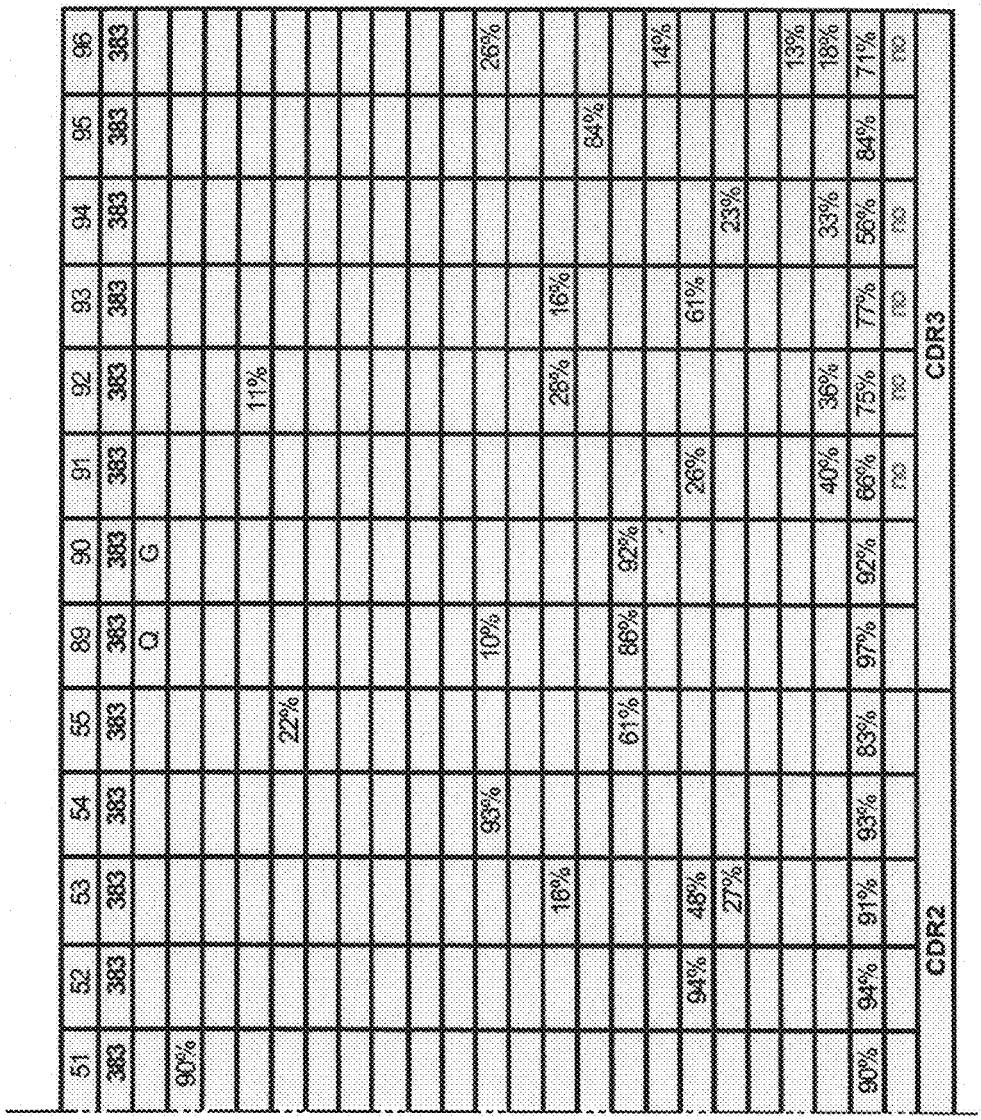
FIG. 3 (Part 2)

$V_L$ kappa Threshold analysis: part two

- Now no individual amino acids reported are below 5% usage
- As a result the sum usage for all positions is at least 75%
  – Which should accommodate greater coverage of diversity

| | | 30 | 31 | 32 | 33 | 34 | 35 | 36 | 46 | 47 | 48 | 49 | 50 |
|---|---|---|---|---|---|---|---|---|---|---|---|---|---|
| # sequences | | 383 | 383 | 383 | 383 | 383 | 383 | 383 | 383 | 383 | 383 | 383 | 383 |
| Threshold percent usage | 5 | | | | | | | | | | L | | |
| A | | | | | | 43% | | | | | | | 55% |
| C | | | | | | | | | | | | | |
| D | | | | 8% | | | | | | | | | 13% |
| E | | | | | | | | | | | | | |
| F | | | | 8% | | 7% | | 7% | | | | | |
| G | | 8% | | | | | | | | | | | 8% |
| H | | | | | | | | | | | | | |
| I | | | | | | | | | | | | | |
| K | | | | | 95% | | | | 82% | | 95% | | 10% |
| L | | | 34% | | | 42% | | | | | | | |
| M | | | | | | | | | | | | | |
| N | | 8% | | | | | | | 8% | | | | |
| P | | | | | | | | | | | | | |
| Q | | 12% | 5% | | | | | | | | | | |
| R | | 54% | 38% | 8% | | | | | | | | | |
| S | | | 8% | | | | 100% | 92% | | | | 7% | |
| T | | | | 17% | | | | | | | | | |
| V | | | | 52% | | | | | | | | | |
| W | | | | | | | | | | | | 88% | |
| Y | | | | | | | | | | | | 95% | |
| % represented | | 83% | 85% | 90% | 95% | 92% | 100% | 99% | 90% | 97% | 95% | 95% | 88% |
| Acceptable? | | | | | | | | | | | | | |
| | | | | | CDR1 | | | | | | CDR2 | | |
| Sum percent threshold | 75 | | | | | | | | | | | | |

FIG. 4 (Part 1)

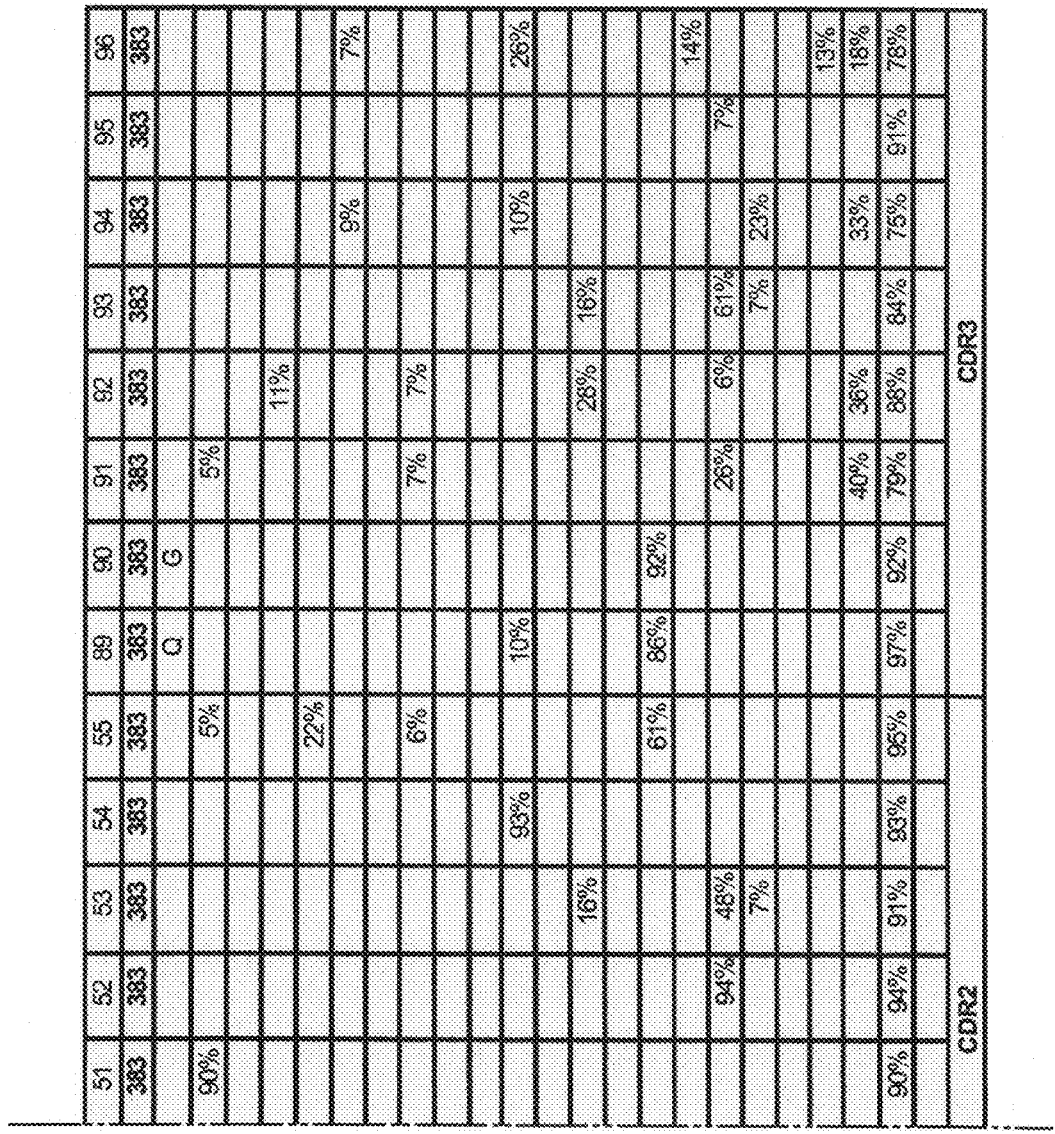
FIG. 4 (Part 2)

Synthesizing Light chain CDR1 diversity

- To cover diversity must make 128 combinatorial oligonucleotides to encode intended diversity
- Or 16 degenerate combinatorial oligonucleotides Note: bases do not need to be equimolar and can be tuned to bias amino acid usage to reflect frequencies found in our analysis and even include residues not included in the frequency tables Degenerate design

| | S | T | A | M | T | G | K | C | T | G | C | A | T | G | T | C | T | #Oligos |
|---|---|---|---|---|---|---|---|---|---|---|---|---|---|---|---|---|---|---|
| | A | R | G | T | W | T | C | G | A | T | C | 1 | 1 | 16 |
| | 2 | 2 | 2 | 2 | 2 | 1 | 2 | 1 | 1 | 1 | |
| K1_01 | S | A | M | T | G | C | T | G | C | A | T | G | T | C | T | | | |
| K1_02 | A | R | T | G | W | T | C | G | A | T | C | | | |
| K1_03 | S | G | M | T | G | C | T | G | C | A | T | G | T | C | T | | | |
| K1_04 | A | R | T | T | W | T | C | G | A | T | C | | | |
| K1_05 | S | G | A | T | G | C | T | G | C | A | T | G | T | C | T | | | |
| K1_06 | A | R | M | T | W | T | C | G | A | T | C | | | |
| K1_07 | S | G | M | T | T | C | T | G | C | A | T | G | T | C | T | | | |
| K1_08 | A | R | A | T | W | T | C | G | A | T | C | | | |
| K1_09 | S | G | M | T | G | C | T | G | C | A | T | G | T | C | T | | | |
| K1_10 | A | R | A | T | W | T | C | G | A | T | C | | | |
| K1_11 | S | G | M | T | G | C | T | A | C | T | G | T | C | T | | | |
| K1_12 | A | R | A | T | W | T | C | T | A | T | C | | | |
| K1_13 | S | G | M | T | G | C | T | A | C | T | G | T | C | T | | | |
| K1_14 | A | R | A | T | W | T | C | T | A | T | C | | | |
| K1_15 | S | G | M | T | G | C | T | A | C | T | G | T | C | T | | | |
| K1_16 | A | R | A | T | W | T | C | T | A | T | C | | | |

FIG. 5

V$_H$3 Heavy Chain synthetic library diversity length 10

- CDR3 contains 3.3×10⁵ total diversity
- Only 96 degenerate oligonucleotides are required
- Position 97 SWY (4% each) were omitted
- Position 100A G (6%) was omitted

| VH3 length 10 | 93 | 94 | 95 | 96 | 97 | 98 | 99 | 100 | 100A | 101 |
|---|---|---|---|---|---|---|---|---|---|---|
| # sequences | 68 | 68 | 68 | 68 | 68 | 68 | 67 | 68 | 68 | 68 |
| A | 91% | | | | | 9% | | 32% | | |
| C | | | | | | | | | | |
| D | | | 25% | 7% | 6% | 7% | 9% | | | 85% |
| E | | | 12% | | | | | | | |
| F | | | | | | | | | 32% | |
| G | | | 10% | 13% | 13% | 31% | 19% | 22% | | |
| H | | | | | | | 9% | | | |
| I | | | | | | | | | 3% | |
| K | | 22% | 6% | | 21% | | | | | |
| L | | | 21% | 6% | 6% | | | | 7% | |
| M | | | | | | | | | 38% | |
| N | | | | | | | | | | |
| P | | | | | 6% | | | | | |
| Q | | | | | 4% | | | | | |
| R | | 63% | | 31% | 4% | 6% | 6% | | | |
| S | | | | | | 12% | | 16% | | |
| T | | | | | | | | | | |
| V | | | 6% | 12% | 9% | | 36% | 12% | | |
| W | | | | | | | | | | |
| Y | | | | | | | | | | |
| % coverage | 91% | 85% | 79% | 75% | 69% | 76% | 79% | 82% | 81% | 85% |
| | | | | | CDR3 | | | | | |

| # degenerate codons | 1 | 2 | 2 | 2 | 3 | 2 | 1 | 2 | 1 | 1 |
|---|---|---|---|---|---|---|---|---|---|---|
| | | | | | oligos | | | | | |
| | | | | 96 | | | | | | |
| | | | | 3.3E+05 total CDR3 diversity | | | | | | |

FIG. 6

Synthesizing V_H 3 Heavy chain CDR3 length 10 diversity

| NAME | SEQUENCE |
|---|---|
| H3_3_10_001a | ACCGCAGTTTACTATTGCGCACGTVTGSKTAAGKMTBRTGSTWTKGATTACTGGGTCAGGGCAC |
| H3_3_10_002a | ACCGCAGTTTACTATTGCGCACGTVTGSKTAAGKMTBRTGSTWTKGATTACTGGGTCAGGGCAC |
| H3_3_10_003a | ACCGCAGTTTACTATTGCGCACGTGRWSKTAAGKMTBRTGSTWTKGATTACTGGGTCAGGGCAC |
| H3_3_10_004a | ACCGCAGTTTACTATTGCGCAAAGGRWSKTAAGKMTBRTGSTWTKGATTACTGGGTCAGGGCAC |
| H3_3_10_005a | ACCGCAGTTTACTATTGCGCACGTVTGGMTAAGKMTBRTGSTWTKGATTACTGGGTCAGGGCAC |
| H3_3_10_006a | ACCGCAGTTTACTATTGCGCACGTVTGSKTAAGKMTBRTGSTWTKGATTACTGGGTCAGGGCAC |
| H3_3_10_007a | ACCGCAGTTTACTATTGCGCACGTVTGGMTAAGKMTBRTGSTWTKGATTACTGGGTCAGGGCAC |
| H3_3_10_008a | ACCGCAGTTTACTATTGCGCAAAGGRWGMTAAGKMTBRTGSTWTKGATTACTGGGTCAGGGCAC |
| H3_3_10_009a | ACCGCAGTTTACTATTGCGCACGTVTGSKTGDTKMTBRTGSTWTKGATTACTGGGTCAGGGCAC |
| H3_3_10_010a | ACCGCAGTTTACTATTGCGCACGTVTGSKTGDTKMTBRTGSTWTKGATTACTGGGTCAGGGCAC |
| H3_3_10_011a | ACCGCAGTTTACTATTGCGCACGTGRWSKTGDTKMTBRTGSTWTKGATTACTGGGTCAGGGCAC |
| H3_3_10_012a | ACCGCAGTTTACTATTGCGCAAAGGRWSKTGDTKMTBRTGSTWTKGATTACTGGGTCAGGGCAC |
| H3_3_10_013a | ACCGCAGTTTACTATTGCGCACGTVTGGMTGDTKMTBRTGSTWTKGATTACTGGGTCAGGGCAC |
| H3_3_10_014a | ACCGCAGTTTACTATTGCGCACGTVTGGMTGDTKMTBRTGSTWTKGATTACTGGGTCAGGGCAC |
| H3_3_10_015a | ACCGCAGTTTACTATTGCGCACGTGRWGMTGDTKMTBRTGSTWTKGATTACTGGGTCAGGGCAC |
| H3_3_10_016a | ACCGCAGTTTACTATTGCGCAAAGGRWGMTGDTKMTBRTGSTWTKGATTACTGGGTCAGGGCAC |
| H3_3_10_017a | ACCGCAGTTTACTATTGCGCACGTVTGSKTCNTKMTBRTGSTWTKGATTACTGGGTCAGGGCAC |
| H3_3_10_018a | ACCGCAGTTTACTATTGCGCACGTVTGSKTCNTKMTBRTGSTWTKGATTACTGGGTCAGGGCAC |
| H3_3_10_019a | ACCGCAGTTTACTATTGCGCACGTGRWSKTCNTKMTBRTGSTWTKGATTACTGGGTCAGGGCAC |
| H3_3_10_020a | ACCGCAGTTTACTATTGCGCAAAGGRWSKTCNTKMTBRTGSTWTKGATTACTGGGTCAGGGCAC |
| H3_3_10_021a | ACCGCAGTTTACTATTGCGCACGTVTGGMTCNTKMTBRTGSTWTKGATTACTGGGTCAGGGCAC |
| H3_3_10_022a | ACCGCAGTTTACTATTGCGCACGTVTGGMTCNTKMTBRTGSTWTKGATTACTGGGTCAGGGCAC |
| H3_3_10_023a | ACCGCAGTTTACTATTGCGCACGTGRNGMTCNTKMTBRTGSTWTKGATTACTGGGTCAGGGCAC |
| H3_3_10_024a | ACCGCAGTTTACTATTGCGCAAAGGRWGMTCNTKMTBRTGSTWTKGATTACTGGGTCAGGGCAC |
| H3_3_10_025a | ACCGCAGTTTACTATTGCGCACGTVTGSKTAAGSGTBRTGSTWTKGATTACTGGGTCAGGGCAC |
| H3_3_10_026a | ACCGCAGTTTACTATTGCGCACGTVTGSKTAAGSGTBRTGSTWTKGATTACTGGGTCAGGGCAC |
| H3_3_10_027a | ACCGCAGTTTACTAGTGCGCACGTGRWSKTAAGSGTBRTGSTWTKGATTACTGGGTCAGGGCAC |
| H3_3_10_028a | ACCGCAGTTTACTATTGCGCAAAGGRWSKTAAGSGTBRTGSTWTKGATTACTGGGTCAGGGCAC |

FIG. 7 (PART 1)

FIG. 7 (PART 2)

| | |
|---|---|
| H3_3_10_059a | ACCGCAGTTTACTATTGCGCACGTGRWSKTGDTKMTBRTTMTWTKGATTACTGGGTCAGGGCAC |
| H3_3_10_060a | ACCGCAGTTTACTATTGCGCAAAGGRWSKTGDTKMTBRTTMTWTKGATTACTGGGTCAGGGCAC |
| H3_3_10_061a | ACCGCAGTTTACTATTGCGCACGTVTGGMTGDTKMTBRTTMTWTKGATTACTGGGTCAGGGCAC |
| H3_3_10_062a | ACCGCAGTTTACTATTGCGCAAAGVTGGMTGDTKMTBRTTMTWTKGATTACTGGGTCAGGGCAC |
| H3_3_10_063a | ACCGCAGTTTACTATTGCGCACGTGRWGMTGDTKMTBRTTMTWTKGATTACTGGGTCAGGGCAC |
| H3_3_10_064a | ACCGCAGTTTACTATTGCGCAAAGGRWGMTGDTKMTBRTTMTWTKGATTACTGGGTCAGGGCAC |
| H3_3_10_065a | ACCGCAGTTTACTATTGCGCACGTVTGSKTCNTKMTBRTTMTWTKGATTACTGGGTCAGGGCAC |
| H3_3_10_066a | ACCGCAGTTTACTATTGCGCAAAGVTGSKTCNTKMTBRTTMTWTKGATTACTGGGTCAGGGCAC |
| H3_3_10_067a | ACCGCAGTTTACTATTGCGCACGTGRWSKTCNTKMTBRTTMTWTKGATTACTGGGTCAGGGCAC |
| H3_3_10_068a | ACCGCAGTTTACTATTGCGCAAAGGRWSKTCNTKMTBRTTMTWTKGATTACTGGGTCAGGGCAC |
| H3_3_10_069a | ACCGCAGTTTACTATTGCGCACGTVTGGMTCNTKMTBRTTMTWTKGATTACTGGGTCAGGGCAC |
| H3_3_10_070a | ACCGCAGTTTACTATTGCGCAAAGVTGGMTCNTKMTBRTTMTWTKGATTACTGGGTCAGGGCAC |
| H3_3_10_071a | ACCGCAGTTTACTATTGCGCACGTGRWGMTCNTKMTBRTTMTWTKGATTACTGGGTCAGGGCAC |
| H3_3_10_072a | ACCGCAGTTTACTATTGCGCAAAGGRWGMTCNTKMTBRTTMTWTKGATTACTGGGTCAGGGCAC |
| H3_3_10_073a | ACCGCAGTTTACTATTGCGCACGTVTGSKTAAGSGTBRTTMTWTKGATTACTGGGTCAGGGCAC |
| H3_3_10_074a | ACCGCAGTTTACTATTGCGCAAAGVTGSKTAAGSGTBRTTMTWTKGATTACTGGGTCAGGGCAC |
| H3_3_10_075a | ACCGCAGTTTACTATTGCGCACGTGRWSKTAAGSGTBRTTMTWTKGATTACTGGGTCAGGGCAC |
| H3_3_10_076a | ACCGCAGTTTACTATTGCGCAAAGGRWSKTAAGSGTBRTTMTWTKGATTACTGGGTCAGGGCAC |
| H3_3_10_077a | ACCGCAGTTTACTATTGCGCACGTVTGGMTAAGSGTBRTTMTWTKGATTACTGGGTCAGGGCAC |
| H3_3_10_078a | ACCGCAGTTTACTATTGCGCAAAGVTGGMTAAGSGTBRTTMTWTKGATTACTGGGTCAGGGCAC |
| H3_3_10_079a | ACCGCAGTTTACTATTGCGCACGTGRWGMTAAGSGTBRTTMTWTKGATTACTGGGTCAGGGCAC |
| H3_3_10_080a | ACCGCAGTTTACTATTGCGCAAAGGRWGMTAAGSGTBRTTMTWTKGATTACTGGGTCAGGGCAC |
| H3_3_10_081a | ACCGCAGTTTACTATTGCGCACGTVTGSKTGDTSGTBRTTMTWTKGATTACTGGGTCAGGGCAC |
| H3_3_10_082a | ACCGCAGTTTACTATTGCGCAAAGVTGSKTGDTSGTBRTTMTWTKGATTACTGGGTCAGGGCAC |
| H3_3_10_083a | ACCGCAGTTTACTATTGCGCACGTGRWSKTGDTSGTBRTTMTWTKGATTACTGGGTCAGGGCAC |
| H3_3_10_084a | ACCGCAGTTTACTATTGCGCAAAGGRWSKTGDTSGTBRTTMTWTKGATTACTGGGTCAGGGCAC |
| H3_3_10_085a | ACCGCAGTTTACTATTGCGCACGTVTGGMTGDTSGTBRTTMTWTKGATTACTGGGTCAGGGCAC |
| H3_3_10_086a | ACCGCAGTTTACTATTGCGCAAAGVTGGMTGDTSGTBRTTMTWTKGATTACTGGGTCAGGGCAC |
| H3_3_10_087a | ACCGCAGTTTACTATTGCGCACGTGRWGMTGDTSGTBRTTMTWTKGATTACTGGGTCAGGGCAC |
| H3_3_10_088a | ACCGCAGTTTACTATTGCGCAAAGGRWGMTGDTSGTBRTTMTWTKGATTACTGGGTCAGGGCAC |

FIG. 7 (PART 3)

| | |
|---|---|
| H3_3_10_089a | ACCGCAGTTTACTATTGCGCACGTVTIGSKTCNTSGTBRTTMTWTKGATTACTGGGGTCAGGGCAC |
| H3_3_10_090a | ACCGCAGTTTACTATTGCGCAAAGVTIGSKTCNTSGRBRTTMTWTKGATTACTGGGGTCAGGGCAC |
| H3_3_10_091a | ACCGCAGTTTACTATTGCGCACGTGRWSKTCNTSGTBRTTMTWTKGATTACTGGGGTCAGGGCAC |
| H3_3_10_092a | ACCGCAGTTTACTATTGCGCAAAGGRWSKTCNTSGTBRTTMTWTKGATTACTGGGGTCAGGGCAC |
| H3_3_10_093a | ACCGCAGTTTACTATTGCGCACGTVTGGMTCNTSGTBRTTMTWTKGATTACTGGGGTCAGGGCAC |
| H3_3_10_094a | ACCGCAGTTTACTATTGCGCAAAGVTGGMTCNTSGTBRTTMTWTKGATTACTGGGGTCAGGGCAC |
| H3_3_10_095a | ACCGCAGTTTACTATTGCGCACGTGRWGMTCNTSGTBRTTMTWTKGATTACTGGGGTCAGGGCAC |
| H3_3_10_096a | ACCGCAGTTTACTATTGCGCAAAGGRWGMTCNTSGTBRTTMTWTKGATTACTGGGGTCAGGGCAC |

FIG. 7 (PART 4)

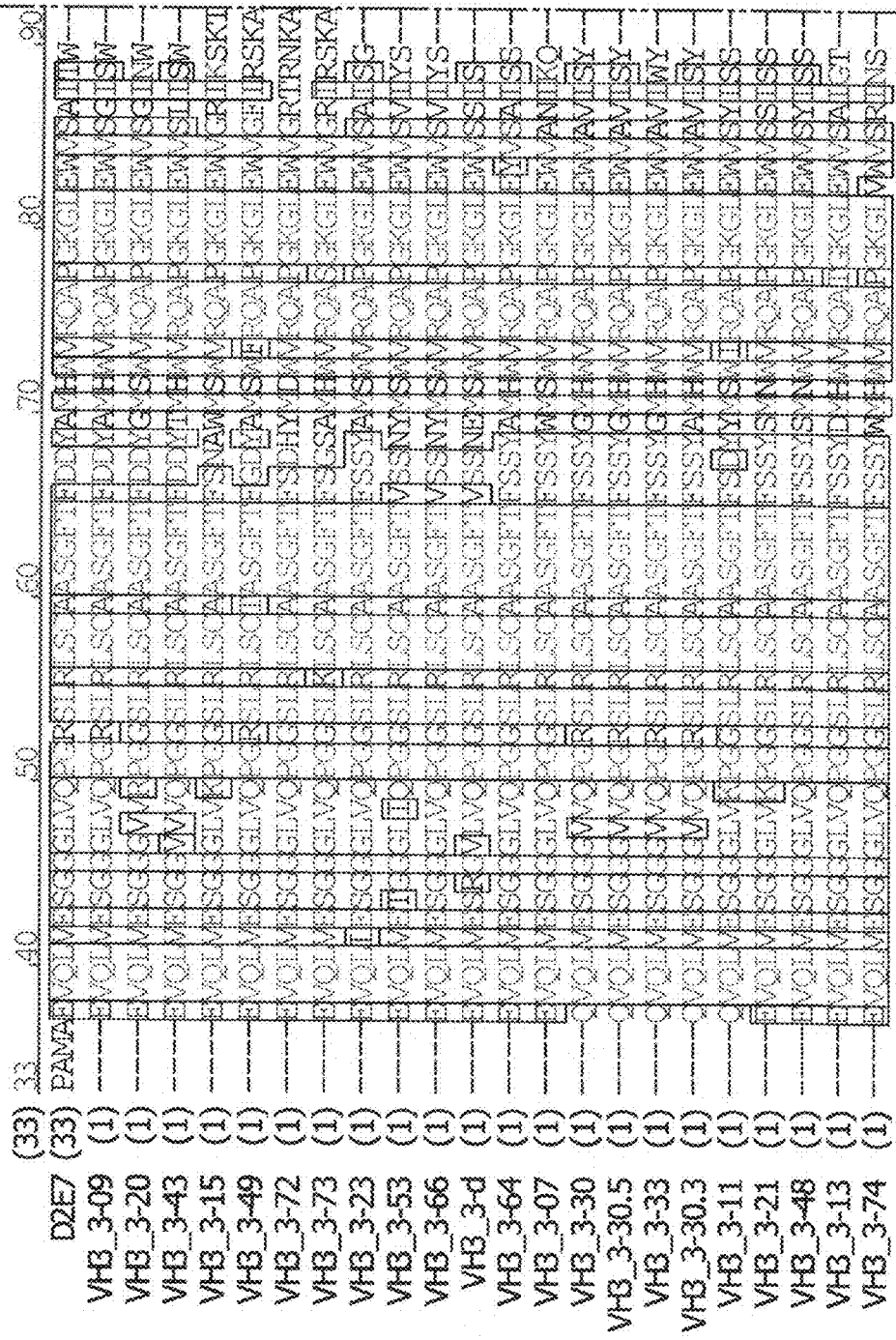
FIG. 8 (PART 1)

FIG. 8 (PART 2)

FIG. 10 (PART 1)

FIG. 10 (PART 2)

FIG. 12 (PART 1)

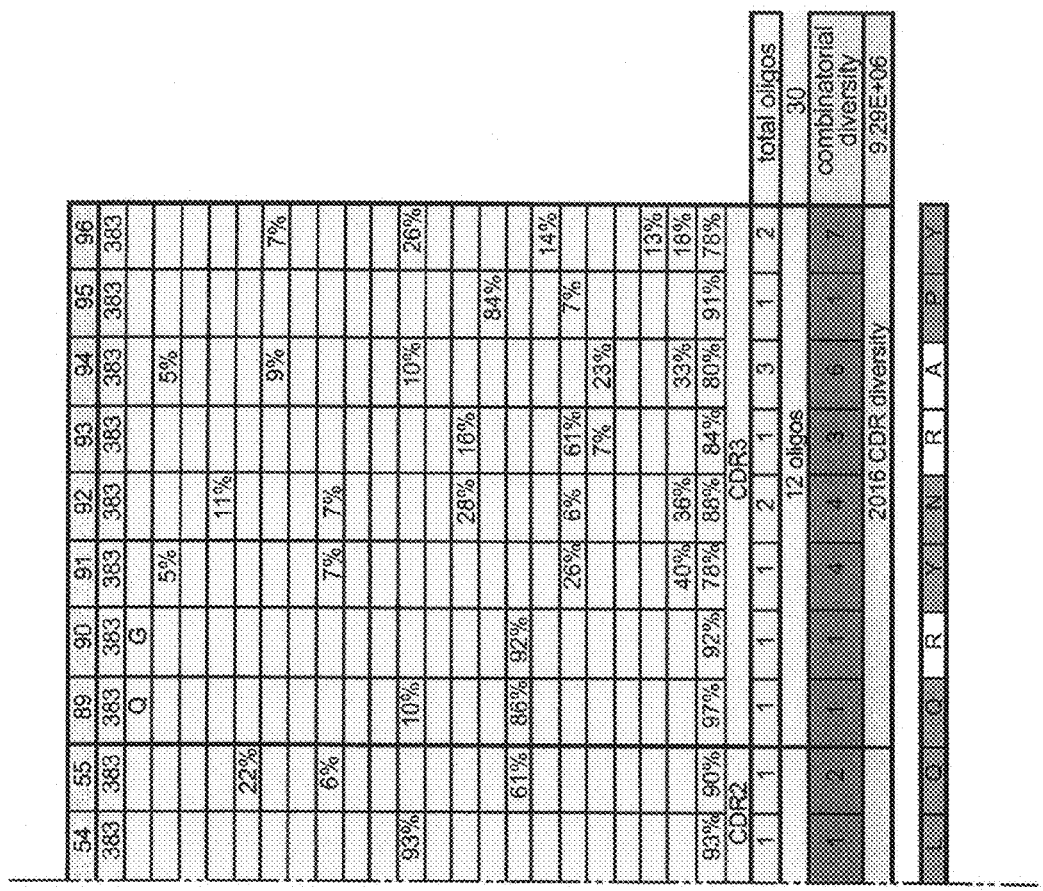
FIG. 12 (PART 2)

Frequency analysis V$_H$3 CDR1 and CDR2

*Absolute usage by position

| | | 30 | 31 | 32 | 33 | 34 | 35 | 47 | 48 | 49 | 50 |
|---|---|---|---|---|---|---|---|---|---|---|---|
| # sequences | | 181 | 181 | 181 | 181 | 181 | 181 | 181 | 181 | 181 | 181 |
| Threshold percent usage | 0 | | | | | | | | | | |
| A | | 0% | 1% | 0% | 44% | 0% | 0% | 0% | 1% | 40% | 12% |
| C | | 0% | 1% | 2% | 1% | 0% | 0% | 5% | 0% | 0% | 0% |
| D | | 4% | 11% | 1% | 3% | 0% | 3% | 0% | 0% | 0% | 1% |
| E | | 1% | 0% | 0% | 11% | 0% | 1% | 0% | 0% | 1% | 0% |
| F | | 0% | 1% | 12% | 0% | 0% | 1% | 0% | 0% | 0% | 4% |
| G | | 1% | 2% | 0% | 18% | 0% | 1% | 0% | 0% | 1% | 13% |
| H | | 0% | 0% | 4% | 0% | 0% | 34% | 0% | 0% | 0% | 2% |
| I | | 1% | 0% | 0% | 0% | 6% | 0% | 0% | 1% | 0% | 2% |
| K | | 4% | 1% | 0% | 1% | 2% | 0% | 0% | 1% | 0% | 0% |
| L | | 0% | 0% | 1% | 0% | 89% | 0% | 0% | 1% | 0% | 11% |
| M | | 0% | 0% | 0% | 0% | 0% | 0% | 0% | 0% | 0% | 1% |
| N | | 2% | 24% | 1% | 0% | 0% | 23% | 0% | 0% | 0% | 3% |
| P | | 0% | 0% | 0% | 0% | 0% | 0% | 0% | 0% | 0% | 0% |
| Q | | 0% | 0% | 0% | 0% | 0% | 0% | 0% | 0% | 0% | 0% |
| R | | 10% | 2% | 0% | 0% | 1% | 0% | 1% | 0% | 1% | 1% |
| S | | 76% | 40% | 3% | 11% | 1% | 34% | 0% | 0% | 58% | 16% |
| T | | 1% | 17% | 2% | 1% | 3% | 3% | 0% | 0% | 0% | 1% |
| V | | 0% | 1% | 1% | 2% | 0% | 0% | 0% | 98% | 0% | 18% |
| W | | 0% | 0% | 0% | 4% | 0% | 0% | 94% | 0% | 0% | 2% |
| Y | | 0% | 0% | 76% | 4% | 0% | 2% | 0% | 0% | 0% | 14% |
| % represented | | 100% | 100% | 100% | 100% | 100% | 100% | 100% | 100% | 100% | 100% |
| Sum percent threshold | | | | | | CDR1 | | | | | |

FIG. 13 (PART 1)

| | 51 | 52 | 52A | 53 | 54 | 55 | 56 | 57 | 58 |
|---|---|---|---|---|---|---|---|---|---|
| | 0% | 0% | 4% | 1% | 1% | 5% | 2% | 0% | 0% |
| | 0% | 0% | 0% | 0% | 0% | 0% | 0% | 0% | 0% |
| | 0% | 0% | 6% | 32% | 0% | 9% | 1% | 0% | 1% |
| | 0% | 0% | 2% | 0% | 1% | 3% | 2% | 3% | 1% |
| | 2% | 6% | 2% | 11% | 78% | 0% | 2% | 0% | 4% |
| | 0% | 0% | 19% | 1% | 0% | 31% | 0% | 0% | 4% |
| | 0% | 0% | 1% | 0% | 0% | 0% | 0% | 0% | 4% |
| | 88% | 0% | 1% | 0% | 0% | 1% | 4% | 23% | 0% |
| | 1% | 7% | 2% | 1% | 0% | 0% | 2% | 28% | 1% |
| | 3% | 1% | 0% | 0% | 0% | 0% | 2% | 4% | 0% |
| | 2% | 0% | 6% | 14% | 1% | 3% | 0% | 0% | 0% |
| | 0% | 7% | 1% | 0% | 0% | 0% | 28% | 0% | 5% |
| | 2% | 0% | 4% | 3% | 0% | 7% | 0% | 0% | 0% |
| | 1% | 5% | 4% | 36% | 20% | 34% | 1% | 1% | 2% |
| | 2% | 61% | 20% | 2% | 0% | 5% | 3% | 2% | 9% |
| | 1% | 3% | 2% | 0% | 0% | 1% | 22% | 1% | 1% |
| | 0% | 1% | 0% | 0% | 0% | 1% | 22% | 37% | 0% |
| | 0% | 3% | 6% | 0% | 0% | 1% | 1% | 1% | 2% |
| | 0% | 7% | 23% | 0% | 0% | 1% | 10% | 0% | 66% |
| | 100% | 100% | 100% | 100% | 100% | 100% | 100% | 100% | 100% |

CDR2

FIG. 13 (PART 2)

CDR1 & CDR2 Threshold analysis: part one

- No individual amino acids reported are below 10% usage
- In CDR2 the sum amino acid usage at positions 52, 52A, 55, and 58 is less than 75%
- To accommodate greater coverage we can reduce threshold percent usage

| | Threshold percent usage | 30 | 31 | 32 | 33 | 34 | 35 | 47 | 48 | 49 | 50 |
|---|---|---|---|---|---|---|---|---|---|---|---|
| # sequences | 10 | 181 | 181 | 181 | 181 | 181 | 181 | 181 | 181 | 181 | 181 |
| A | | | | | 44% | | | | | 40% | 12% |
| C | | | | | | | | | | | |
| D | | | 11% | | | | | | | | |
| E | | | | | 11% | | | | | | |
| F | | | | 12% | | | | | | | 13% |
| G | | | | | 18% | | | | | | |
| H | | | | | | | 34% | | | | |
| I | | | | | | | | | | | |
| K | | | | | | | | | | | 11% |
| L | | | | | | 89% | | | | | |
| M | | | | | | | | | | | |
| N | | | 24% | | | | 23% | | | | |
| P | | | | | | | | | | | |
| Q | | | | | | | | | | | |
| R | | 10% | | | | | | | | | |
| S | | 76% | 40% | | 11% | | 3% | | | 58% | 18% |
| T | | | 17% | | | | | | | | |
| V | | | | | | | | 94% | 98% | | |
| W | | | | 78% | | | | | | | |
| Y | | | | | | | | | | | 14% |
| % represented | | 86% | 93% | 88% | 85% | 89% | 91% | 94% | 98% | 98% | 85% |
| Acceptable? | | | | | | | | | | | |
| Sum percent threshold | 75 | | | | CDR1 | | | | | | |

FIG. 14 (PART 1)

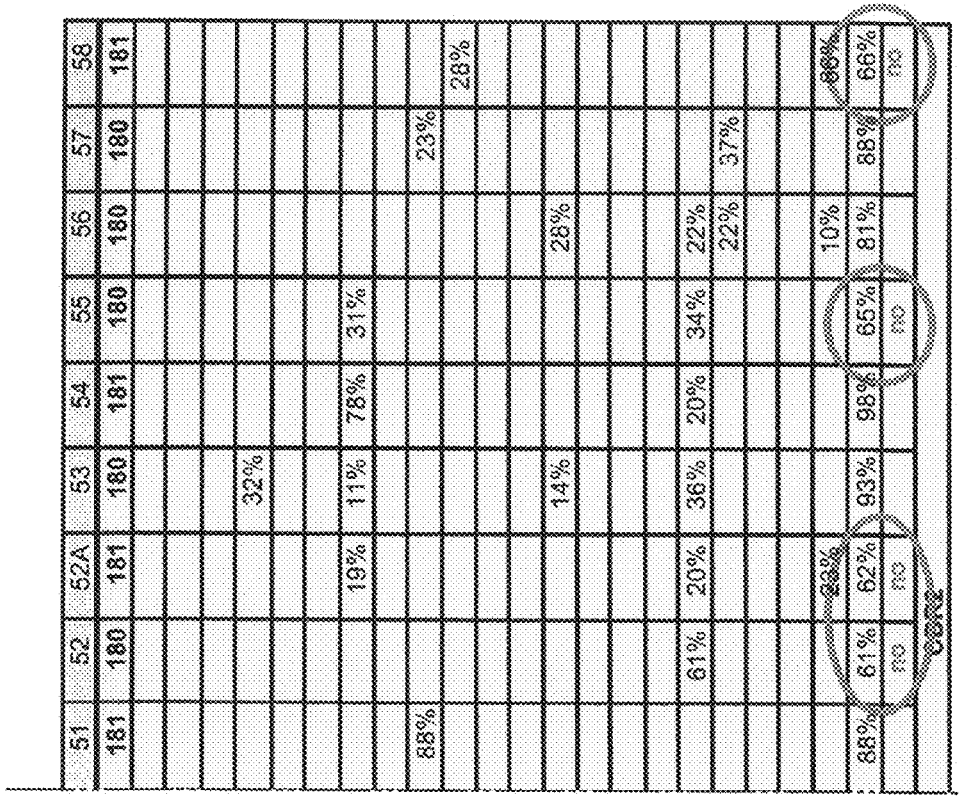
FIG. 14 (PART 2)

CDR1 & CDR2 Threshold analysis: part two

- Change percent threshold to 5% so that no individuals reported are below 5% usage
- Now the sum amino acid usage of all positions exceeds 75%

| | | 30 | 31 | 32 | 33 | 34 | 35 | 47 | 48 | 49 | 50 | 51 |
|---|---|---|---|---|---|---|---|---|---|---|---|---|
| # sequences | | 181 | 181 | 181 | 181 | 181 | 181 | 181 | 181 | 181 | 181 | 181 |
| Threshold percent usage | 5 | | | | | | | | | | | |
| A | | | | | 44% | | | | | 40% | 12% | |
| C | | | | | | | | | | | | |
| D | | | 11% | | | | | | | | | |
| E | | | | | | | | | | | | |
| F | | | | 12% | 11% | | | | | | | |
| G | | | | | 18% | | | | | | 13% | |
| H | | | | | | 6% | 34% | | | | | 88% |
| I | | | | | | | | | | | | |
| K | | | | | | | | | | | | |
| L | | | | | | 89% | | | | | | |
| M | | | | | | | | | | | | |
| N | | | 24% | | | | 23% | | | | | |
| P | | | | | | | | | | | | |
| Q | | | | | | | | | | | | |
| R | | 10% | | | | | | | | | | |
| S | | 76% | 40% | | 11% | | 34% | | | 58% | 16% | |
| T | | | 17% | | | | | | | | | |
| V | | | | 76% | | | | | 98% | | 18% | |
| W | | | | | | | | 94% | | | | |
| Y | | | | | | | | | | | 14% | |
| % represented | | 86% | 93% | 88% | 85% | 94% | 91% | 99% | 98% | 98% | 85% | 88% |
| Acceptable? | | | | | | | CDR1 | | | | | |
| Sum percent threshold | 75 | | | | | | | | | | | |

*Decreased threshold improves coverage*

FIG. 15 (PART 1)

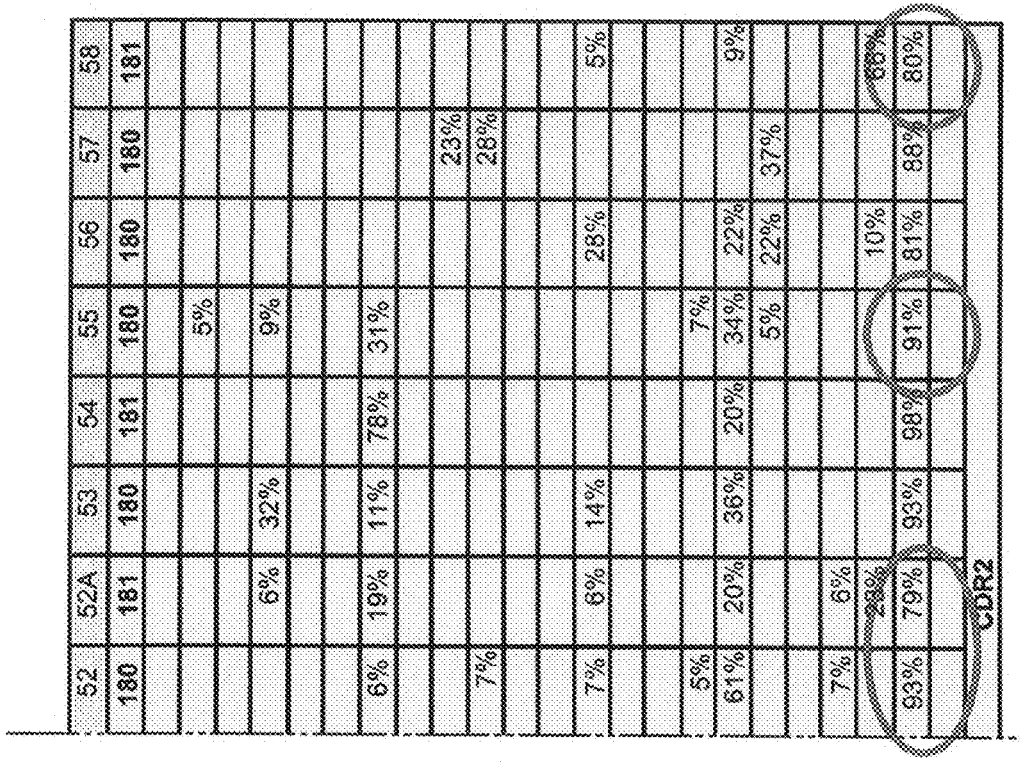
FIG. 15 (PART 2)

V$_H$3 Heavy Chain synthetic library diversity

- CDR1 & CDR2 combined contain 1.5x10$^8$ total diversity representing >80% positional coverage
- 28 degenerate oligonucleotides are required

| VH3 kappa paired | 30 | 31 | 32 | 33 | 34 | 35 | 47 | 48 | 49 | 50 | 51 | 52 |
|---|---|---|---|---|---|---|---|---|---|---|---|---|
| # sequences | 181 | 181 | 181 | 181 | 181 | 181 | 181 | 181 | 181 | 181 | 181 | 180 |
| A | | | | 44% | | | | | 40% | 12% | | |
| C | | | | | | | | | | | | |
| D | | | | | | | | | | | | |
| E | | | | 11% | | | | | | | | |
| F | | | 12% | | | | | | | | | |
| G | | | | 16% | | | | | | 13% | | |
| H | | | | | | 34% | | | | | | 7% |
| I | | | | | | | | | | | 88% | |
| K | | | | | | | | | | | | |
| L | | | | | 89% | | | | | 11% | | |
| M | | 24% | | | | | | | | | | |
| N | | | | | | 23% | | | | | | 7% |
| P | | | | | | | | | | | | |
| Q | 10% | | | | | | | | | | | |
| R | | 40% | | | | | | | 58% | 16% | | 5% |
| S | 76% | | | 11% | | 34% | | | | | | 61% |
| T | | 17% | | | | | | | | | | |
| V | | | | | | | | | | | | |
| W | | | 76% | | | | 54% | | | 14% | | 7% |
| Y | | | | | | | | | | | | |
| % coverage | 86% | 82% | 88% | 85% | 88% | 91% | 94% | 98% | 98% | 65% | 88% | 87% |

| | CDR1 | | | | | | CDR2 | | | | | |
|---|---|---|---|---|---|---|---|---|---|---|---|---|
| # degenerate codons | 1 | 1 | 1 | 1 | 1 | 2 | 1 | 1 | 1 | 3 | 1 | 2 |

| | 4 oligos | | 24 oligos | |
|---|---|---|---|---|
| diversity | | 144 CDR1 diversity | | 1.03E+06 |

| D2E7 MATCHES | D | D | | | | | | | | | | | | |

*Blue highlighted residues are those found in both D2E7 and synthetic repertoire*

FIG. 16 (PART 1)

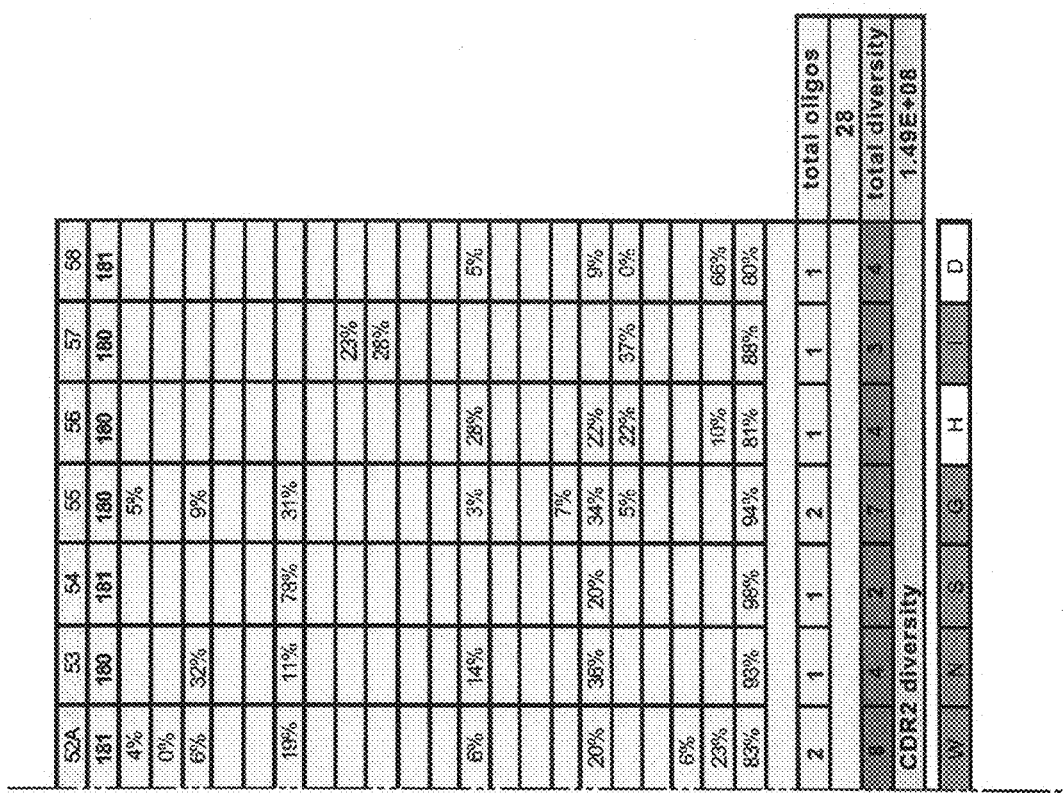
FIG. 16 (PART 2)

V_H3 Heavy Chain synthetic library diversity

- CDR3 contains $7.5 \times 10^9$ total diversity representing >80% positional coverage
- 384 degenerate oligonucleotides are required

| VH3 length 13 | 93 | 94 | 95 | 96 | 97 | 98 | 99 | 100 | 100A | 100B | 100C | 100D | 101 |
|---|---|---|---|---|---|---|---|---|---|---|---|---|---|
| # sequences | 114 | 114 | 114 | 114 | 114 | 114 | 114 | 114 | 114 | 114 | 114 | 114 | 114 |
| A | 96% | | 14% | | 18% | 5% | 2% | | 9% | 6% | 17% | | |
| C | | | | | | | | | | | | | |
| D | | | 23% | | 11% | 11% | | 4% | | 5% | | | 79% |
| E | | | | | 2% | | | | | | | | |
| F | | | | | 1% | | 5% | | | 4% | | 43% | |
| G | | | 23% | 14% | 12% | 14% | 14% | 25% | 7% | 13% | 7% | | 9% |
| H | | 56% | | 3% | | | | | | | 3% | | |
| I | | | | 4% | | 4% | 7% | | 11% | | | 1% | |
| K | | | | 17% | 5% | 12% | | | | | | 24% | |
| L | | | | | | | 4% | 4% | | | 2% | 8% | |
| M | | | | | | | | | 1% | | | | |
| N | | | 8% | 5% | | | 4% | | 8% | 6% | 13% | | |
| P | | | | 9% | | | | 5% | | | | | |
| Q | | | | | | | | | | | | | |
| R | | 26% | | 11% | 5% | 10% | 18% | 16% | 6% | 13% | 20% | | |
| S | | | 7% | 11% | 9% | 12% | 9% | 11% | 14% | 15% | 4% | | |
| T | | | 4% | 0% | | 12% | 9% | 5% | 8% | 6% | | | |
| V | | | | 8% | 6% | 6% | 4% | 5% | 2% | 4% | 4% | | |
| W | | | | | | | 7% | 7% | 15% | | | | |
| Y | | | | | 12% | 6% | 12% | 4% | 10% | 13% | 19% | | |
| % coverage | 95% | 82% | 79% | 82% | 83% | 82% | 87% | 80% | 80% | 85% | 90% | 76% | 88% |
| # degenerate codons | 1 | 1 | 1 | 2 | 2 | 2 | 2 | 2 | 2 | 2 | 2 | 1 | 1 |

CDR3 oligos: 384
$7.5 \times 10^9$ total CDR3 diversity

D2E7 MATCHES: A K V S Y L S T

Blue highlighted residues are those found in both D2E7 and synthetic repertoire

FIG. 17 (PART 1)

Positional omissions
- Residue 95 E (6% prevalence)
- Residue 98 P (5% prevalence)
- Residue 99 E (6% prevalence)
- Residue 100D G (11% prevalence)

Positional additions
- Indicated by shaded cell and bold text

FIG. 17 (PART 2)

Anti-hapten themed analysis

IG LAMBDA LIGHT CHAIN VARIABLE REGION
SYELTQPPSASGTPGQRVTISCSGSTSNIGSNYVYWYQHLPGTAPKLLIFRNSQRPS
GVPDRFSGSKSGTSASLAISGLRSEDEADYYCAAWDDSLSGVVFGGGTKLTVLG

HEAVY CHAIN VARIABLE REGION
EVQLVESGGGLVQPGGSLRLSCAASGFTFSSYAMSWVRQAPGKGLEWVSAISGSG
GSTYYADSVKGRFTISRDNSKNTLYLQMNSLRAEDTAVYYCAKDKGSGWYWGQGT
LVTVSS

FIG. 18

Determine Heavy and light chains origin

— VL-1g is most similar light chain
— VH 3-23 is most similar heavy chain anti dig HC    (1) EVQL...SGGGLVQPGGSLRLSCAASGFTFSSYAMSWVRQAPGKGLEWVSAISGSGGST
VH3_3-23       (1) EVQL...SGGGLVQPGGSLRLSCAASGFTFSSYAMSWVRQAPGKGLEWVSAISGSGGST
                   YYADSVKGRFTISRDNSKNTLYLQMNSLRAEDTAVYYCAKDGSWYWGQGTLVTVSS
                   YYADSVKGRFTISRDNSKNTLYLQMNSLRAEDTAVYYCAK anti dig LC    (1) SYELTQPPSASGTPGQRVTISCSGS SNIGSNYVYWYQ HLPGTAPKLLIY RNS
VL1_1g         (1) QSVLTQPPSASGTPGQRVTISCSGS SNIGSNYVYWYQ QLPGTAPKLLIY RNN
                   QRPSGVPDRFSGSKSGTSASLAISGLRSEDEADYYCAAWDDSLSG VVFGGGTKLTVLG
                   QRPSGVPDRFSGSKSGTSASLAISGLRSEDEADYYCAAWDDSLSG

FIG. 19

Hapten analysis for lambda length matched VL1 framework

| Hapten analysis | | 27C | 29 | 30 | 31 | 32 | 33 | 34 | 35 | 36 | 46 | 47 | 48 | 49 | 50 | 51 |
|---|---|---|---|---|---|---|---|---|---|---|---|---|---|---|---|---|
| # sequences | | 166 | 166 | 166 | 166 | 166 | 166 | 166 | 166 | 166 | 166 | 166 | 166 | 166 | 166 | 166 |
| Threshold percent usage | 6 | | | | | | | | | | | | | | | |
| A | | | | | | | | | | | | | | | | |
| C | | | | | | | | | | | | | | | | |
| D | | | | | | | | | | | | | | | 24% | 13% |
| E | | | | | | | | | | | | | | | 12% | |
| F | | | | | | | | | | | | | | | | |
| G | | | 92% | | | | | | | | | | | | 7% | |
| H | | | | | | | | | | | | | | | | |
| I | | 95% | | | | | | | | | | | 96% | | | |
| K | | | | | | | | | | | | | | | | |
| L | | | | | | | | | | | 94% | 95% | | | | |
| M | | | | | | | | | | | | | | | | |
| N | | | | 36% | 87% | | | 40% | | | | | | | 11% | 82% |
| P | | | | | | | | | | | | | | | | |
| Q | | | | | | | | | | | | | | | | |
| R | | | | 39% | | 7% | | 39% | | | | | | | 13% | |
| S | | | | | | 29% | 95% | | | | | | | | 18% | |
| T | | | | | | | | | 100% | | | | | | | |
| V | | | | | | | | | | | | | | | | |
| W | | | | | | 45% | | 13% | | 96% | | | | 87% | | |
| Y | | | | | | | | | | | | | | | | |
| % represented | | 95% | 92% | 75% | 87% | 81% | 95% | 92% | 100% | 96% | 94% | 95% | 96% | 87% | 85% | 95% |
| Acceptable? | | | | | | | | | | | | | | | | |
| Sum percent threshold | 75 | | | | | | | | | | | | | | | |
| | | | | | | CDR1 | | | | | | | CDR2 | | | |
| | | 1 | 1 | 1 | 1 | 2 | 1 | 2 | 1 | 1 | 1 | 1 | 1 | 1 | 3 | 1 |
| | | | | | | oligos | | | | | | | | | oligos | |
| | | | 1 | 2 | 1 | 2 | | 2 | | | | | | | 3 | 2 |
| | | | | | | | | | | | | | | | 5 | |
| | | | | | | 8 diversity | | | | | | | | | 40 diversity | |

Hapten analysis for H3 length 8

| unpaired VH3 analysis | | 93 | 94 | 95 | 96 | 97 | 98 | 99 | 101 |
|---|---|---|---|---|---|---|---|---|---|
| # sequences | | 32 | 32 | 32 | 32 | 32 | 32 | 32 | 32 |
| Threshold percent usage | 6.25 | | | | | | | | |
| A | | 91% | | 6% | 6% | 9% | | | 9% |
| C | | | | | | | | | |
| D | | | | 47% | | | | 6% | 56% |
| E | | | | | 16% | | | | |
| F | | | | 6% | | | 6% | 22% | |
| G | | | | 22% | 6% | 28% | 16% | | 9% |
| H | | | | | 9% | | | | |
| I | | | | | | | | | |
| K | | | 31% | | | | | | |
| L | | 6% | | | 6% | 6% | 9% | 9% | 6% |
| M | | | | | | | | | |
| N | | | | | | 16% | | 16% | 9% |
| P | | | | | | | | | |
| Q | | | | | 13% | | 6% | 6% | |
| R | | | 44% | | 19% | | | | |
| S | | | 9% | | | | 9% | | |
| T | | | | | | | 19% | | |
| V | | | | | 13% | | | 13% | |
| W | | | | 8% | | | 6% | | |
| Y | | | | | | 22% | 13% | 6% | |
| % represented | | 97% | 84% | 88% | 88% | 81% | 84% | 78% | 91% |
| Acceptable? | | | | | | | | | |
| | | | | CDR3 | | | | | |
| Sum percent threshold | 75 | | | | | | | | |

FIG. 21

Interferon Amino acids #32-38

| Interferon alpha example | | 32 | 33 | 34 | 35 | 36 | 37 | 38 |
|---|---|---|---|---|---|---|---|---|
| # sequences | | 11 | 11 | 11 | 11 | 11 | 11 | 11 |
| Threshold percent usage | 9 | | | | | | | |
| A | | | | | | | 64% | |
| C | | | | | | | | |
| D | | | 9% | | | | | |
| E | | | | | | | | |
| F | | | | | | | | |
| G | | | 64% | | | | | |
| H | | | | 9% | | | | |
| I | | | | | | | | |
| K | | | | | | | | |
| L | | 100% | | | | | | 91% |
| M | | | | | | | | |
| N | | | 9% | 91% | | | | 9% |
| P | | | | | | | | |
| Q | | | 9% | | | | | |
| R | | | 9% | | 100% | 100% | | |
| S | | | 9% | | | | | |
| T | | | | | | | 36% | |
| V | | | | | | | | |
| W | | | | | | | | |
| Y | | | | | | | | |
| % coverage | | 100% | 100% | 100% | 100% | 100% | 100% | 100% |
| # degenerate syntheses | 2 | 1 | 2 | 1 | 1 | 1 | 1 | 1 | diversity: 40

1. Align 11 IFN-α sequences amino acids #32-38
2. Determine residue frequency usage

```
                (30) 30                          43
P01563(30)      HSLGNRRALILLAQ
P05013(30)      HSLGSRRTMLLA
P01569(30)      HSLGNRRALILLMIA
P32881(30)      HSLGNRRALILLMTA
P01570(30)      HSLGNRRALILLLAQ
P05015(30)      HSLGNRRALILLAQ
P01568(30)      HSLGNRRALILLAQ
P01566(30)      HSLGNRRALILLAQ
P01571(30)      HSLGNRRALILLAQ
P01567(30)      HSLGNRRALILLAQ
P05014(30)      HSLGNRRALILLAQ
Consensus(30)   HSLGNRRALILLAQ
```

FIG. 22

Encoding IFN diversity

| | 32 | 33 | | | | 34 | | 35 | 36 | 37 | | 38 | | |
|---|---|---|---|---|---|---|---|---|---|---|---|---|---|---|
| | L | G | R | S | D | N | H | N | R | R | A | T | L | M | # Oligos |
| | C | T | G | | | | | C | A | C | G | T | G | C | T | G | |
| | T | G | G | | | | | A | A | T | G | C | A | T | G | |
| | | | A | G | | | | | | | | | | | |
| | | | G | A | | | | | | | | | | | |
| | | | A | A | | | | | | | | | | | |
| | 1 | 5 | | | | 2 | | 1 | 1 | 2 | | 2 | | 40 |

Degenerate design

| | | | | | | | | | | | | | | # Oligos |
|---|---|---|---|---|---|---|---|---|---|---|---|---|---|---|
| | C | T | V | G | T | M | A | T | C | G | T | R | C | T | M | T | G | |
| | | | R | A | T | | | | | | | | | | | | | |
| | 1 | 2 | | | 1 | | 1 | 1 | 1 | | 1 | | 2 |

| | | | | | | | | | | | | | | |
|---|---|---|---|---|---|---|---|---|---|---|---|---|---|---|
| ifn_01 | C | T | T | R | A | T | M | A | T | C | G | T | R | C | T | M | T | G |
| ifn_02 | C | T | T | V | G | T | M | A | T | C | G | T | R | C | T | M | T | G |

CONSTRUCTION OF DIVERSE SYNTHETIC PEPTIDE AND POLYPEPTIDE LIBRARIES

CROSS-REFERENCE TO RELATED APPLICATION

This is a non-provisional application claiming priority under 35 U.S.C. §119(e) from U.S. provisional patent application No. 60/849,035, filed Oct. 2, 2006, the entire disclosure of which is expressly incorporated by reference herein.

FIELD OF THE INVENTION

The present invention concerns the design and construction of diverse peptide and polypeptide libraries. In particular, the invention concerns methods of analytical database design for creating datasets using multiple relevant parameters as filters, and methods for generating sequence diversity by directed multisyntheses oligonucleotide synthesis. The present methods enable the reduction of large complex annotated databases to simpler datasets of related sequences, based upon relevant single or multiple key parameters that can be individually directly defined. The methods further enable the creation of diverse libraries based on this approach, using multisynthetic collections of discrete and degenerate oligonucleotides to capture the diverse collection of sequences, or portions thereof.

BACKGROUND OF THE INVENTION

The development of peptide- or polypeptide-based drug candidates often starts with the screening of libraries of related peptide or polypeptide sequences. Thus the first step for the selection of therapeutic antibody candidates usually is the creation of a highly diverse library of antibody sequences.

Several methods for the design and construction of diverse antibody libraries are known in the art.

It has been described that the diversity of a filamentous phage-based combinatorial antibody library can be increased by shuffling of the heavy and light chain genes (Kang et al., Proc. Natl. Acad. Sci. USA, 88:11120-11123, (1991)) or by introducing random mutations into the library by error-prone polymerase chain reactions (PCR) (Gram et al., *Proc. Natl. Acad. Sci. USA*, 89:3576-3580, (1992)). The use of defined frameworks as the basis for generating antibody libraries has been described by Barbas et al., *Proc. Nat. Acad. Sci. USA* 89:4457-4461 (1992) (randomizing CD3-H3); Barbas et al., *Gene* 137:57-62 (2003) (extending randomization to $V_\kappa$ CDR3); and Hayanashi et al., *Biotechniques* 17:310 (1994) (simultaneous mutagenesis of antibody CDR regions by overlap extension and PCR). Others report combination of CDR-H3 libraries with a single $V_L$ gene (Nissim et al., *EMBO J.* 13:692-698 (1994)), a limited set of $V_L$ genes (De Kruif et al., *J. Mol. Biol.* 248:97-105 (1995)); or a randomized repertoire of $V_L$ genes (Griffiths et al., *EMBO J.* 13:3245-3260 (1994)).

See also U.S. Pat. Nos. 5,667,988; 6,096,551; 7,067,284 describing methods for producing antibody libraries using universal or randomized immunoglobulin light chains.

Knappik et al., *J. Mol. Biol.* 296:57-86 (2000) describe a different concept for designing and constructing human antibody libraries, designated HuCAL (Human Combinatorial Antibody Libraries). This approach is based on the finding that each of the human $V_H$ and $V_L$ subfamilies that is frequently used during an immune response is represented by one consensus framework, resulting in seven HuCAL consensus genes for heavy chains and seven HuCAL consensus genes for light chains, which yield 49 possible combinations. All genes are made by total synthesis, taking into consideration codon usage, unfavorable residues that promote protein aggregation, and unique and general restriction sites flanking all CDRs. The approach leads to the generation of modular antibody genes containing CDRs that can be converted into different antibody formats, as needed. The design and synthesis of HuCAL antibody libraries is described in U.S. Pat. Nos. 6,300,064; 6,696,248; 6,706,484; and 6,828,422.

Despite these and other advances there a great need for new, efficient methods for the design and construction of highly diverse (poly)peptide, such as antibody, libraries.

SUMMARY OF THE INVENTION

The present invention concerns the design and construction of diverse peptide and polypeptide libraries.

In one aspect, the invention concerns a method for diversity analysis of a database comprising related amino acid sequences characterized by at least one shared sequence motif, comprising the steps of:

(a) aligning the related amino acid sequences;
(b) creating a first dataset by applying a predetermined combination of two or more filters to the related amino acid sequences comprising the shared sequence motif;
(c) analyzing the first dataset for positional amino acid usage frequency within the shared sequence motif; and
(d) creating a second dataset characterized by a minimum threshold amino acid usage frequency at one or more amino acid positions within the shared sequence motif.

In step (d) a minimum threshold amino acid usage frequency can be assigned to any and all amino acid positions within the shared sequence motif.

In one particular embodiment, a minimum threshold amino acid usage frequency is assigned to the majority of amino acid positions within the shared sequence motif. In another particular embodiment, a minimum threshold amino acid usage frequency is assigned to all amino acid positions within the shared sequence motif. In various embodiments, the minimum threshold amino acid usage frequencies assigned to specific amino acid positions within the shared sequence motif can be identical or different.

In a further embodiment, the minimum threshold amino acid usage frequency is set to provide a minimum sum amino acid usage for the majority of amino acid positions within the shared sequence motif.

In a still further embodiment, the minimum threshold amino acid usage frequency is set to provide a minimum sum amino acid usage for all amino acid positions within said shared sequence motif.

The minimum sum amino acid usage can be set to any desired level, and in particular embodiments it is at least about 40%, or at least about 45%, or at least about 50%, or at least about 55%, or at least about 60%, or at least about 65%, or at least about 70%, or at least about 75%, or at least about 80%, or at least about 85%, or at least about 90%.

In another embodiment, the related amino acid sequences are antibody sequences.

In yet another embodiment, the related amino acid sequences comprise antibody heavy chain sequences.

In a further embodiment, the related amino acid sequences comprise antibody light chain sequences.

If the related amino acid sequences are antibody sequences, the shared sequence motif may, for example, be a CDR sequence, such as a CDR1, CDR2 or CDR3 sequence.

There are no limitations on the nature or number of the filters that can be used in step (b) of the method of the present invention. In a particular embodiment, in the case of antibody sequences, the predetermined combination of filters can be selected from the group consisting of (1) the isotype of an antibody heavy or light chain; (2) the length of one or more of CDR1, CDR2 and CDR3 sequences; (3) the presence of one or more predetermined amino acid residues at one or more predetermined positions within one or more CDR1, CDR2 and CDR3 sequences; (4) type of framework; (5) antigen to which the antibody binds; (6) affinity of the antibody; and (7) positional amino acid residues outside the CDR sequences.

In a further embodiment, at least one of the antibody heavy and/or light chain CDR1, CDR2 and CDR3 sequences is size matched. This parameter can, for example, be combined with the isotype of the antibody heavy and/or light chain sequences, as an additional filter.

In various embodiments, the positional amino acid usage frequency is at least about 3%, or at least about 5%, or at least about 10%, or at least about 15%, or set between about 3% and about 15%, or between about 5% and about 10%.

In another embodiment of the methods of the present invention, the same positional amino acid usage frequency characterizes each amino acid within said CDR sequence. In an alternative embodiment, the positional amino acid usage frequencies differ at least two amino acid residues within said CDR sequence.

In another embodiment, the predetermined combination of filters includes the type of framework.

In yet another embodiment, both antibody heavy and light chain sequences are analyzed. Optionally, the antibody heavy chain sequences are paired to predetermined antibody light chain characteristics, or the antibody light chain sequences are paired to predetermined antibody heavy chain characteristics.

In a further embodiment, the related antibody sequences are from at least one functional antibody.

In a still further embodiment, at least one of the filters applied in step (b) of the method of the invention is the germline sequence most similar to the framework sequence of the heavy and/or light chain of a functional antibody.

Without limitation, the functional antibody may, for example, bind to a polypeptide selected from the group consisting of cell surface and soluble receptors, cytokines, growth factors, enzymes; proteases; and hormones. Thus, the antibody may bind to a cytokine, such as an interleukin, e.g. IL-1, IL-2, IL-3, IL-4, IL-5, IL-6, IL-10, IL-11, IL-12, IL-15, IL-17, IL-18, IL-23, and their respective family members. Alternatively, the cytokine may, for example, be selected from the group consisting of interferons-α, -β, and -γ (IFN-α, -β, and -γ), tumor necrosis factor-α, and -β(TNF-α and -β), TWEAK, RANKL, BLys, RANTES, MCP-1, MIP-1α, MIP-1β, SDF-1, colony stimulating factor (CSF), granulocyte colony stimulating factor (G-CSF), and granulocyte macrophage colony stimulating factor (GMCSF).

The polypeptide to which the antibody binds may also be a growth factor, including, without limitation, nerve growth factor (NGF), insulin-like growth factor 1 (IGF-1), epidermal growth factor (EGF), plateled derived growth factor (PDGF), vascular endothelial growth factor (VEGF), placental growth factor (PLGF), tissue growth factor-α(TGF-α), and tissue growth factor-β (TGF-β).

In another embodiment, the functional antibody binds to a hapten, e.g. Dig, Bio, DNP, or FITC.

In yet another embodiment of the methods herein, the related amino acid sequences originate from members of a family of secreted or extracellular proteins, which can be cytokines, for example.

In a specific embodiment, the cytokine is interferon-α, and the related amino acid sequences are sequences of IFN-α subtypes.

In a particular embodiment, the invention further comprises the step of synthesizing a physical library of related amino acid sequences that is designed with the aid of the datasets identified.

In a certain embodiment of this method, the library is synthesized by generating a discrete number of defined or degenerate oligonucleotides such that only defined amino acids are generated.

In a further embodiment, the diversity of the physical library produced exceeds the diversity of a library which is a physical representation of the datasets identified. This can, for example, result from the fact that at least one amino acid not meeting the minimum threshold amino acid usage frequency is also synthesized to provide said diversity.

In a still further embodiment, the diversity of the physical library produced is less than the diversity of a library which is a physical representation of the datasets identified. This can results from the fact that not all amino acids meeting the minimum threshold amino acid usage frequency are synthesized, for example.

In another embodiment, the dataset comprises antibody heavy and/or light chain sequence, which may include one or more CDRs.

In yet another embodiment, the CDRs are cloned into a scaffold of framework sequences, which may, optionally, be the most frequently used framework sequences in the database comprising said CDRs.

The physical library may be expressed using any expression system, including all prokaryotic and eukaryotic expression systems.

In a specific embodiment, the physical library is expressed and displayed using a phagemid display, RNA display, microbial cell display, mammalian cell display, microbead display technique, antibody array, or display based on protein-DNA linkage.

In another embodiment of the invention, the library is screened for one or more chemical and/or biological properties of its members. Such properties may include, without limitation, half-life, potency, efficacy, binding affinity, and immunogenicity.

In yet another embodiment, amino acid side-chain diversity is introduced into members of the library at one or more amino acid positions.

In a particular embodiment, the amino acid side-chain diversity is introduced by providing amino acid residues with at least two different side-chain chemical functionalities at said amino acid position or positions.

In other embodiments, at least 30%, or at least 50%, or at least 55%, or at least 60% of all amino acid chemistries are represented at each amino acid position.

Preferably, amino acid said side-chain diversity is introduced by using combinatorial degenerate oligonucleotide synthesis.

In another aspect, the invention concerns a method of producing a combinatorial library of peptide or polypeptide sequences, comprising introducing amino acid side-chain chemical diversity into the peptide or polypeptide sequences at two or more amino acid positions, using combinatorial oligonucleotide synthesis.

In one embodiment, the amino acid side-chain chemical diversity is designed to mimic naturally occurring diversity in said peptide or polypeptide sequences.

The library can be any type of library, including, but not limited to, antibody libraries.

In a specific embodiment, the antibody library comprises antibody heavy chain variable domain sequences.

In another embodiment, the library comprises antibody light chain variable domain sequences.

In yet another embodiment, the library is a combinatorial single-chain variable fragment (scFv) library.

In a further embodiment, the antibody library is a library of Fab, Fab', or F(ab')$_2$ fragments.

BRIEF DESCRIPTION OF THE DRAWINGS

The file of this patent contains at least one drawing executed in color. Copies of this patent or patent publication with color drawing(s) will be provided by the Office upon request and payment of the necessary fee.

FIG. 1 is a summary of the representative steps of the design and construction of a diverse human antibody library.

FIG. 2: Frequency analysis of V$_\kappa$ CDR1, 2, and 3; determination of absolute usage by position.

FIG. 3: V$_\kappa$ I light chain threshold analysis. No individual amino acids are reported below 10% usage.

FIG. 4: V$_\kappa$ I light chain threshold analysis. No individual amino acids are reported below 5% usage.

FIG. 5: Synthesizing light chain CDR1 diversity. The sequences of the 16 oligonucleotides used in the degenerate design (K1_1 to K1_16) are represented by SEQ ID NOS: 5 to 20.

FIG. 6: V$_H$3 heavy chain synthetic library threshold analysis; length 10 residues. The threshold percentage usage has been individually set for each amino acid position, and is between 3% and 10%.

FIG. 7: Oligonucleotides used to synthesize the library designated as shown in FIG. 6. The sequences of the oligonucleotides designated H3 3 10 001 through H3 3 10 096a are represented by SEQ ID NOS: 21 to 116.

FIG. 8: Determination of germline origin of productive anti-TNF-α antibody heavy chain. The various VH3 sequences (D2E7 through VH3_3-74 are represented by SEQ ID NOS: 117 to 138.

FIG. 12: V$_\kappa$1 light chain synthetic library diversity. The sequence of D2E7 matches shown at the bottom of the figure is represented by SEQ ID NO: 160.

FIG. 13: Frequency analysis of V$_H$3 CDR1 and CDR2.

FIG. 14: CDR1 and CDR2 threshold analysis—part one.

FIG. 15: CDR1 an CDR2 threshold analysis—part two.

FIG. 16: V$_H$3 heavy chain synthetic library diversity. The sequence of D2E7 matches shown at the bottom of the figure is represented by SEQ ID NO: 161.

FIG. 17: Design of V$_H$3 heavy chain synthetic library diversity based on anti-digoxigenin antibody D2E7. The sequence of D2E7 matches shown at the bottom of the figure is represented by SEQ ID NO: 162.

FIG. 18: Anti-digoxigenin antibody Ig λ light chain variable region (SEQ ID NO: 1) and heavy chain variable region (SEQ ID NO: 2) sequences.

FIG. 19: Determination of germline origin of anti-digoxigenin antibody heavy and light chains. The VL1_1g sequence is represented by SEQ ID NO: 163.

FIG. 20: Hapten analysis for λ length matched C$_L$1 framework.

FIG. 21: Hapten analysis for H3—length 8 amino acids.

FIG. 22: Alignment of amino acid residues 32-38 of IFN-α subtypes. The sequences of P01563; P05013; P01569; P32881; P01570; P05015; P01568; P01566; P01571; P01567; P05014; and the consensus sequence are represented by SEQ ID NOS: 165 to 171, respectively.

FIG. 23: Oligonucleotide design to encode desired IFN-α diversity. The oligonucleotide sequences encoding IFN-α diversity are represented by SEQ ID NO: 172; ifn_01: SEQ ID NO: 173; ifn_02: SEQ ID NO: 174.

FIG. 25: Encoding chemically probed diversity positions.

FIG. 27: Encoding CDR3 heavy chain diversity with chemical probe sets (SEQ ID NOS: 175 and 176).

DETAILED DESCRIPTION OF THE INVENTION

A. Definitions

Figure 9:
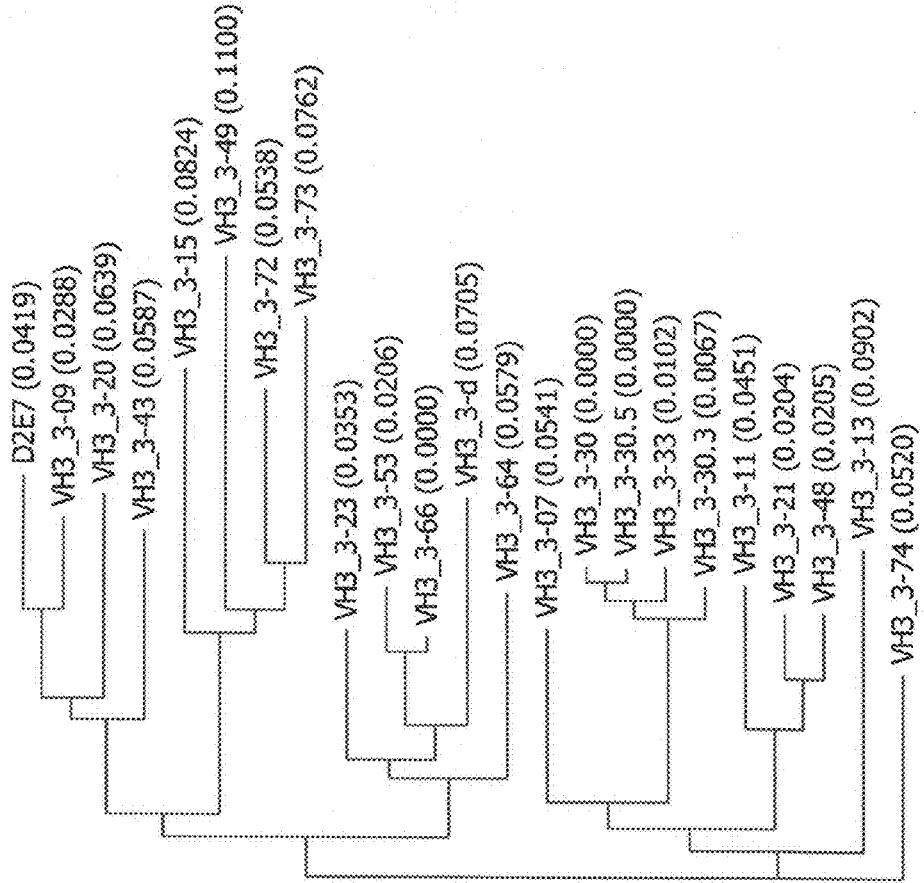
FIG. 9: Dendrogram alignment illustrating the germline origin of productive anti-TNF-α antibody heavy chain.

Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, N.Y. 1994), provides one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The phrase "shared sequence motif" is used herein in the broadest sense and is used to refer to a pattern of amino acid residues common between two or more peptide or polypeptide sequences. Sequence motifs can be readily identified by a variety of pattern discovery algorithms, such as those discussed in the detailed description of the invention.

In the context of the present invention, the term "antibody" (Ab) is used in the broadest sense and includes immunoglobulins which exhibit binding specificity to a specific antigen as well as immunoglobulins and other antibody-like molecules which lack antigen specificity. Polypeptides of the latter kind are, for example, produced at low levels by the lymph system and, at increased levels, by myelomas. In the present application, the term "antibody" specifically covers, without limitation, monoclonal antibodies, polyclonal antibodies, and antibody fragments.

"Native antibodies" are usually heterotetrameric glycoproteins of about 150,000 daltons, composed of two identical light (L) chains and two identical heavy (H) chains. Each light chain is linked to a heavy chain by covalent disulfide bond(s), while the number of disulfide linkages varies between the heavy chains of different immunoglobulin isotypes. Each heavy and light chain also has regularly spaced intrachain disulfide bridges. Each heavy chain has, at one end, a variable domain (V$_H$) followed by a number of constant domains. Each light chain has a variable domain at one end (V$_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains, Chothia et al., *J. Mol. Biol.* 186:651 (1985); Novotny and Haber, *Proc. Natl. Acad. Sci. U.S.A.* 82:4592 (1985).

The term "variable" with reference to antibody chains is used to refer to portions of the antibody chains which differ extensively in sequence among antibodies and participate in the binding and specificity of each particular antibody for its particular antigen. Such variability is concentrated in three segments called hypervariable regions both in the light chain and the heavy chain variable domains. The more highly conserved portions of variable domains are called the framework region (FR). The variable domains of native heavy and light chains each comprise four FRs (FR1, FR2, FR3 and FR4, respectively), largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991), pages 647-669). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen-binding. The hypervariable region comprises amino acid residues from a "complementarity determining region" or "CDR" (i.e., residues 30-36 (L1), 46-55 (L2) and 86-96 (L3) in the light chain variable domain and 30-35 (H1), 47-58 (H2) and 93-101 (H3) in the heavy chain variable domain; MacCallum et al., *J Mol. Biol.* 1996.

The term "framework region" refers to the art recognized portions of an antibody variable region that exist between the more divergent CDR regions. Such framework regions are typically referred to as frameworks 1 through 4 (FR1, FR2, FR3, and FR4) and provide a scaffold for holding, in three-dimensional space, the three CDRs found in a heavy or light chain antibody variable region, such that the CDRs can form an antigen-binding surface.

Depending on the amino acid sequence of the constant domain of their heavy chains, antibodies can be assigned to different classes. There are five major classes of antibodies IgA, IgD, IgE, IgG, and IgM, and several of these may be further divided into subclasses (isotypes), e.g., IgG1, IgG2, IgG3, IgG4, IgA, and IgA2.

The heavy-chain constant domains that correspond to the different classes of immunoglobulins are called α, δ, ε, γ, and μ, respectively.

The "light chains" of antibodies from any vertebrate species can be assigned to one of two clearly distinct types, called kappa (κ) and lambda (λ), based on the amino acid sequences of their constant domains.

"Antibody fragments" comprise a portion of a full length antibody, generally the antigen binding or variable domain thereof. Examples of antibody fragments include, but are not limited to, Fab, Fab', F(ab')$_2$; Dab, and Fv fragments, linear antibodies, single-chain antibody molecules, diabodies, and multispecific antibodies formed from antibody fragments.

The term "monoclonal antibody" is used to refer to an antibody molecule synthesized by a single clone of B cells. The modifier "monoclonal" indicates the character of the antibody as being obtained from a substantially homogeneous population of antibodies, and is not to be construed as requiring production of the antibody by any particular method. Thus, monoclonal antibodies may be made by the hybridoma method first described by Kohler and Milstein, *Nature* 256:495 (1975); *Eur. J. Immunol.* 6:511 (1976), by recombinant DNA techniques, or may also be isolated from phage antibody libraries.

The term "polyclonal antibody" is used to refer to a population of antibody molecules synthesized by a population of B cells.

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Plückthun in *The Pharmacology of Monoclonal Antibodies*, vol. 113, Rosenburg and Moore eds. Springer-Verlag, New York, pp. 269-315 (1994). Single-chain antibodies are disclosed, for example in WO 88/06630 and WO 92/01047.

As used herein the term "antibody binding regions" refers to one or more portions of an immunoglobulin or antibody variable region capable of binding an antigen(s). Typically, the antibody binding region is, for example, an antibody light chain (VL) (or variable region thereof), an antibody heavy chain (VH) (or variable region thereof), a heavy chain Fd region, a combined antibody light and heavy chain (or variable region thereof) such as a Fab, F(ab')$_2$, single domain, or single chain antibody (scFv), or a full length antibody, for example, an IgG (e.g., an IgG1, IgG2, IgG3, or IgG4 subtype), IgA1, IgA2, IgD, IgE, or IgM antibody.

The term "threshold frequency of occurrence" refers to a criterion of the invention which requires that a selected sequence for use in a library herein be derived from a sequence which has been determined to be a sequence favored to be expressed. Depending on the ultimate goal, such as the required degree of diversity, the desired size of library, the "threshold frequency of occurrence" can be set at different levels.

The term "amino acid" or "amino acid residue" typically refers to an amino acid having its art recognized definition such as an amino acid selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile); leucine (Leu); lysine (Lys); methionine (Met); phenylalanine (Phe), proline (Pro); serine (Ser); threonine (Thr); tryptophan (Trp); tyrosine (Tyr), and valine (Val) although modified, synthetic, or rare amino acids may be used as desired. Thus, modified and unusual amino acids listed in 37 CFR 1.822(b)(4) are specifically included within this definition and expressly incorporated herein by reference. Amino acids can be subdivided into various sub-groups. Thus, amino acids can be grouped as having a nonpolar side chain (e.g., Ala, Cys, Ile, Leu, Met, Phe, Pro, Val); a negatively charged side chain (e.g., Asp, Glu); a positively charged side chain (e.g., Arg, His, Lys); or an uncharged polar side chain (e.g., Asn, Cys, Gln, Gly, His, Met, Phe, Ser, Thr, Trp, and Tyr). Amino acids can also be grouped as small amino acids (Gly, Ala), nucleophilic amino acids (Ser, His, Thr, Cys), hydrophobic amino acids (Val, Leu, Ile, Met, Pro), aromatic amino acids (Phe, Tyr, Trp, Asp, Glu), amides (Asp, Glu), and basic amino acids (Lys, Arg) (see, FIG. 25).

The term "conserved amino acid residue" refers to an amino acid residue determined to occur with a high frequency, typically at least 50% or more (e.g., at about 60%, 70%, 80%, 90%, 95%, or higher), for a given residue position in two or more amino acid sequences compared.

The term "semi-conserved amino acid residue" refers to amino acid residues determined to occur with a high frequency between two or more amino acid sequences compared for a given residue position. When 2-3 residues, preferably 2 residues, that together, are represented at a frequency of about 40% of the time or higher (e.g., 50%, 60%, 70%, 80%, 90% or higher), the residues are determined to be semi-conserved.

The term "variable amino acid residue" refers to amino acid residues determined to occur with a variable frequency between two or more sequences compared for a given residue position. When many residues appear at a given position, the residue position is determined to be variable.

The term "variability profile" refers to the cataloguing of amino acids and their respective frequencies of occurrence present at a particular amino acid position within a polypeptide sequence, such as within a CDR of an antibody.

The term "polynucleotide(s)" refers to nucleic acids such as DNA molecules and RNA molecules and analogs thereof (e.g., DNA or RNA generated using nucleotide analogs or using nucleic acid chemistry). As desired, the polynucleotides may be made synthetically, e.g., using art-recognized nucleic acid chemistry or enzymatically using, e.g., a polymerase, and, if desired, be modified. Typical modifications include methylation, biotinylation, and other art-known modifications. In addition, the nucleic acid molecule can be single-stranded or double-stranded and, where desired, linked to a detectable moiety.

The term "mutagenesis" refers to, unless otherwise specified, any art recognized technique for altering a polynucleotide or polypeptide sequence. Preferred types of mutagenesis include error prone PCR mutagenesis, saturation mutagenesis, or other site directed mutagenesis.

The term "vector" is used to refer to a rDNA molecule capable of autonomous replication in a cell and to which a DNA segment, e.g., gene or polynucleotide, can be operatively linked so as to bring about replication of the attached segment. Vectors capable of directing the expression of genes encoding for one or more polypeptides are referred to herein as "expression vectors."

The term "primer," as used herein, refers to a polynucleotide whether purified from a nucleic acid restriction digestion reaction or produced synthetically, which is capable of acting as a point of initiation of nucleic acid synthesis when placed under conditions in which synthesis of a primer extension product which is complementary to a nucleic acid strand is induced. Such conditions may include the presence of nucleotides and a DNA polymerase, reverse transcriptase and the like, at a suitable temperature and pH. The primer is preferably single stranded, but may also be in a double stranded form. The primer must be sufficiently long to prime the synthesis of extension products in the presence of the agents for polymerization. The exact lengths of the primers will depend on many factors, including the complexity of the target sequence, temperature and the source of primer. A primer typically contains about 15 to about 25 nucleotides, but shorter and longer primers may also be used. Shorter primers generally require cooler temperatures to form stable complexes with the template.

A "phage display library" is a protein expression library that expresses a collection of cloned protein sequences as fusions with a phage coat protein. Thus, the phrase "phage display library" refers herein to a collection of phage (e.g., filamentous phage) wherein the phage express an external (typically heterologous) protein. The external protein is free to interact with (bind to) other moieties with which the phage are contacted. Each phage displaying an external protein is a "member" of the phage display library.

An "antibody phage display library" refers to a phage display library that displays antibodies or antibody fragments. The antibody library includes the population of phage or a collection of vectors encoding such a population of phage, or cell(s) harboring such a collection of phage or vectors. The library can be monovalent, displaying on average one single-chain antibody or antibody fragment per phage particle or multi-valent displaying, on average, two or more antibodies or antibody fragments per viral particle. The term "antibody fragment" includes, without limitation, single-chain Fv (scfv) fragments and Fab fragments. Preferred antibody libraries comprise on average more than $10^6$, or more than $10^7$, or more than $10^8$, or more than $10^9$ different members.

The term "filamentous phage" refers to a viral particle capable of displaying a heterogenous polypeptide on its surface, and includes, without limitation, f1, fd, Pf1, and M13. The filamentous phage may contain a selectable marker such as tetracycline (e.g., "fd-tet"). Various filamentous phage display systems are well known to those of skill in the art (see, e.g., Zacher et al. *Gene* 9: 127-140 (1980), Smith et al. *Science* 228: 1315-1317 (1985); and Parmley and Smith *Gene* 73: 305-318 (1988)).

The term "panning" is used to refer to the multiple rounds of screening process in identification and isolation of phages carrying compounds, such as antibodies, with high affinity and specificity to a target.

B. Detailed Description

Techniques for performing the methods of the present invention are well known in the art and described in standard laboratory textbooks, including, for example, Ausubel et al., *Current Protocols of Molecular Biology*, John Wiley and Sons (1997); *Molecular Cloning: A Laboratory Manual*, Third Edition, J. Sambrook and D. W. Russell, eds., Cold Spring Harbor, N.Y., USA, Cold Spring Harbor Laboratory Press, 2001; O'Brian et al., *Antibody Phage Display, Methods and Protocols*, Humana Press, 2001; *Phage Display: A Laboratory Manual*, C. F. Barbas III et al. eds., Cold Spring Harbor, N.Y., USA, Cold Spring Harbor Laboratory Press, 2001; and *Antibodies*, G. Subramanian, ed., Kluwer Academic, 2004. Mutagenesis can, for example, be performed using site-directed mutagenesis (Kunkel et al., *Proc. Natl. Acad. Sci. USA* 82:488-492 (1985)). PCR amplification methods are described in U.S. Pat. Nos. 4,683,192, 4,683,202, 4,800,159, and 4,965,188, and in several textbooks including "PCR Technology: Principles and Applications for DNA Amplification", H. Erlich, ed., Stockton Press, New York (1989); and "PCR Protocols: A Guide to Methods and Applications", Innis et al., eds., Academic Press, San Diego, Calif. (1990).

Information concerning antibody sequence analysis using the Kabat database and Kabat conventions may be found, e.g., in Johnson et al., The Kabat database and a bioinformatics example, *Methods Mol. Biol.* 2004; 248: 11-25; and Johnson et al., Preferred CDRH3 lengths for antibodies with defined specificities, *Int Immunol.* 1998, December; 10(12):1801-5.

Information regarding antibody sequence analysis using Chothia conventions may be found, e.g., in Chothia et al., Structural determinants in the sequences of immunoglobulin variable domain, *J Mol. Biol.* 1998 May 1; 278(2):457-79; Morea et al., Antibody structure, prediction and redesign, *Biophys Chem.* 1997; 68(1-3):9-16; Morea et al., Conformations of the third hypervariable region in the VH domain of immunoglobulins; *J Mol. Biol.* 1998, 275(2):269-94; Al-Lazikani et al., Standard conformations for the canonical structures of immunoglobulins, *J Mol. Biol.* 1997, 273(4):

927-48. Barre et al., Structural conservation of hypervariable regions in immunoglobulins evolution, Nat Struct Biol. 1994, 1(12):915-20; Chothia et al., Structural repertoire of the human VH segments, J Mol. Biol. 1992, 227(3):799-817 Conformations of immunoglobulin hypervariable regions, Nature. 1989, 342(6252):877-83; and Chothia et al., Review Canonical structures for the hypervariable regions of immunoglobulins, J Mol. Biol. 1987, 196(4):901-17).

1. In silico Design of Diverse (Poly)peptide Libraries

According to the present invention, the design of diverse (poly)peptide libraries starts with the use of a database of related (poly)peptide sequences of interest, and, typically, the identification of sequence motifs that are shared by individual members of the library. Various computer programs for identifying sequence motifs in polypeptides are well known in the art and can be used on-line. Thus, for example, sequence motifs can be identified using the ELPH (a general-purpose Gibbs sampler for finding motifs in a set of DNA or protein sequences), MEME (Multiple EM for Motif Elicitation system that allows one to discover motifs of highly conserved regions in groups of related DNA or protein sequences); PPSEARCH (allows to search sequences for motifs or functional patterns in the PROSITE database (EBI)); emotif (a research system that forms motifs for subsets of aligned sequences, and ranks the motifs that it finds by both their specificity and the number of supplied sequences that it covers (Stanford Bioinformatics Group)); and the like.

In the next step, one or more sequence motifs identified are aligned to each other, and subdivided into separate datasets, each dataset being characterized by sharing a predetermined combination of parameters characteristic of one or more of the aligned sequence motifs. Such parameter can, for example, be the length, the subfamily in which a particular sequence motif belongs, the species from which the sequence derives, biological function, etc. The datasets characterized by a given combination of two or more parameters are then analyzed by position for amino acid frequency usage to identify key amino acid usage in individual stretches of amino acids within the datasets.

Alignment of the sequence motifs can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

Determination of amino acid frequency usage can be based on the appearance of high degree (typically at least 50%), and preferably complete, identity in all members of the dataset in a given position (conserved amino acid residue), or appearance of an amino acid residue in two or more members (preferably the majority) of the dataset for a given residue position. Additional datasets characterized by one or more additional parameters can then be created, not all of which need to be sequence related.

For example, if the goal is to design a diverse antibody library, antibody heavy and light chain CDR sequences present in the Kabat database, an electronic database containing non-redundant rearranged antibody sequences, can be analyzed for positional frequencies with unique combinations (filters) of predetermined parameters. The Kabat database contains antibody protein sequences, which are annotated upon submission. Information from the Kabat database can be imported into other environments, such as, for example, a Microsoft Access database, which allows for convenient application of filters, and the results can be tabulated and further analyzed in using any other software, including, for example, Excel.

The approach of the present invention allows for simultaneous filtering of both antibody heavy and light chain sequences, using a wide array of parameters (filters) and combination of parameters (filters). Thus, the generation of diversity datasets for particular heavy chains can be linked to light chain restrictions of choice. For example, filters for the analysis of antibody heavy chain CDR sequences may include one or more of (1) pairing with a certain light chain type (e.g. kappa ($\kappa$) or lambda ($\lambda$)); (2) CDR size (e.g. CDR1=6 residues; CDR2=13 residues); and (3) CDR3 subfamily (e.g. $V_H1$ vs. $V_H3$). In the light chains, all CDRs may be size matched. For example, it can be pre-determined that CDR1=7, CDR2=10, and CDR3=8 amino acid residues. In addition, or in the alternative, the light chains can be filtered (sub-divided) based on the type of the light chain subfamily (e.g. $\kappa1$ or $\kappa3$ subfamily).

Thus, for example, heavy chain diversity analysis can be performed based upon pairing with $\kappa$ light chains, but the analysis may also be further restricted to those heavy chain sequences that pair with $V_\kappa3$ subfamily light chains, or to $\kappa$ light chains bearing a CDR3 containing a length of 8 amino acids, or a combination of both.

Additional filters for covariant analysis of antibody heavy and/or light chains may include, without limitation, isotype, antigen type, affinity, and/or positional residues not related to CDR or the type or subtype of antibody chain.

In addition, the present invention enables the design of themed libraries, based upon "productive" heavy and light chain pairings. Thus various antibodies to the same antigen, including commercial antibodies, can be subjected to diversity analysis to identify antibodies that are most likely to succeed in human therapy.

If the goal is the design of themed antibody libraries, based upon productive heavy and light chain pairings, one or more productive (e.g. commercial) antibodies are selected to a selected antigen. Next, the germline origins to both the heavy and light chains are determined, and the heavy and light chain CDR sequences of the same type (e.g. $V_H3$, $V_\kappa1$) are subjected to the type of multivariate analysis described above to create diversity datasets. Preferably, the analysis should be based only on size-matched CDRs.

In the methods of the present invention, alignment and application of filters are followed by positional analysis in order to determine the positional frequency of individual amino acids or groups of amino acids within the previously created datasets, and to generate diversity datasets, such as CDR diversity datasets. After determining the absolute positional amino acid usage for each amino acid position of interest, the thresholds for percentage usage and for sum usage of amino acids can be lowered, in order to accommodate greater coverage of diversity. Thus, for example, the required total coverage may be set to more than 80%, with no individual amino acid being represented below 10%.

The in silico modeling can be continually updated with additional modeling information, from any relevant source, e.g., from gene and protein sequence and three-dimensional databases and/or results from previously tested polypeptides, such as antibodies, so that the in silico database becomes more precise in its predictive ability.

In addition, the in silico subsets can be supplemented with results of biological assays, such as binding affinity/avidity results, biological activity of previously tested antibodies. In this way, structural features can be more closely correlated with expected performance for an intended use.

Design of CDR diversity datasets is followed by the synthesis of a collection of combinatorial (degenerate) oligonucleotide sequences providing the required diversity, and cloning of the collection on the background of a suitable template.

2. Construction of Diverse (Poly)peptide Libraries

After the creation of combinatorial positional diversity data sets as described above, physical combinatorial diversity sets can be generated by multisyntheses oligonucleotide synthesis. According to the present invention, instead of using a mutagenic code or mixed codon trimers, discrete degenerate oligonucleotide collections are generated that can be quantitatively restricted or relaxed to physically represent the combinatorial diversity sets produced through the foregoing analysis and design. Relaxing the criteria enables capture of the desired diversity through synthesis of fewer oligonucleotide probes, or to rationally expand the diversity set if the ability to clone the collection exceeds the predicted collection generated through diversity analysis. In addition, the physical combinatorial diversity sets can include side-products not found in the virtual diversity sets, with or without additional rule sets. This approach is most helpful in the field of combinatorial antibody library generation, but can also be rationally extended into other appropriate applications, such as to generating libraries of various polypeptide classes (e.g. growth factor libraries), etc. It is important to note that the physical library does not necessarily need to contain members comprising all amino acids at any given position that were identified by setting the threshold percentage usage as described above. For various reasons, for example in order to reduce the number of oligonucleotides needed, it may be advantageous to omit certain amino acid(s) at a given position. Alternatively or in addition, it is possible to increase coverage and diversity of the library by synthesizing members with amino acid residue(s) at a given position that did not meet the pre-set threshold frequency usage. The two approaches can be combined, i.e. certain amino acid residues present in the in silico diversity data sets may be omitted while others, not represented in the in silico diversity data sets at a given position may be added.

The first step in the creation of peptide or polypeptide libraries herein is the reverse translation of a collection of amino acids for multiplexed synthesis to contain an entire positional collection. Reverse translation tools are well known in the art and are commercially available. For example, the Java-based backtranslation tool of Entelechon (DE) translated proteins into nucleotides sequences with adapted codon usage, and allows optimization of a sequence for expression in specific organisms. In a preferred embodiment, the methods of the present invention employ an automated reverse translation algorithm capable of synthesizing discrete and degenerate sets of oligonucleotides to represent the diversity tables created by in silico analysis. This algorithm can include or exclude particular codons and even incorporate non-equimolar degeneracies to more accurately achieve not only the diversity of the dataset but also the relative distributions.

The number of oligonucleotides needed can be restricted by selecting degenerate bases to simultaneously encoding more than one of the frequently used amino acids at a time. In addition, such degenerate bases can be restricted to avoid rare codons of the species of interest. For example, if the collection is synthesized in *E. coli*, the use of rare arginine codon usage for *E. coli* can be restricted in the reverse translation. In addition, it is known that not all amino acids are used with the same frequency. Therefore, non-equimolar mixes can be used to more accurately reflect the profile of the virtual (in silico) diversity tables.

Where positional diversity requires the synthesis of more oligonucleotides than desired, diversity can be arbitrarily defined with a chemical probe collection. Thus, amino acid side-chain chemistries can be captured within subsets of amino acids, such as small, hydrophobic, aromatic, basic, acidic, amide, nucleophilic, etc. amino acids can constitute such subsets. As the Examples will illustrate, such chemically probed diversity positions can be synthesized by using a much smaller number of oligonucleotides than would otherwise be required. Chemically probed diversity covers much of the naturally occurring diversity, and provides broad interactive chemistries.

When constructing the diverse antibody libraries of the present invention, modified amino acid residues, for example, residues outside the traditional 20 amino acids used in most polypeptides, e.g., homocysteine, can be incorporated into the antibody sequences, such as CDRs, as desired. This can be carried out using art recognized techniques which typically introduce stop codons into the polynucleotide where the modified amino acid residue is desired. The technique then provides a modified tRNA linked to the modified amino acid to be incorporated (a so-called suppressor tRNA of, e.g., the stop codon amber, opal, or ochre) into the polypeptide (see, e.g., Köhrer et al., *PNAS*, 98, 14310-14315 (2001)).

In a preferred embodiment, one or more of the above steps are computer-assisted. In a particular embodiment, the computer assisted step comprises, e.g., mining the Kabat database and, optionally, cross-referencing the results against the Vbase sequence directory (Tomlinson, I M. et al., .VBASE Sequence Directory. Cambridge, U.K.: MRC Centre for Protein Engineering; 1995). The methods of the present invention are amendable to a high throughput approach comprising software (e.g., computer-readable instructions) and hardware (e.g., computers, robotics, and chips) for carrying out the various steps.

The oligonucleotides for generation of the libraries herein can be synthesized by known methods for DNA synthesis. Known synthesis methods include the phosphoramidite chemistry (Beaucage and Caruthers, *Tetrahedron Letts.*, 22(20):1859 1862 (1981)), which permits effective oligo preparation, especially in the most common 40 80 bp size range, using an automated synthesizer, as described, for example, in Needham-VanDevanter et al. *Nucleic Acids Res.*, 12:6159 6168 (1984)). In addition, oligonucleotides can be synthesized by the triester, phosphite, and H-phosphonate methods, all well known in the art. For a review of the oligonucleotide synthesis methods see, for example, "Oligonucleotide Synthesis: A Practical Approach", ed. M. J. Gait, JRL Press, New York, N.Y. (1990). Oligonucleotides can also be custom ordered from a variety of commercial sources, such as, for example, The Midland Certified Reagent Company (Midland, Tex.), The Great American Gene Company (Salt Lake City, Utah), ExpressGen Inc. (Chicago, Ill.), Operon Technologies Inc. (Alameda, Calif.).

If the library is an antibody library, in the next step diversity is cloned into frameworks to produce a diverse antibody library.

The framework scaffold can be selected by methods well known in the art. Thus, the most frequently used frameworks in the database can be chosen for use as a scaffold, and diversity is cloned into the germline frameworks. For framework sequence selection, a subset of all available framework scaffolds determined to have been expressed in response to a particular antigen are arrayed. By determining the frameworks that are most frequently expressed in nature in response to a given antigen class an appropriate framework acceptor is selected. For example, to determine the preferred acceptor frameworks expressed in response to protein-based antigens, the Kabat database is searched for "protein-directed" frameworks. If preferred acceptor sequences are needed for presenting CDRs against a different antigen class, and/or, acceptor sequences of a particular species, the Kabat protein sequence filter is set accordingly. Thus, to determine sequences for use as human therapeutics against protein-based targets, the filter is set to focus only on human antibody sequences that recognize protein/peptide antigens. This greatly reduces redundancy in the dataset and sequence information that would bias results. Such analysis can be performed for $V_H$, $V_\kappa$ and/or $V_\lambda$ genes in a similar manner.

The diverse collections can be incorporated on an acceptor that is target specific to generate variant collections for antibody engineering.

The CDR diversity generated can be incorporated into framework regions by methods known in the art, such as polymerase chain reaction (PCR). For example, the oligonucleotides can be used as primers for extension. In this approach, oligonucleotides encoding the mutagenic cassettes corresponding to the defined region (or portion thereof), such as a CDR, are complementary to each other, at least in part, and can be extended to form a large gene cassette (e.g. a scFv) using a polymerase, e.g., a Taq polymerase.

In another approach, partially overlapping oligonucleotides are designed. The internal oligonucleotides are annealed to their complementary strand to yield a double-stranded DNA molecule with single-stranded extensions useful for further annealing. The annealed pairs can then be mixed together, extended, and ligated to form full-length double-stranded molecules using PCR. Convenient restriction sites can be designed near the ends of the synthetic gene for cloning into a suitable vector. In this approach, degenerate nucleotides can also be directly incorporated in place of one of the oligonucleotides. The complementary strand is synthesized during the primer extension reaction from a partially complementary oligonucleotide from the other strand by enzymatic extension with the aid of a polymerase. Incorporation of the degenerate polynucleotides at the stage of synthesis simplifies cloning, for example, where more than one domain or defined region of a gene is mutagenized or engineered to have diversity.

Regardless of the method used, after conversion into double stranded form, the oligonucleotides can be ligated into a suitable expression vector by standard techniques. By means of an appropriate vector, such as a suitable plasmid, the genes can be introduced into a cell-free extract, or prokaryotic cell or eukaryotic cell suitable for expression of the antibodies.

In a different approach, the desired coding sequence can be cloned into a phage vector or a vector with a filamentous phage origin of replication that allows propagation of single-stranded molecules with the use of a helper phage. The single-stranded template can be annealed with a set of degenerate oligonucleotides representing the desired mutations, elongated and ligated, thus incorporating each analog strand into a population of molecules that can be introduced into an appropriate host (see, e.g., Sayers, J. R. et al., Nucleic Acids Res. 16: 791-802 (1988)).

Various phagemid cloning systems suitable for producing the libraries, such as synthetic human antibody libraries, herein are known in the art, and have been described, for example, by Kang et al., Proc. Natl. Acad. Sci., USA, 88:4363 4366 (1991); Barbas et al., Proc. Natl. Acad. Sci. USA, 88:7978 7982 (1991); Zebedee et al., Proc. Natl. Acad. Sci., USA, 89:3175 3179 (1992); Kang et al., Proc. Natl. Acad. Sci., USA, 88:11120 11123 (1991); Barbas et al., Proc. Natl. Acad. Sci., USA, 89:4457 4461 (1992); and Gram et al., Proc. Natl. Acad. Sci., USA, 89:3576 3580 (1992).

The size of the library will vary depending upon the CDR length and the amount of CDR diversity which needs to be represented. Preferably, the library will be designed to contain less than $10^{15}$, $10^{14}$, $10^{13}$, $10^{12}$, $10^{11}$, $10^{10}$, $10^9$, $10^8$, $10^7$, and more preferably, $10^6$ or less antibodies or antibody fragments.

The libraries constructed in accordance with the present invention may be also attached to a solid support, such as a microchip, and preferably arrayed, using art recognized techniques.

The libraries constructed in accordance with the present invention can be expressed using any methods known in the art, including, without limitation, bacterial expression systems, mammalian expression systems, and in vitro ribosomal display systems.

In a preferred embodiment, the present invention encompasses the use of phage vectors to express the diverse libraries herein. The method generally involves the use of a filamentous phage (phagemid) surface expression vector system for cloning and expression. See, e.g., Kang et al., Proc. Natl. Acad. Sci., USA, 88:4363-4366 (1991); Barbas et al., Proc. Natl. Acad. Sci., USA, 88:7978-7982 (1991); Zebedee et al., Proc. Natl. Acad. Sci., USA, 89:3175-3179 (1992); Kang et al., Proc. Natl. Acad. Sci., USA, 88:11120-11123 (1991); Barbas et al., Proc. Natl. Acad. Sci., USA, 89:4457-4461 (1992); Gram et al., Proc. Natl. Acad. Sci., USA, 89:3576-3580 (1992); Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); and U.S. Pat. Nos. 5,698,426; 5,233,409; 5,580,717; 5,427,908; 5,750,753; 5,821,047; 5,403,484; 5,571,698; 5,516,637; 5,780,225; 5,658,727; 5,733,743; 5,837,500; 5,969,108; 6,326,155; 5,885,793; 6,521,404; 6,492,160, 6,492,123; 6,489,123; 6,342,588; 6,291,650; 6,225,447; 6,180,336; 6,172,197; 6,140,471; 5,994,519; 6,969,108; 5,871,907; and 5,858,657.

The vector is used to transform a recombinant host cell, which is cultured to allow the introduced phage genes and display protein genes to be expressed, and for phage particles to be assembled and shed from the host cell. The shed phage particles are then harvested (collected) from the host cell culture media and screened for desirable antibody binding properties. Typically, the harvested particles are "panned" for binding with a preselected antigen. The strongly binding particles are collected, and individual species of particles are clonally isolated and further screened for binding to the antigen. Phages which produce a binding site of desired antigen binding specificity are selected.

It is emphasized that the methods of the present invention are not limited by any particular technology used for the expression and display of antibody libraries. Other display techniques, such as ribosome or mRNA display (Mattheakis et al., Proc. Natl. Acad. Sci. USA 91:9022-9026 (1994); Hanes and Pluckthun, Proc. Natl. Acad. Sci. USA 94:4937-4942 (1997)), microbial cell display, such as bacterial display (Georgiou et al., Nature Biotech. 15:29-34 (1997)), or yeast cell display (Kieke et al., Protein Eng. 10:1303-1310 (1997)), display on mammalian cells, spore display, viral display, such as retroviral display (Urban et al., Nucleic Acids Res. 33:e35 (2005), display based on protein-DNA linkage (Odegrip et al., Proc. Acad. Natl. Sci. USA 101:2806-2810 (2004);

Reiersen et al., *Nucleic Acids Res.* 33:e10 (2005)), and microbead display (Sepp et al., *FEBS Lett.* 532:455-458 (2002)) are also suitable.

In ribosome display, the antibody and the encoding mRNA are linked by the ribosome, which at the end of translating the mRNA is made to stop without releasing the polypeptide. Selection is based on the ternary complex as a whole.

In a mRNA display library, a covalent bond between an antibody and the encoding mRNA is established via puromycin, used as an adaptor molecule (Wilson et al., *Proc. Nat. Acad. Sci. USA* 98:3750-3755 (2001)). For use of this technique to display antibodies, see, e.g., Lipovsek and Pluckthun, *J. Immunol. Methods.* 290:51-67 (2004).

Microbial cell display techniques include surface display on a yeast, such as *Saccharomyces cerevisiae* (Boder and Wittrup, *Nat. Biotechnol.* 15:553-557 (1997)). Thus, for example, antibodies can be displayed on the surface of *S. cerevisiae* via fusion to the α-agglutinin yeast adhesion receptor, which is located on the yeast cell wall. This method provides the possibility of selecting repertoires by flow cytometry. By staining the cells by fluorescently labeled antigen and an anti-epitope tag reagent, the yeast cells can be sorted according to the level of antigen binding and antibody expression on the cell surface. Yeast display platforms can also be combined with phage (see, e.g., Van den Beucken et al., *FEBS Lett.* 546:288-294 (2003)).

For a review of techniques for selecting and screening antibody libraries see, e.g., Hoogenboom, *Nature Biotechnol.* 23(9):1105-1116 (2005).

The invention will be illustrated by the following, non-limiting Examples.

EXAMPLES

Techniques for performing the methods of the present invention are well known in the art and described in standard laboratory textbooks, including, for example, Ausubel et al., *Current Protocols of Molecular Biology*, John Wiley and Sons (1997); *Molecular Cloning: A Laboratory Manual*, Third Edition, J. Sambrook and D. W. Russell, eds., Cold Spring Harbor, N.Y., USA, Cold Spring Harbor Laboratory Press, 2001; O'Brian et al., *Antibody Phage Display, Methods and Protocols*, Humana Press, 2001; *Phage Display: A Laboratory Manual*, C. F. Barbas III et al. eds., Cold Spring Harbor, N.Y., USA, Cold Spring Harbor Laboratory Press, 2001; and *Antibodies*, G. Subramanian, ed., Kluwer Academic, 2004. Mutagenesis can, fore example, be performed using site-directed mutagenesis (Kunkel et al., *Proc. Natl. Acad. Sci. USA* 82:488-492 (1985)); *DNA Cloning*, Vols. 1 and 2, (D. N. Glover, Ed. 1985); *Oligonucleotide Synthesis* (M. J. Gait, Ed. 1984); *PCR Handbook Current Protocols in Nucleic Acid Chemistry*, Beaucage, Ed. John Wiley & Sons (1999) (Editor); *Oxford Handbook of Nucleic Acid Structure*, Neidle, Ed., Oxford Univ Press (1999); *PCR Protocols: A Guide to Methods and Applications*, Innis et al., Academic Press (1990); *PCR Essential Techniques: Essential Techniques*, Burke, Ed., John Wiley & Son Ltd (1996); *The PCR Technique: RT-PCR*, Siebert, Ed., Eaton Pub. Co. (1998); *Antibody Engineering Protocols (Methods in Molecular Biology)*, 510, Paul, S., Humana Pr (1996); *Antibody Engineering: A Practical Approach (Practical Approach Series,* 169), McCafferty, Ed., Irl Pr (1996); *Antibodies: A Laboratory Manual*, Harlow et al., C. S. H. L. Press, Pub. (1999); *Large-Scale Mammalian Cell Culture Technology*, Lubiniecki, A., Ed., Marcel Dekker, Pub., (1990). Border et al., Yeast surface display for screening combinatorial polypeptide libraries, *Nature Biotechnology*, 15(6):553-7 (1997); Border et al., Yeast surface display for directed evolution of protein expression, affinity, and stability, *Methods Enzymol.*, 328:430-44 (2000); ribosome display as described by Pluckthun et al. in U.S. Pat. No. 6,348,315, and Profusion™ as described by Szostak et al. in U.S. Pat. Nos. 6,258,558; 6,261,804; and 6,214,553; and bacterial periplasmic expression as described in US20040058403A1.

Further details regarding antibody sequence analysis using Kabat conventions may be found, e.g., in Johnson et al., The Kabat database and a bioinformatics example, Methods Mol. Biol. 2004; 248:11-25; Johnson et al., Preferred CDRH3 lengths for antibodies with defined specificities, Int Immunol. 1998, December; 10(12):1801-5; Johnson et al., SEQHUNT. A program to screen aligned nucleotide and amino acid sequences, Methods Mol. Biol. 1995; 51:1-15. and Wu et al., Length distribution of CDRH3 in antibodies; and Johnson et al., Proteins. 1993 May; 16(1):1-7. Review).

Further details regarding antibody sequence analysis using Chothia conventions may be found, e.g., in Chothia et al., Structural determinants in the sequences of immunoglobulin variable domain, *J Mol Biol.* 1998 May 1; 278(2):457-79; Morea et al., Antibody structure, prediction and redesign, *Biophys Chem.* 1997 October; 68(1-3):9-16; Morea et al., Conformations of the third hypervariable region in the VH domain of immunoglobulins; *J Mol Biol.* 1998 Jan. 16; 275(2):269-94; Al-Lazikani et al., Standard conformations for the canonical structures of immunoglobulins, *J Mol. Biol.* 1997 Nov. 7; 273(4):927-48. Barre et al., Structural conservation of hypervariable regions in immunoglobulins evolution, Nat Struct Biol. 1994 December; 1(12):915-20; Chothia et al., Structural repertoire of the human VH segments, *J Mol Biol.* 1992 Oct. 5; 227(3):799-817 Conformations of immunoglobulin hypervariable regions, Nature. 1989 Dec. 21-28; 342(6252):877-83; and Chothia et al., Review Canonical structures for the hypervariable regions of immunoglobulins, *J Mol Biol.* 1987 Aug. 20; 196(4):901-17).

Further details regarding Chothia analysis are described, for example, in Morea V, Tramontano A, Rustici M, Chothia C, Lesk A M. Conformations of the third hypervariable region in the VH domain of immunoglobulins. J Mol Biol. 1998 Jan. 16; 275(2):269-94; Chothia C, Lesk A M, Gherardi E, Tomlinson I M, Walter G, Marks J D, Llewelyn M B, Winter G. Structural repertoire of the human VH segments. J Mol Biol. 1992 Oct. 5; 227(3):799-817; Chothia C, Lesk A M, Tramontano A, Levitt M, Smith-Gill S J, Air G, Sheriff S, Padlan E A, Davies D, Tulip W R, et al. Conformations of immunoglobulin hypervariable regions. Nature. 1989 Dec. 21-28; 342(6252):877-83; Chothia C, Lesk A M. Canonical structures for the hypervariable regions of immunoglobulins. J Mol Biol. 1987 Aug. 20; 196(4):901-17; and Chothia C, Lesk A M. The evolution of protein structures. Cold Spring Harb Symp Quant Biol. 1987; 52:399-405.

Further details regarding CDR contact considerations are described, for example, in MacCallum R M, Martin A C, Thornton J M. Antibody-antigen interactions: contact analysis and binding site Topography. J Mol Biol. 1996 Oct. 11; 262(5):732-45.

Further details regarding the antibody sequences and databases referred to herein are found, e.g., in Tomlinson I M, Walter G, Marks J D, Llewelyn M B, Winter G. The repertoire of human germline VH sequences reveals about fifty groups of VH segments with different hypervariable loops. J Mol Biol. 1992 Oct. 5; 227(3):776-98; Li W, Jaroszewski L, Godzik A. Clustering of highly homologous sequences to reduce the size of large protein databases. Bioinformatics. 2001 March; 17(3):282-3.

Example 1

Frequency Analysis of Antibody Light Chain $V_\kappa 1$ CDR1, 2, and 3 Sequences In a first step, 2374 human antibody $V_\kappa 1$ light chain variable domain sequences were collected from the Kabat Database of Sequences of Proteins of Immunological Interest. For each sequence, the gene sequence was translated into the corresponding amino acid sequence, and the amino acid sequences were positionally aligned, following the Kabat numbering system.

Next, the collection of $V_\kappa 1$ light chain sequences obtained was filtered by selecting sequences having amino acids "RV" at positions and 18-19, and applying the following length restrictions. CDR1=7 amino acids, CDR2=10 amino acids, and CDR3=8 amino acids. By applying these filters, the originally 2374-member collection was reduced to 771 members.

By using only entries containing complete unambiguous sequences from the "RV" motif preceding DR1 through a complete CDR3 sequence, the number of $V_\kappa 1$ light chain variable domain sequences was further reduced to 383.

Subsequently, the sequences were aligned, the occurrence amino acids at each position was tabulated, and the distribution of the 20 naturally occurring amino acids at each position was calculated to produce the positional frequency-based database of CDR domain diversity based on absolute usage of amino acids by position. The results of this tabulation are shown in FIG. 2.

The datasets set forth in FIG. 2 were further filtered by reporting only amino acid usage that was above 10% for any given position. The results are set forth in FIG. 3. In order to assess the effect of the percentage usage specified on diversity, another dataset was created by including only amino acid usage that was above 5%. The results are shown in FIG. 4. From comparing the datasets of FIGS. 3 and 4, it is clear that greater coverage of diversity is achieved by requiring a lower percentage of amino acid usage.

As shown in FIG. 5, in order to encode the light chain CDR1 diversity set forth in FIG. 4, 128 combinatorial oligonucleotides or 16 degenerate combinatorial oligonucleotides need to be synthesized. The bases need not be equimolar and can be tuned to bias amino acid usage to reflect frequencies found in the present analysis, and even include residues not included in the frequency tables. Alternatively or in addition, residues included in the frequency tables may be omitted, for example to further reduce the number of oligonucleotides needed for synthesis.

Example 2

Design of $V_H 3$ Heavy Chain Synthetic Library Diversity

Figure 7:
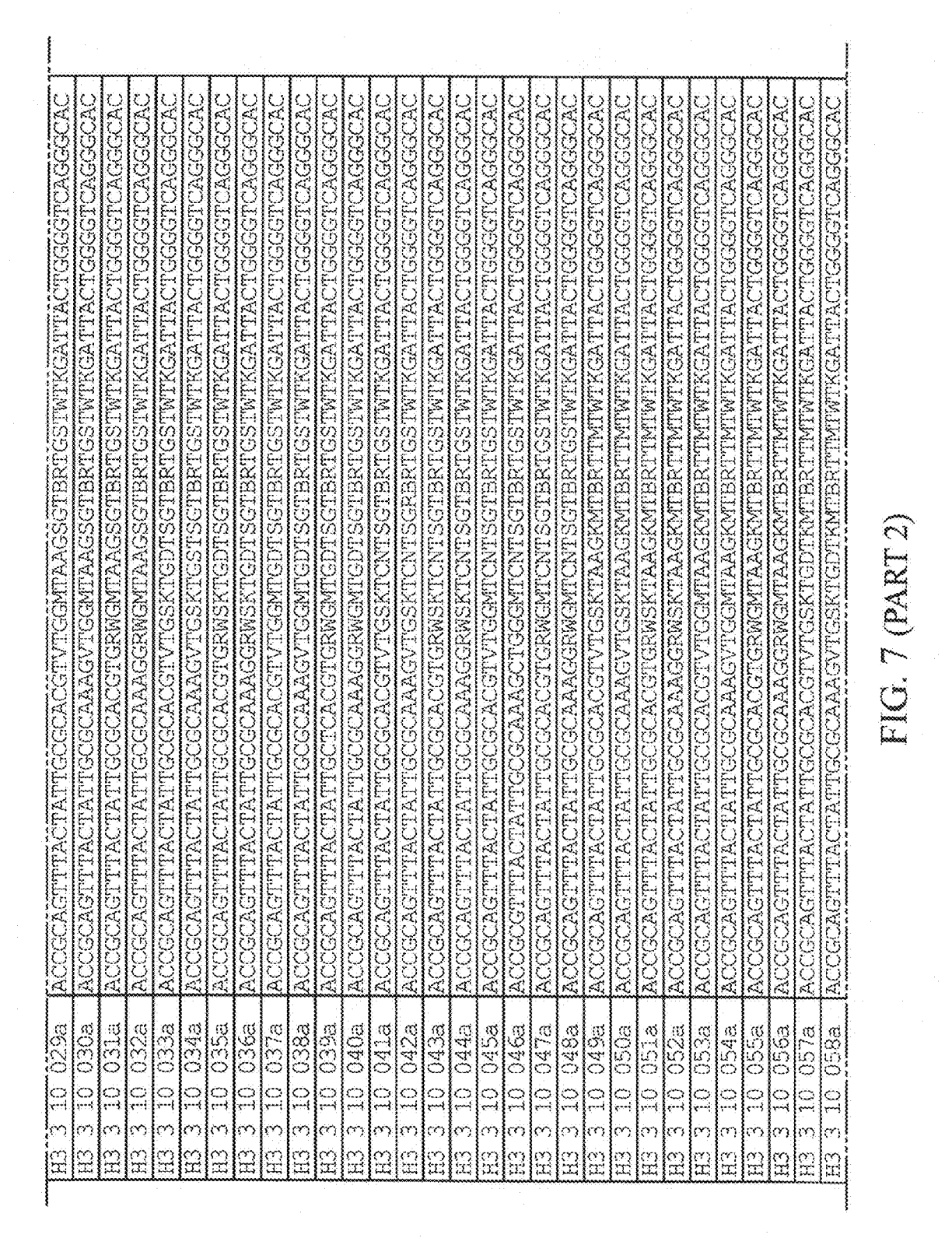

Analyzing $V_H 3$ heavy chain polypeptide sequences, 10 amino acids in length, obtained from the Kabat database of antibody sequences essentially as described in Example 1, the data shown in FIG. 6 was generated. As shown in FIG. 6, a CDR3 diversity of $3.3 \times 10^5$ representing at least 75% positional coverage for all positions except residue 97 can be provided by using only 96 degenerate oligonucleotides, setting different threshold percent usages for various amino acid positions. Thus the threshold percentage usage was 10% for positions 93, 94, 100 and 101; 5% for positions 95, 96, 98, and 99; 4% for position 97; and 3% for position 100A. The oligonucleotide sequences needed to synthesize this diversity are shown in FIG. 7.

Example 3

Making a Semi-Synthetic Antibody Library

As previously described, the analysis and generation of the $V_H$ CDR diversity can be tuned to contextually reflect compositions for productive and specific pairings with κ or λ light chains, (i.e. pairings resulting in antibodies specifically binding a target antigen). These synthetic $V_H$ repertoires need not exclusively be paired with synthetic light chain repertoires, but can be combinatorially cloned with collections of lymphocyte derived light chains. In practice, a collection of κ and λ light chains is separately cloned into a phage display vector followed by cloning of either the individual heavy chain variable region frameworks for subsequent introduction of diversity or a collection of pre-diversified variable region frameworks. In either case, the light chain compatibly paired heavy chain variable regions are expected to more productively pair with the corresponding light chains.

Example 4

Engineering Improved Antibodies by Creating Libraries of Variants Upon a Base Clone In a matter analogous to introducing productive diversity upon a germline acceptor frameworks for creating de novo immunoglobulin repertoires, target specific mutagenesis libraries are created for a specific antibody or defined collection of antibodies. Such libraries are useful in the task of antibody engineering especially in the field of affinity maturation. Starting with a monoclonal antibody of interest, the defining characteristics are determined, which are captured in the previously defined diversity influencing elements of the present invention, such as, germline framework origin, light chain type, and light chain and heavy chain CDR lengths. After determining these or similar characteristics the next step is to refer to database sequences that correspond these parameters. Subsequent to identifying the corresponding sets of sequences an analysis, similar to that described earlier, is performed to examine subset repertoire diversity and then generate the corresponding multi-degenerate oligonucleotides necessary to encode the desired diversity. These multi-degenerate oligonucleotides are then cloned as single or combinatorial CDR collections. As it is more likely to find synergistic improvements with multi-CDR mutagenesis the creation of combinatorial CDR mutagenesis libraries is preferred. Using the multi-degenerate oligonucleotides from the analysis described above rationally creates and re-diversifies antibodies according to positional diversity with respect to human bias and preference. It is important to note that in instances where any of the light chain CDR sequences or heavy chain CDR1 or CDR2 sequences diverge from the germline sequence the corresponding germline-encoding oligonucleotide is also included into the combinatorial CDR library. This inclusion of germline encoding oligonucleotides allows for backcrossing of germline sequences to create more productive CDR combinations.

This "diversity reincorporation scheme" is also useful in engineering a re-diversified set of antibodies from an existing synthetic antibody clone. As the potential diversity of the synthetic libraries created in accordance with the present invention exceeds the limits of currently available techniques to display and select all members, it is very likely that any discovered target specific clones represent only a fraction of the possible solutions present and accessible at the DNA-level of any of the typically screened libraries. Thus, after identifying in a library of the present invention, following four rounds of panning, an anti-EGF antibody, the originally designed diversity was combinatorially reintroduced into the clone to create a new set of variants. These new sets of variants were then re-screened by panning on EGF and in each successive round the stringency of binding and washing was increased. The net result created pools of EGF binding phage that enriched to greater levels over background than those found in the original panning.

Example 5

Design of a Cytokine Theme Library

In order to create productive libraries for the discovery of new anti-cytokine antibodies, a productive anti-TNF-α antibody, HUMIRA® (adalimumab) was selected as a basic theme. HUMIRA® (adalimumab) is a recombinant human IgG1 monoclonal antibody created using phage display technology resulting in an antibody with human-derived heavy and light chain variable regions and human IgG1:κ constant regions.

Figure 8:
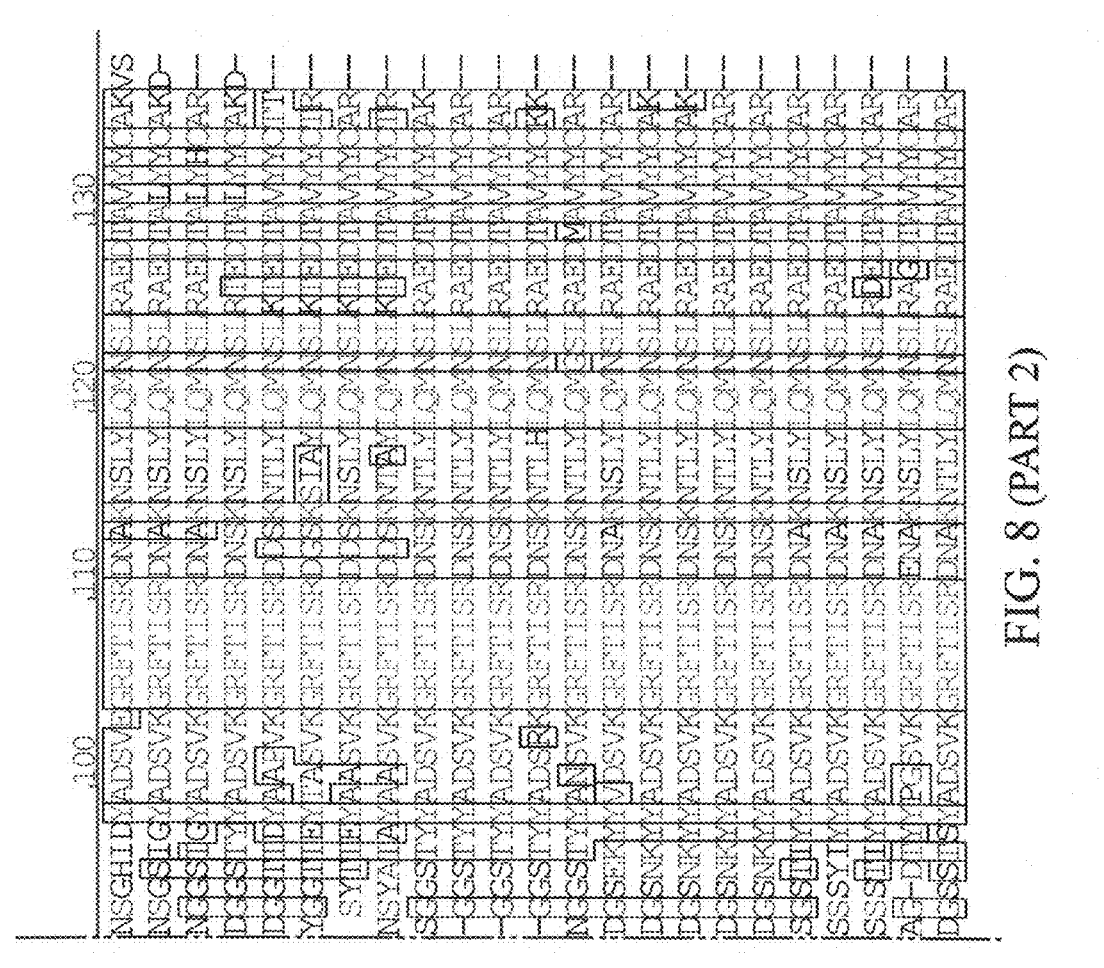
Figure 10:
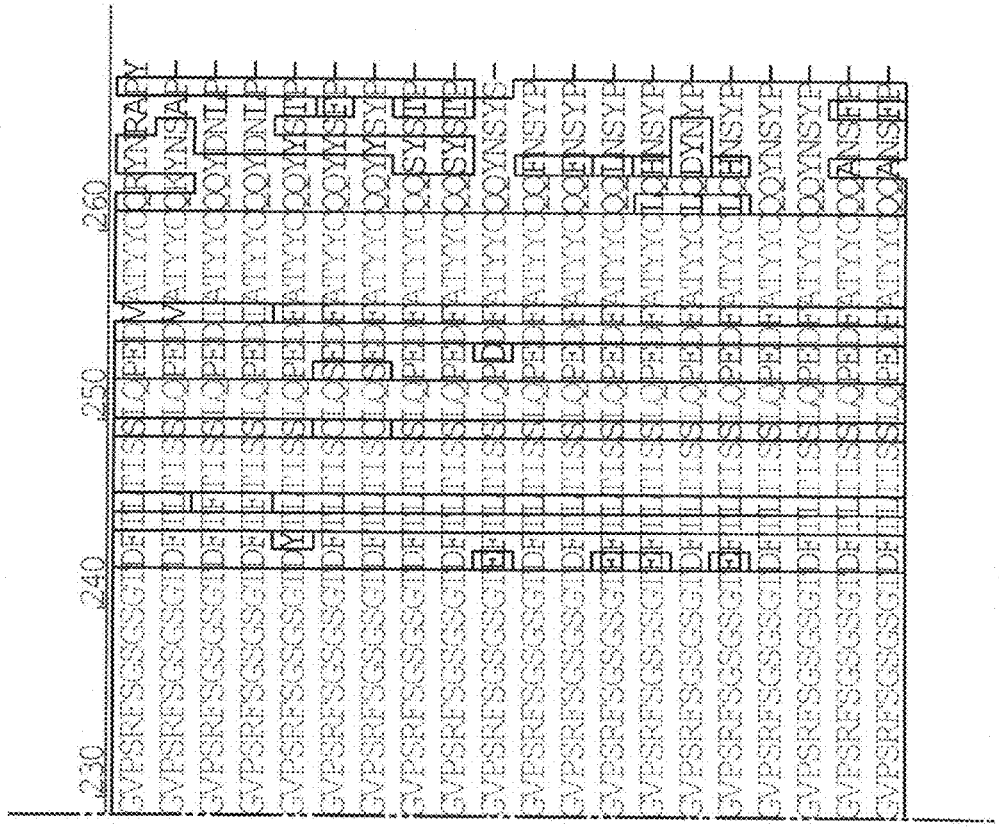
FIG. 10: Determination of germline origin of productive anti-TNF-α antibody light chain. The various light chain sequences (D2E7 through VK1 L5) are represented by SEQ ID NOS: 139 to 159.
Figure 11:
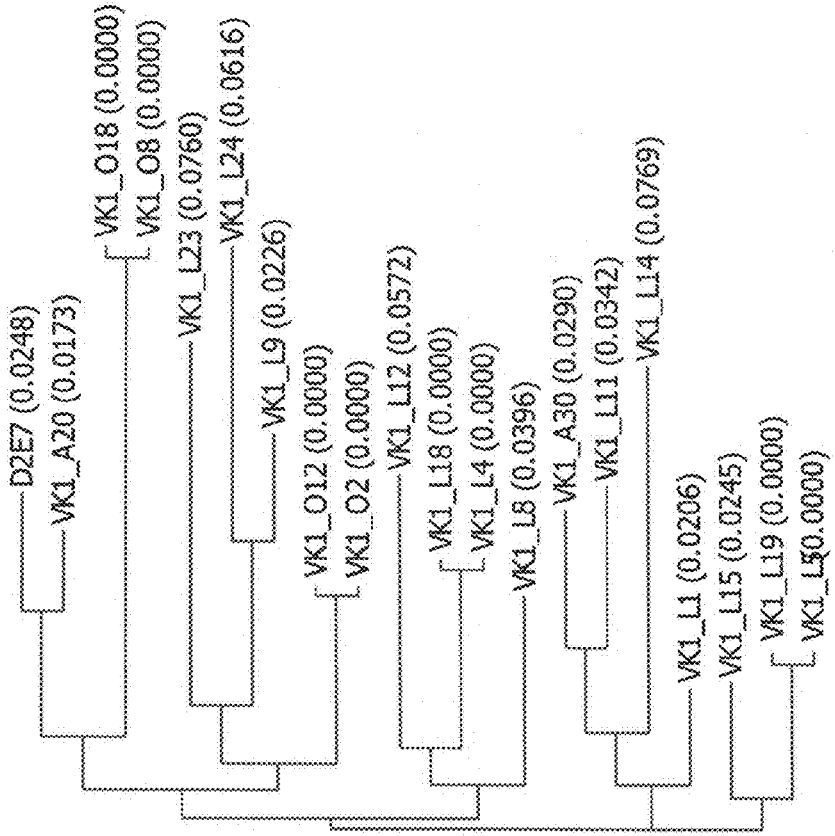
FIG. 11: Dendrogram alignment illustrating the germline origin of productive anti-TNF-α antibody light chain.

To determine the germline origin of the heavy chain of parental antibody D2E7, the framework region was analyzed. This was accomplished by masking the CDRs of D2E7 and of the human germline VH genes. Next the remaining sequences between FR1 and FR3 for D2E7 was aligned by BLAST algorithm against all of the human germline VH genes. As shown in FIG. 8, the D2H7 $V_H$ region showed greatest similarity to $V_H3\_3$-09. The dendogram alignment set forth in FIG. 9 shows the same result. In a similar fashion the light chain of parental antibody D2E7 found to be most similar to $V_\kappa 1$ A20 (FIGS. 10 and 11).

Figure 12:
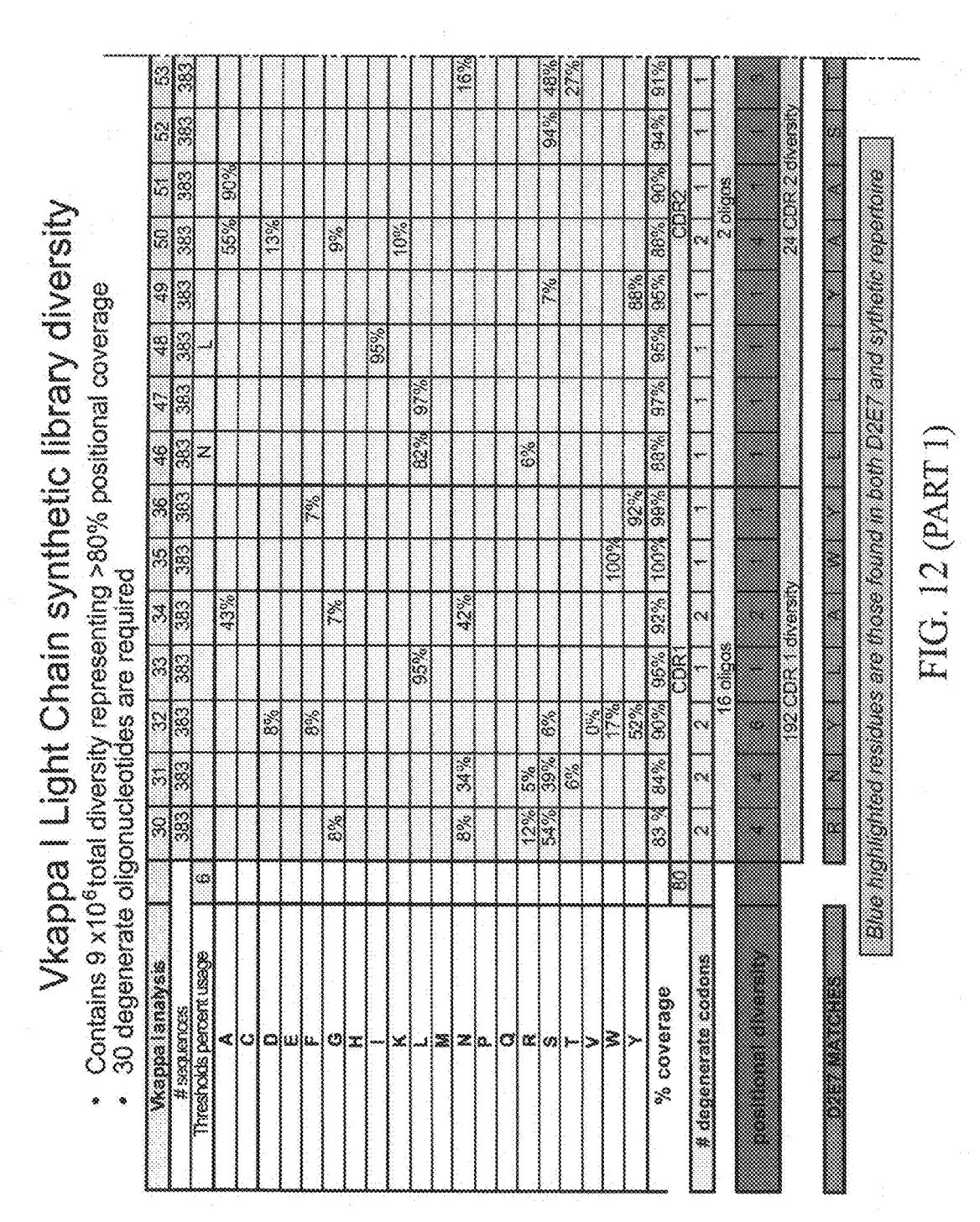

The frequency analysis of antibody light chain $V_\kappa 1$ CDR1, CDR2, and CDR3 sequences described in Example 1 was modified by setting the threshold percent usage filter to 6%. As shown in FIG. 12, with this filter the sum usage for all amino acid positions, except position 91, is over 80%, which accommodates a library diversity of $9 \times 10^6$, and this diversity can be generated by 30 degenerate oligonucleotides.

Next, 5971 human antibody heavy chain variable domain sequences were collected from the Kabat Database of Sequences of Proteins of Immunological Interest. For each sequence, the gene sequence was translated into the corresponding amino acid sequence, and the amino acid sequences were positionally aligned, following the Kabat numbering system.

The heavy chain variable domain collection was then subjected to the following filters:
1. $V_H3$ sequences containing "CAAS" (SEQ ID NO: 3) at amino acid positions 22-25 (1530 of 5971 members);
2. sequences combined with κ light chains, CDR1=6 amino acids and CDR2=13 amino acids (226 of 1530 members);
3. Including only members containing complete sequences from "CAAS" preceding CDR1 through a complete CDR2 sequence (180 of 226 members).

Subsequently, the sequences were aligned, the occurrence amino acids at each position was tabulated, and the distribution of the 20 naturally occurring amino acids at each position was calculated to produce the positional frequency-based database of CDR domain diversity based on absolute usage of amino acids by position. The results of this tabulation are shown in FIG. 13.

The datasets set forth in FIG. 13 were further filtered by reporting only amino acid usage that was at least 10% for any given position. As shown in FIG. 14, using this filter, in CDR2 the sum amino acid coverage at positions 52, 52A, 55, and 58 is less than 75%. To accommodate a greater coverage, the required percent usage has been reduced from 10% to 5%. As shown in FIG. 15, this change has resulted in raising the sum amino acid usage for all positions to greater than 75%.

Applying the 5% usage filter both CDR1 and CDR24 degenerate oligonucleotides required for the synthesis of the CDR1 regions, CDR2 diversity can be encoded by 28 degenerate oligonucleotides (see FIG. 16). Thus, using a total of 28 degenerate oligonucleotides, a total diversity of $1.5 \times 10^8$ can be achieved, providing more than 80% positional coverage.

In the next step, from the 5971 human antibody heavy chain variable domain sequences described above, sequences $V_H3$ sequences 13 amino acids in length were compiled, regardless of isotype. The required percent amino acid usage for each position was set to 4%, except at amino acid positions 93, 94 and 101, where the threshold was set to 4% usage. The results are set forth in FIG. 17. By setting these thresholds, a synthetic $V_H3$ heavy chain synthetic library with a total diversity of $7.5 \times 10^9$ can be prepared by using 384 degenerate oligonucleotides. As shown, residues in the CD3 region shows a good agreement with the corresponding residues in the parent antibody D2E7.

Example 6

Design of a Hapten Themed Antibody Library

The objective of this method is to design productive libraries for the identification of new anti-hapten antibodies.

The design started with an anti-digoxigenin (anti-DIG) antibody (Dorsam, H. et al., FEBS Lett. 414:7-13 (1997)). The Ig λ light chain variable region sequence (SEQ ID NO: 1) and the heavy chain variable region sequence (SEQ ID NO: 2) for this antibody are shown in FIG. 18.

In order to determine the germline origin of the heavy and light chains of this parental antibody were analyzed. As shown in FIG. 19, $V_L$-1 g is most similar to the light chain, and $V_H$ 3-23 is most similar to the heavy chain, therefore, the CDRs were put in this environment in order to create a productive library for identification of anti-hapten antibodies.

Next, the light chain CDR1 and CDR2 sequences were analyzed as described in the previous examples for λ length matched $V_L$ framework residues. The required percent amino acid usage for each position was set to 6%, so that no individual sequences were reported below 6%. As shown in FIG. 20, this filter provide an excellent coverage for each amino acid position. Performing a similar analysis for H3 length matched (8 amino acids) heavy chain, but applying a 6.25% filter, the sum amino acid coverage, including all positions, was above 75% (FIG. 21).

Example 7

Cytokine (IFN-α) Analysis and Library Creation

IFN is a generic term for cytokines having anti-viral activity, among which those produced from leukocytes or lymphoblastic cells by stimulation with virus or double stranded nucleic acids are termed as IFN-α. IFN-α has a variety of activities including anti-viral activity and cellular growthsuppressing activity, which activities have been found to be useful in the treatment of a variety of diseases such as hepatitis type B and type C infections, and cancer. Analysis of sequences of IFN-α genes cloned from a variety of DNA libraries has revealed that IFN-α exists in several subtypes. For example, for the IFN-α2 gene, three additional types (α2a, .α2b, and .α2c) have been identified. Altogether, there are over 20 currently known IFN-α subtypes. Additional known subtypes include, for example, IFN-α1a, IFN-α1b, IFN-α4a, IFN-α4b, IFN-α5, IFN-α6, etc. It has been demonstrated that many of the IFN-α subtypes differ in their biological activities and other biological properties. Therefore, libraries created based upon the existing natural diversity among members of the IFN-α family find utility in generating IFN-α polypeptides with new and improved properties, such as increased potency, decreased immunogenicity, increased half-life, improved proteolytic stability.

As a first step for creating a diverse IFN-α library, eleven 189 amino acids long gene products were identified. Amino acid residues 32-38 of these IFN-α polypeptides were aligned with each other and the residue frequency usage was determined, as shown in FIG. 22. When the threshold percent amino acid usage is set to 9%, 100% coverage can be achieved using 2 degenerate oligonucleotides (see, FIGS. 22 and 23). As shown in FIG. 23, with a non-degenerate design 40 oligonucleotides are needed to provide the required coverage.

Once the library is prepared, screening for desired novel properties can be performed by methods known in the art. Thus, increased potency can be tested in standard biological assays, such as by biopanning a phage-displayed IFN-α library. members with increased half-life can be identified, for example, by biopanning a phage-displayed library against an IFN-α receptor, or by exposing members of the library to one or more serum proteases. Decreased immunogenicity can be tested, for example, by identifying the peptides or polypeptides present in the library that show the least binding to MHC molecules, or by testing T cell epitope presentation of whole proteins directly.

These and numerous additional tests are well known to those of ordinary skill in the pertinent art.

Example 8

Chemically Probed Antibody Collections

The present example shows the creation of CDR3 heavy chain diversity using probe sets designed based on chemical principles.

Figure 24:
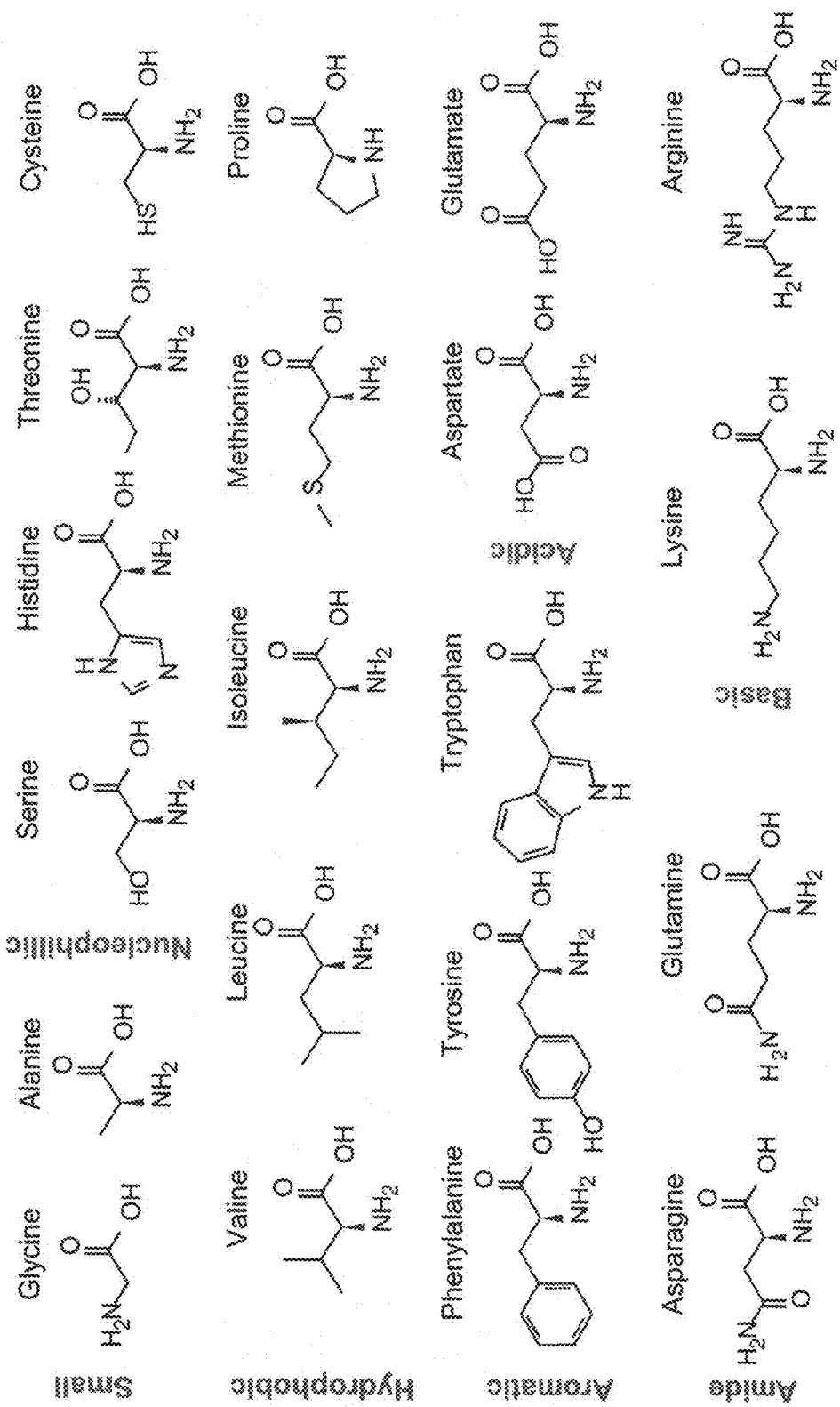
FIG. 24: Amino acids categorized by side-chain chemistries.
Figure 25:
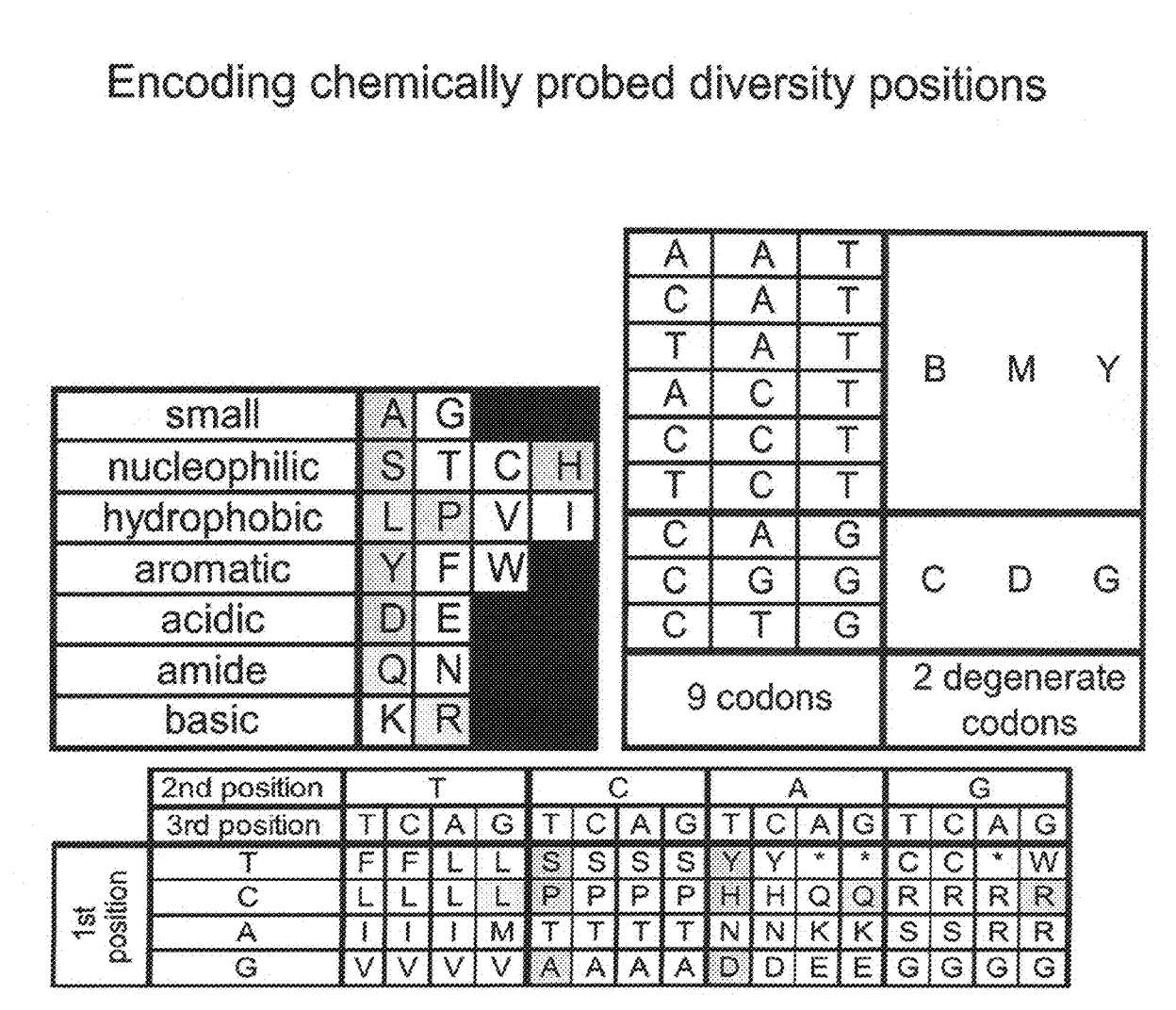

Amino acids can be divided into seven groups, characterized by small, nucleophilic, hydrophobic, aromatic, acidic, amide, and basic side-chain chemical functionalities, respectively (FIG. 24). The top left panel in FIG. 25 shows the one-letter symbols of amino acids present in each of the seven groups. Nine amino acids (A, S, H, L, P, Y, D, Q, R), representative of the different side-chain chemistries, were selected. As shown in the rest of FIG. 25, the highlighted nine amino acids can be encoded, and thus the side-chain chemistry diversity can be captured, by nine codons or 2 degenerate codons. (B=C, G, or T; M=A or C; Y=C or T. D=A, G, or T.)

Figure 26:
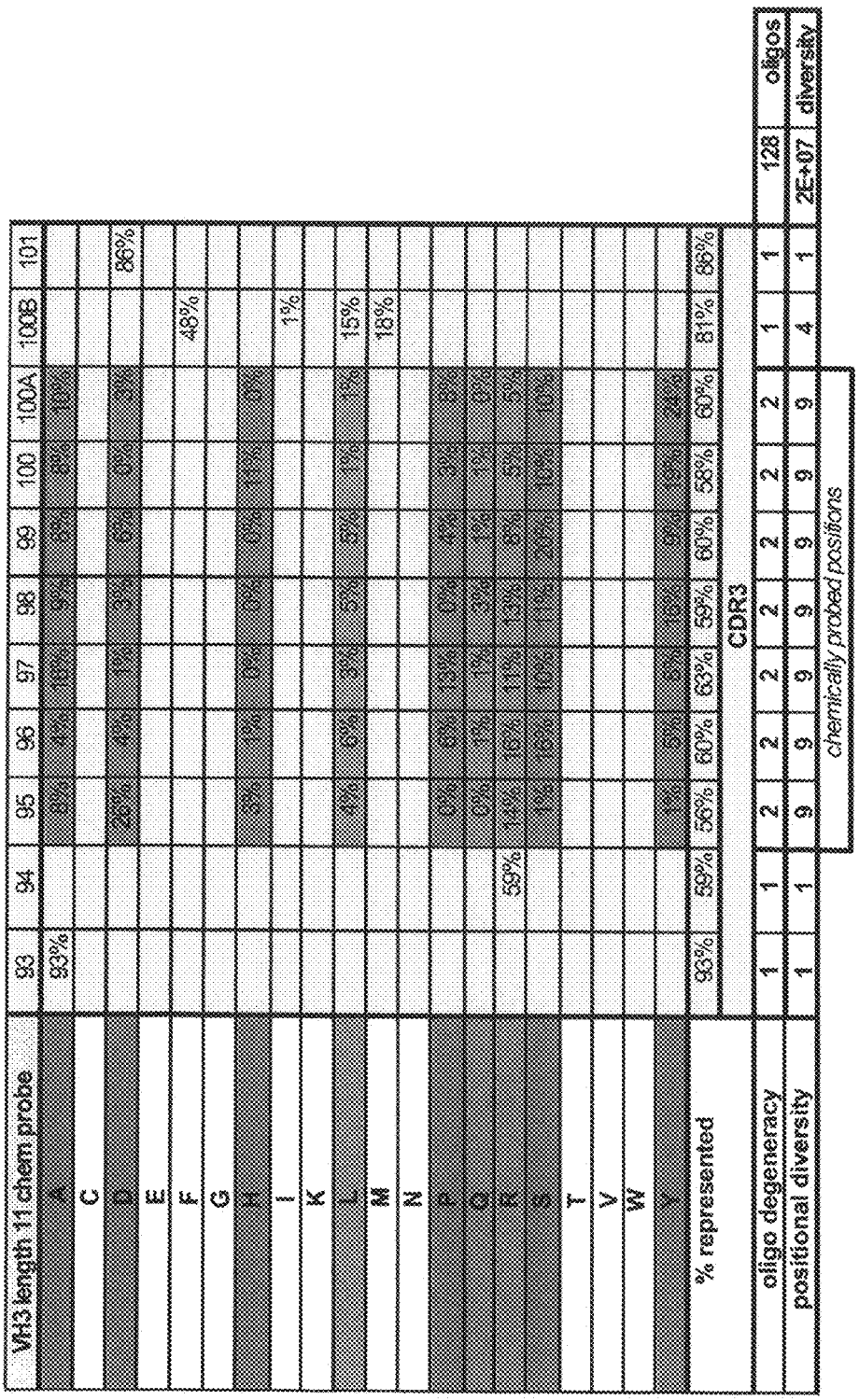
FIG. 26: CDR3 containing chemically probed diversity.
Figure 27:
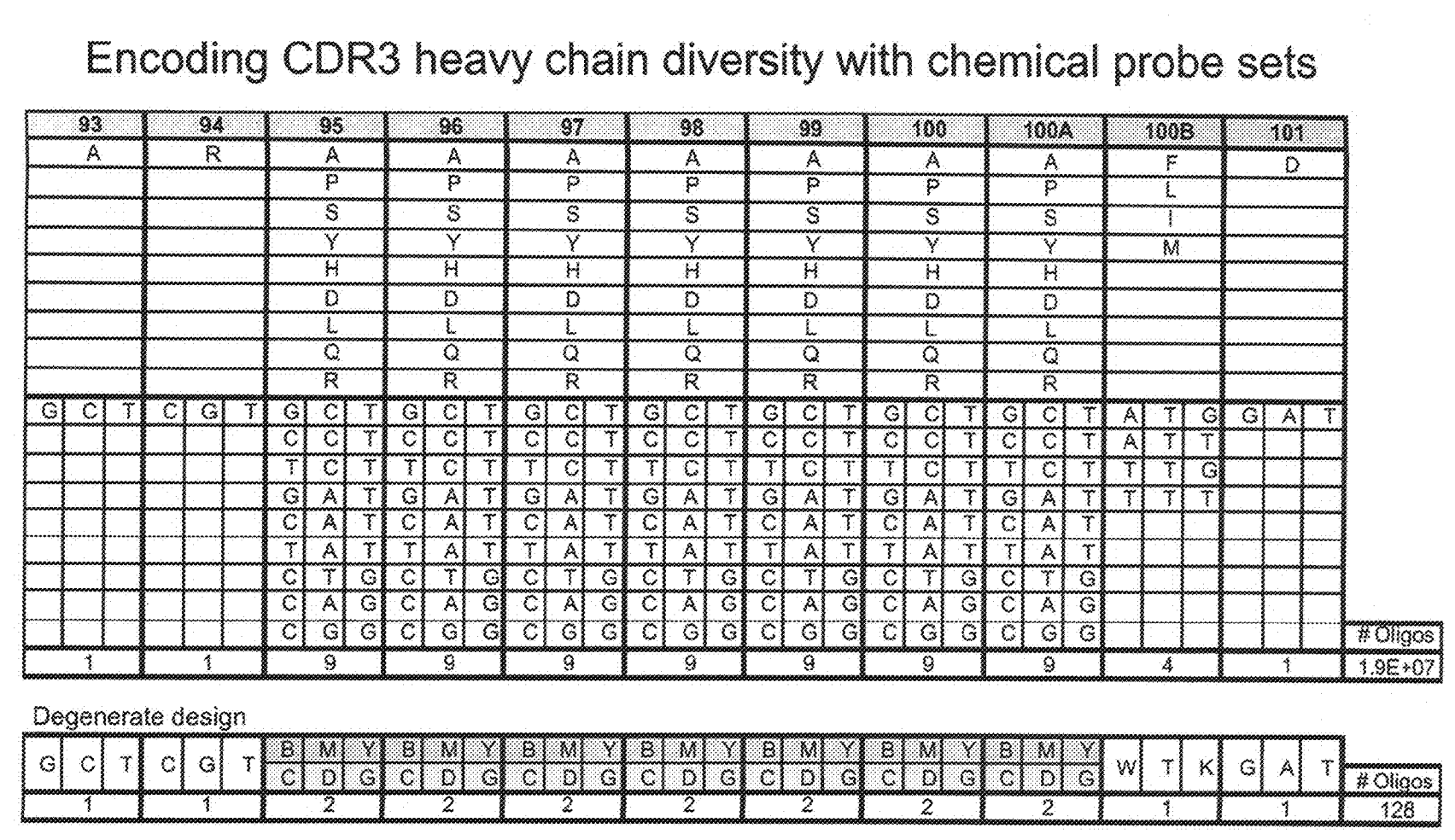

The native heavy chain CDR3 sequence contains a high degree of chemical diversity (around 60% or more). It has been determined that a similar chemical diversity can be generated, by combinatorial denegerate oligonucleotide synthesis, using 128 degenerate oligonucleotides. The design of the corresponding degenerate oligonucleotides is shown in FIG. 27. As set forth in FIG. 26, this approach covers a majority of the naturally occurring diversity and provides broad interactive chemistries.

This chemically probed diversity approach can be used on its own, or in combinations with any of the other methods of the present invention, in order to produce combinatorial libraries with desired properties.

Although in the foregoing description the invention is illustrated with reference to certain embodiments, it is not so limited. Indeed, various modifications of the invention in addition to those shown and described herein will become apparent to those skilled in the art from the foregoing description and fall within the scope of the appended claims. Thus, while the invention is illustrated with reference to antibody libraries, it extends generally to all peptide and polypeptide libraries.

All references cited throughout the specification are hereby expressly incorporated by reference.

The invention claimed is:

1. A computer-implemented method for diversity analysis of a database comprising related amino acid sequences characterized by at least one shared sequence motif and synthesis of a polypeptide library based on said analysis, comprising the steps of:
   (a) aligning said related amino acid sequences;
   (b) generating a first dataset representing a subset of the related amino acid sequences by applying to said amino acid sequences a predetermined combination of two or more filters based on parameters of the amino acid sequences;
   (c) analyzing said first dataset for positional amino acid usage frequency within said shared sequence motif;
   (d) generating a second dataset that models positional amino acid diversity within the shared sequence motif for amino acid sequences characterized by said predetermined combination of filters, by applying a minimum threshold amino acid usage frequency to the positional amino acid usage frequency obtained in step (c) at one or more amino acid positions within said shared sequence motif
   (e) synthesizing a physical library of related amino acid sequences that is designed with the aid of the second dataset,
   characterized in that:
   synthesis of the physical library comprises synthesizing a collection of degenerate oligonucleotide sequences that physically represent the combinatorial positional amino acid diversity of the second dataset and cloning the oligonucleotide sequences into a suitable template.

2. The method of claim 1 wherein said related amino acid sequences comprise antibody heavy or light chain sequences.

3. The method of claim 2 wherein said shared sequence motif is a CDR sequence selected from the group consisting of CDR1, CDR2 and CDR3 sequences.

4. The method of claim 3 wherein in step (b) said predetermined combination of filters is selected from the group consisting of (1) the isotype of said antibody heavy or light chain; (2) the length of one or more of said CDR1, CDR2 and CDR3 sequences; (3) the presence of one or more predetermined amino acid residues at one or more predetermined positions within one or more of said CDR1, CDR2 and CDR3 sequences; (4) type of framework; (5) antigen to which said antibody binds; (6) affinity of said antibody; and (7) positional amino acid residues outside said CDR sequences.

5. The method of claim 4 wherein at least one of the antibody heavy and/or light chain CDR1, CDR2 and CDR3 sequences is size matched.

6. The method of claim 5 wherein an additional filter is the isotype of said antibody heavy and/or light chain sequences.

7. The method of claim 3 wherein said positional amino acid usage frequency is between at least about 3% and at least about 15%.

8. The method of claim 3 wherein the same positional amino acid usage frequency characterizes each amino acid within said CDR sequence.

9. The method of claim 3 wherein the positional amino acid usage frequencies differ at least two amino acid residues within said CDR sequence.

10. The method of claim 4 wherein said predetermined combination of filters includes the type of framework.

11. The method of claim 2 wherein both antibody heavy and light chain sequences are analyzed, and the antibody heavy chain sequences are paired to predetermined antibody light chain characteristics, or the antibody light chain sequences are paired to predetermined antibody heavy chain characteristics.

12. The method of claim 2 wherein said related antibody sequences are from at least one functional antibody.

13. The method of claim 12 wherein one of said filters applied in step (b) is the germline sequence most similar to the framework sequence of the heavy and/or light chain of said functional antibody.

14. The method of claim 12 wherein said functional antibody binds to a polypeptide selected from the group consisting of cell surface and soluble receptors, cytokines, growth factors, enzymes; proteases; and hormones.

15. The method of claim 2 wherein in step (d) a minimum threshold amino acid usage frequency is assigned to at least the majority of amino acid positions within said shared sequence motif.

16. The method of claim 2 wherein said minimum threshold amino acid usage frequency is set to provide a minimum sum amino acid usage for the majority of amino acid positions within said shared sequence motif.

17. The method of claim 16 wherein said minimum threshold amino acid usage frequency is set to provide a minimum sum amino acid usage for all amino acid positions within said shared sequence motif.

18. The method of claim 17 wherein said minimum sum amino acid usage is between at least about 60% and at least about 90%.

* * * * *

SEQUENCE LISTING

```
<160> NUMBER OF SEQ ID NOS: 176

<210> SEQ ID NO 1
<211> LENGTH: 111
<212> TYPE: PRT
<213> ORGANISM: Homo sapiens

<400> SEQUENCE: 1

Ser Tyr Glu Leu Thr Gln Pro Pro Ser Ala Ser Gly Thr Pro Gly Gln
1               5                   10                  15

Arg Val Thr Ile Ser Cys Ser Gly Ser Thr Ser Asn Ile Gly Ser Asn
            20                  25                  30

Tyr Val Tyr Trp Tyr Gln His Leu Pro Gly Thr Ala Pro Lys Leu Leu
        35                  40                  45

Ile Phe Arg Asn Ser Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80
```

```
Ser Glu Asp Glu Ala Asp Tyr Tyr Cys Ala Ala Trp Asp Asp Ser Leu
                85                  90                  95

Ser Gly Val Val Phe Gly Gly Gly Thr Lys Leu Thr Val Leu Gly
        100                 105                 110
```

<210> SEQ ID NO 2
<211> LENGTH: 116
<212> TYPE: PRT
<213> ORGANISM: Homo sapiens

<400> SEQUENCE: 2

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Lys Gly Ser Gly Trp Tyr Trp Gly Gln Gly Thr Leu Val
            100                 105                 110

Thr Val Ser Ser
        115
```

<210> SEQ ID NO 3
<211> LENGTH: 4
<212> TYPE: PRT
<213> ORGANISM: Homo sapiens

<400> SEQUENCE: 3

```
Cys Ala Ala Ser
1
```

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
vrtmvttdkc tcrymtggtc t                                            21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
sgtamttgkc tcgcatggtc t                                            21

<210> SEQ ID NO 6
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 6
artamttgkc tcgcatggtc t                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
sgtmgttgkc tcgcatggtc t                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
artmgttgkc tcgcatggtc t                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
sgtamttwtc tcgcatggtc t                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
artamttwtc tcgcatggtc t                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
sgtmgttwtc tcgcatggtc t                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
                              oligonucleotide

<400> SEQUENCE: 12
artmgttwtc tcgcatggtc t                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
sgtamttgkc tcatctggtc t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
artamttgkc tcatctggtc t                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
sgtmgttgkc tcatctggtc t                                              21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
artmgttgkc tcatctggtc t                                              21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
sgtamttwtc tcatctggtc t                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 18
artamttwtc tcatctggtc t                                               21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
sgtmgttwtc tcatctggtc t                                               21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
artmgttwtc tcatctggtc t                                               21

<210> SEQ ID NO 21
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
accgcagttt actattgcgc acgtvtgskt aagkmtbrtg stwtkgatta ctggggtcag     60
ggcac                                                                 65

<210> SEQ ID NO 22
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
accgcagttt actattgcgc aaagvtgskt aagkmtbrtg stwtkgatta ctggggtcag     60
ggcac                                                                 65

<210> SEQ ID NO 23
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
accgcagttt actattgcgc acgtgrwskt aagkmtbrtg stwtkgatta ctggggtcag     60
ggcac                                                                 65

<210> SEQ ID NO 24
<211> LENGTH: 65
<212> TYPE: DNA
<213> ORGANISM: Artificial Sequence
```

-continued

<220> FEATURE:
<223> OTHER INFORMATION: Description of Artificial Sequence: Synthetic
      oligonucleotide

<400> SEQUENCE: 24
accgcagttt actattgcgc aaaggrwskt aagkmtbrtg stwtkgatta ctggggtcag    60
ggcac                                                                65

<210> SEQ ID NO 25
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
accgcagttt actattgcgc acgtvtggmt aagkmtbrtg stwtkgatta ctggggtcag    60
ggcac                                                                65

<210> SEQ ID NO 26
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
accgcagttt actattgcgc aaagvtggmt aagkmtbrtg stwtkgatta ctggggtcag    60
ggcac                                                                65

<210> SEQ ID NO 27
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
accgcagttt actattgcgc acgtgrwgmt aagkmtbrtg stwtkgatta ctggggtcag    60
ggcac                                                                65

<210> SEQ ID NO 28
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
accgcagttt actattgcgc aaaggrwgmt aagkmtbrtg stwtkgatta ctggggtcag    60
ggcac                                                                65

<210> SEQ ID NO 29
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
accgcagttt actattgcgc acgtvtgskt gdtkmtbrtg stwtkgatta ctggggtcag    60
ggcac    65

<210> SEQ ID NO 30
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
accgcagttt actattgcgc aaagvtgskt gdtkmtbrtg stwtkgatta ctggggtcag    60
ggcac    65

<210> SEQ ID NO 31
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
accgcagttt actattgcgc acgtgrwskt gdtkmtbrtg stwtkgatta ctggggtcag    60
ggcac    65

<210> SEQ ID NO 32
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
accgcagttt actattgcgc aaaggrwskt gdtkmtbrtg stwtkgatta ctggggtcag    60
ggcac    65

<210> SEQ ID NO 33
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
accgcagttt actattgcgc acgtvtggmt gdtkmtbrtg stwtkgatta ctggggtcag    60
ggcac    65

<210> SEQ ID NO 34
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
accgcagttt actattgcgc aaagvtggmt gdtkmtbrtg stwtkgatta ctggggtcag    60
ggcac    65

<210> SEQ ID NO 35
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
accgcagttt actattgcgc acgtgrwgmt gdtkmtbrtg stwtkgatta ctggggtcag      60
ggcac                                                                  65

<210> SEQ ID NO 36
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
accgcagttt actattgcgc aaaggrwgmt gdtkmtbrtg stwtkgatta ctggggtcag      60
ggcac                                                                  65

<210> SEQ ID NO 37
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, g, t, unknown or other

<400> SEQUENCE: 37
accgcagttt actattgcgc acgtvtgskt cntkmtbrtg stwtkgatta ctggggtcag      60
ggcac                                                                  65

<210> SEQ ID NO 38
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, g, t, unknown or other

<400> SEQUENCE: 38
accgcagttt actattgcgc aaagvtgskt cntkmtbrtg stwtkgatta ctggggtcag      60
ggcac                                                                  65

<210> SEQ ID NO 39
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, g, t, unknown or other

<400> SEQUENCE: 39
accgcagttt actattgcgc acgtgrwskt cntkmtbrtg stwtkgatta ctggggtcag    60
ggcac    65

<210> SEQ ID NO 40
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, g, t, unknown or other

<400> SEQUENCE: 40
accgcagttt actattgcgc aaaggrwskt cntkmtbrtg stwtkgatta ctggggtcag    60
ggcac    65

<210> SEQ ID NO 41
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, g, t, unknown or other

<400> SEQUENCE: 41
accgcagttt actattgcgc acgtvtggmt cntkmtbrtg stwtkgatta ctggggtcag    60
ggcac    65

<210> SEQ ID NO 42
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, g, t, unknown or other

<400> SEQUENCE: 42
accgcagttt actattgcgc aaagvtggmt cntkmtbrtg stwtkgatta ctggggtcag    60
ggcac    65

<210> SEQ ID NO 43
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, g, t, unknown or other

<400> SEQUENCE: 43
accgcagttt actattgcgc acgtgrwgmt cntkmtbrtg stwtkgatta ctggggtcag    60
ggcac                                                                65

<210> SEQ ID NO 44
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, g, t, unknown or other

<400> SEQUENCE: 44
accgcagttt actattgcgc aaaggrwgmt cntkmtbrtg stwtkgatta ctggggtcag     60
ggcac                                                                65

<210> SEQ ID NO 45
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
accgcagttt actattgcgc acgtvtgskt aagsgtbrtg stwtkgatta ctggggtcag     60
ggcac                                                                65

<210> SEQ ID NO 46
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
accgcagttt actagtgcgc aaagvtgskt aagsgtbrtg stwtkgatta ctggggtcag     60
ggcac                                                                65

<210> SEQ ID NO 47
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
accgcagttt actattgcgc acgtgrwskt aagsgtbrtg stwtkgatta ctggggtcag     60
ggcac                                                                65

<210> SEQ ID NO 48
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
accgcagttt actattgcgc aaaggrwskt aagsgtbrtg stwtkgatta ctggggtcag     60
ggcac                                                               65

<210> SEQ ID NO 49
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
accgcagttt actattgcgc acgtvtggmt aagsgtbrtg stwtkgatta ctggggtcag   60
ggcac                                                               65

<210> SEQ ID NO 50
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
accgcagttt actattgcgc aaagvtggmt aagsgtbrtg stwtkgatta ctggggtcag   60
ggcac                                                               65

<210> SEQ ID NO 51
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
accgcagttt actattgcgc acgtgrwgmt aagsgtbrtg stwtkgatta ctggggtcag   60
ggcac                                                               65

<210> SEQ ID NO 52
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
accgcagttt actattgcgc aaaggrwgmt aagsgtbrtg stwtkgatta ctggggtcag   60
ggcac                                                               65

<210> SEQ ID NO 53
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
accgcagttt actattgcgc acgtvtgskt gdtsgtbrtg stwtkgatta ctggggtcag   60
ggcac                                                               65

<210> SEQ ID NO 54
<211> LENGTH: 65

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
accgcagttt actattgcgc aaagvtgskt gstsgtbrtg stwtkgatta ctggggtcag    60
ggcac    65

<210> SEQ ID NO 55
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
accgcagttt actattgcgc acgtgrwskt gdtsgtbrtg stwtkgatta ctggggtcag    60
ggcac    65

<210> SEQ ID NO 56
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
accgcagttt actattgcgc aaaggrwskt gdtsgtbrtg stwtkgatta ctggggtcag    60
ggcac    65

<210> SEQ ID NO 57
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
accgcagttt actattgcgc acgtvtggmt gdtsgtbrtg stwtkgatta ctggggtcag    60
ggcac    65

<210> SEQ ID NO 58
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
accgcagttt actattgcgc aaagvtggmt gdtsgtbrtg stwtkgatta ctggggtcag    60
ggcac    65

<210> SEQ ID NO 59
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 59
accgcagttt actattgctc acgtgrwgmt gdtsgtbrtg stwtkgatta ctggggtcag      60
ggcac                                                                  65

<210> SEQ ID NO 60
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
accgcagttt actattgcgc aaaggrwgmt gdtsgtbrtg stwtkgatta ctggggtcag      60
ggcac                                                                  65

<210> SEQ ID NO 61
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, g, t, unknown or other

<400> SEQUENCE: 61
accgcagttt actattgcgc acgtvtgskt cntsgtbrtg stwtkgatta ctggggtcag      60
ggcac                                                                  65

<210> SEQ ID NO 62
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, g, t, unknown or other

<400> SEQUENCE: 62
accgcagttt actattgcgc aaagvtgskt cntsgrbrtg stwtkgatta ctggggtcag      60
ggcac                                                                  65

<210> SEQ ID NO 63
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, g, t, unknown or other

<400> SEQUENCE: 63
accgcagttt actattgcgc acgtgrwskt cntsgtbrtg stwtkgatta ctggggtcag      60
ggcac                                                                  65
```

```
<210> SEQ ID NO 64
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, g, t, unknown or other

<400> SEQUENCE: 64
accgcagttt actattgcgc aaaggrwskt cntsgtbrtg stwtkgatta ctggggtcag      60
ggcac                                                                 65

<210> SEQ ID NO 65
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, g, t, unknown or other

<400> SEQUENCE: 65
accgcagttt actattgcgc acgtvtggmt cntsgtbrtg stwtkgatta ctggggtcag      60
ggcac                                                                 65

<210> SEQ ID NO 66
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, g, t, unknown or other

<400> SEQUENCE: 66
accgcgttta ctattgcgca aagctgggmt cntsgtbrtg stwtkgatta ctggggtcag      60
ggcac                                                                 65

<210> SEQ ID NO 67
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, g, t, unknown or other

<400> SEQUENCE: 67
accgcagttt actattgcgc acgtgrwgmt cntsgtbrtg stwtkgatta ctggggtcag      60
ggcac                                                                 65

<210> SEQ ID NO 68
<211> LENGTH: 65
<212> TYPE: DNA
<213> ORGANISM: Artificial Sequence
```

<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, g, t, unknown or other

<400> SEQUENCE: 68
accgcagttt actattgcgc aaaggrwgmt cntsgtbrtg stwtkgatta ctggggtcag    60
ggcac                                                                65

<210> SEQ ID NO 69
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
accgcagttt actattgcgc acgtvtgskt aagkmtbrtt mtwtkgatta ctggggtcag    60
ggcac                                                                65

<210> SEQ ID NO 70
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
accgcagttt actattgcgc aaagvtgskt aagkmtbrtt mtwtkgatta ctggggtcag    60
ggcac                                                                65

<210> SEQ ID NO 71
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
accgcagttt actattgcgc acgtgrwskt aagkmtbrtt mtwtkgatta ctggggtcag    60
ggcac                                                                65

<210> SEQ ID NO 72
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
accgcagttt actattgcgc aaaggrwskt aagkmtbrtt mtwtkgatta ctggggtcag    60
ggcac                                                                65

<210> SEQ ID NO 73
<211> LENGTH: 65
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 73
accgcagttt actattgcgc acgtvtggmt aagkmtbrtt mtwtkgatta ctggggtcag    60
ggcac                                                                65

<210> SEQ ID NO 74
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
accgcagttt actattgcgc aaagvtggmt aagkmtbrtt mtwtkgatta ctggggtcag    60
ggcac                                                                65

<210> SEQ ID NO 75
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
accgcagttt actattgcgc acgtgrwgmt aagkmtbrtt mtwtkgatta ctggggtcag    60
ggcac                                                                65

<210> SEQ ID NO 76
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
accgcagttt actattgcgc aaaggrwgmt aagkmtbrtt mtwtkgatta ctggggtcag    60
ggcac                                                                65

<210> SEQ ID NO 77
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
accgcagttt actattgcgc acgtvtgskt gdtkmtbrtt mtwtkgatta ctggggtcag    60
ggcac                                                                65

<210> SEQ ID NO 78
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
```

```
accgcagttt actattgcgc aaagvtgskt gdtkmtbrtt mtwtkgatta ctggggtcag      60
ggcac                                                                  65
```

<210> SEQ ID NO 79
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79

```
accgcagttt actattgcgc acgtgrwskt gdtkmtbrtt mtwtkgatta ctggggtcag      60
ggcac                                                                  65
```

<210> SEQ ID NO 80
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80

```
accgcagttt actattgcgc aaaggrwskt gdtkmtbrtt mtwtkgatta ctggggtcag      60
ggcac                                                                  65
```

<210> SEQ ID NO 81
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81

```
accgcagttt actattgcgc acgtvtggmt gdtkmtbrtt mtwtkgatta ctggggtcag      60
ggcac                                                                  65
```

<210> SEQ ID NO 82
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82

```
accgcagttt actattgcgc aaagvtggmt gdtkmtbrtt mtwtkgatta ctggggtcag      60
ggcac                                                                  65
```

<210> SEQ ID NO 83
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83

```
accgcagttt actattgcgc acgtgrwgmt gdtkmtbrtt mtwtkgatta ctggggtcag      60
ggcac                                                                  65
```

```
<210> SEQ ID NO 84
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
accgcagttt actattgcgc aaaggrwgmt gdtkmtbrtt mtwtkgatta ctggggtcag    60
ggcac                                                                65

<210> SEQ ID NO 85
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, g, t, unknown or other

<400> SEQUENCE: 85
accgcagttt actattgcgc acgtvtgskt cntkmtbrtt mtwtkgatta ctggggtcag    60
ggcac                                                                65

<210> SEQ ID NO 86
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, g, t, unknown or other

<400> SEQUENCE: 86
accgcagttt actattgcgc aaagvtgskt cntkmtbrtt mtwtkgatta ctggggtcag    60
ggcac                                                                65

<210> SEQ ID NO 87
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, g, t, unknown or other

<400> SEQUENCE: 87
accgcagttt actattgcgc acgtgrwskt cntkmtbrtt mtwtkgatta ctggggtcag    60
ggcac                                                                65

<210> SEQ ID NO 88
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (32)..(32)
<223> OTHER INFORMATION: a, c, g, t, unknown or other

<400> SEQUENCE: 88
accgcagttt actattgcgc aaaggrwskt cntkmtbrtt mtwtkgatta ctggggtcag    60
ggcac                                                                65

<210> SEQ ID NO 89
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, g, t, unknown or other

<400> SEQUENCE: 89
accgcagttt actattgcgc acgtvtggmt cntkmtbrtt mtwtkgatta ctggggtcag    60
ggcac                                                                65

<210> SEQ ID NO 90
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, g, t, unknown or other

<400> SEQUENCE: 90
accgcagttt actattgcgc aaagvtggmt cntkmtbrtt mtwtkgatta ctggggtcag    60
ggcac                                                                65

<210> SEQ ID NO 91
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, g, t, unknown or other

<400> SEQUENCE: 91
accgcagttt actattgcgc acgtgrwgmt cntkmtbrtt mtwtkgatta ctggggtcag    60
ggcac                                                                65

<210> SEQ ID NO 92
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, g, t, unknown or other
```

```
<400> SEQUENCE: 92
accgcagttt actattgcgc aaaggrwgmt cntkmtbrtt mtwtkgatta ctggggtcag    60
ggcac                                                                65

<210> SEQ ID NO 93
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
accgcagttt actattgcgc acgtvtgskt aagsgtbrtt mtwtkgatta ctggggtcag    60
ggcac                                                                65

<210> SEQ ID NO 94
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
accgcagttt actattgcgc aaagvtgskt aagsgtbrtt mtwtkgatta ctggggtcag    60
ggcac                                                                65

<210> SEQ ID NO 95
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
accgcagttt actattgcgc acgtgrwskt aagsgtbrtt mtwtkgatta ctggggtcag    60
ggcac                                                                65

<210> SEQ ID NO 96
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
accgcagttt actattgcgc aaaggrwskt aagsgtbrtt mtwtkgatta ctggggtcag    60
ggcac                                                                65

<210> SEQ ID NO 97
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
accgcagttt actattgcgc acgtvtggmt aagsgtbrtt mtwtkgatta ctggggtcag    60
ggcac                                                                65
```

-continued

<210> SEQ ID NO 98
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
accgcagttt actattgcgc aaagvtggmt aagsgtbrtt mtwtkgatta ctggggtcag      60
ggcac                                                                 65

<210> SEQ ID NO 99
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
accgcagttt actattgcgc acgtgrwgmt aagsgtbrtt mtwtkgatta ctggggtcag      60
ggcac                                                                 65

<210> SEQ ID NO 100
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
accgcagttt actattgcgc aaaggrwgmt aagsgtbrtt mtwtkgatta ctggggtcag      60
ggcac                                                                 65

<210> SEQ ID NO 101
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
accgcagttt actattgcgc acgtvtgskt gdtsgtbrtt mtwtkgatta ctggggtcag      60
ggcac                                                                 65

<210> SEQ ID NO 102
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
accgcagttt actattgcgc aaagvtgskt gdtsgtbrtt mtwtkgatta ctggggtcag      60
ggcac                                                                 65

<210> SEQ ID NO 103
<211> LENGTH: 65
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 103
accgcagttt actattgcgc acgtgrwskt gdtsgtbrtt mtwtkgatta ctggggtcag        60
ggcac                                                                   65

<210> SEQ ID NO 104
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
accgcagttt actattgcgc aaaggrwskt gdtsgtbrtt mtwtkgatta ctggggtcag        60
ggcac                                                                   65

<210> SEQ ID NO 105
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
accgcagttt actattgcgc acgtvtggmt gdtsgtbrtt mtwtkgatta ctggggtcag        60
ggcac                                                                   65

<210> SEQ ID NO 106
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
accgcagttt actattgcgc aaagvtggmt gdtsgtbrtt mtwtkgatta ctggggtcag        60
ggcac                                                                   65

<210> SEQ ID NO 107
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
accgcagttt actattgcgc acgtgrwgmt gdtsgtbrtt mtwtkgatta ctggggtcag        60
ggcac                                                                   65

<210> SEQ ID NO 108
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 108
accgcagttt actattgcgc aaaggrwgmt gdtsgtbrtt mtwtkgatta ctggggtcag      60
ggcac                                                                 65

<210> SEQ ID NO 109
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, g, t, unknown or other

<400> SEQUENCE: 109
accgcagttt actattgcgc acgtvtgskt cntsgtbrtt mtwtkgatta ctggggtcag      60
ggcac                                                                 65

<210> SEQ ID NO 110
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, g, t, unknown or other

<400> SEQUENCE: 110
accgcagttt actattgcgc aaagvtgskt cntsgrbrtt mtwtkgatta ctggggtcag      60
ggcac                                                                 65

<210> SEQ ID NO 111
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, g, t, unknown or other

<400> SEQUENCE: 111
accgcagttt actattgcgc acgtgrwskt cntsgtbrtt mtwtkgatta ctggggtcag      60
ggcac                                                                 65

<210> SEQ ID NO 112
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, g, t, unknown or other

<400> SEQUENCE: 112
accgcagttt actattgcgc aaaggrwskt cntsgtbrtt mtwtkgatta ctggggtcag      60
``` ggcac                                                              65

<210> SEQ ID NO 113
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, g, t, unknown or other

<400> SEQUENCE: 113
accgcagttt actattgcgc acgtvtggmt cntsgtbrtt mtwtkgatta ctggggtcag    60
ggcac                                                              65

<210> SEQ ID NO 114
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, g, t, unknown or other

<400> SEQUENCE: 114
accgcagttt actattgcgc aaagvtggmt cntsgtbrtt mtwtkgatta ctggggtcag    60
ggcac                                                              65

<210> SEQ ID NO 115
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, g, t, unknown or other

<400> SEQUENCE: 115
accgcagttt actattgcgc acgtgrwgmt cntsgtbrtt mtwtkgatta ctggggtcag    60
ggcac                                                              65

<210> SEQ ID NO 116
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, g, t, unknown or other

<400> SEQUENCE: 116
accgcagttt actattgcgc aaaggrwgmt cntsgtbrtt mtwtkgatta ctggggtcag    60
ggcac                                                              65

<210> SEQ ID NO 117

<211> LENGTH: 104
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 117

Pro Ala Met Ala Glu Val Gln Leu Val Glu Ser Gly Gly Gly Leu Val
1               5                   10                  15

Gln Pro Gly Arg Ser Leu Arg Leu Ser Cys Ala Ala Ser Gly Phe Thr
                20                  25                  30

Phe Asp Asp Tyr Ala Met His Trp Val Arg Gln Ala Pro Gly Lys Gly
            35                  40                  45

Leu Glu Trp Val Ser Ala Ile Thr Trp Asn Ser Gly His Ile Asp Tyr
        50                  55                  60

Ala Asp Ser Val Glu Gly Arg Phe Thr Ile Ser Arg Asp Asn Ala Lys
65                  70                  75                  80

Asn Ser Leu Tyr Leu Gln Met Asn Ser Leu Arg Ala Glu Asp Thr Ala
                85                  90                  95

Val Tyr Tyr Cys Ala Lys Val Ser
            100

<210> SEQ ID NO 118
<211> LENGTH: 99
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 118

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp

<210> SEQ ID NO 119
<211> LENGTH: 98
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 119

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
                20                  25                  30

Gly Met Ser Trp Val Arg Gln Ala Pro Gly Lys Gly Leu Glu Trp Val
            35                  40                  45

```
Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr His Cys
                85                  90                  95

Ala Arg

<210> SEQ ID NO 120
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Glu Val Gln Leu Val Glu Ser Gly Gly Val Val Gln Pro Gly Gly
 1               5                  10                  15

Ser Leu Arg Leu Ser Cys Ala Ala Ser Gly Phe Thr Phe Asp Asp Tyr
                20                  25                  30

Thr Met His Trp Val Arg Gln Ala Pro Gly Lys Gly Leu Glu Trp Val
                35                  40                  45

Ser Leu Ile Ser Trp Asp Gly Ser Thr Tyr Tyr Ala Asp Ser Val
    50                  55                  60

Lys Gly Arg Phe Thr Ile Ser Arg Asp Asn Ser Lys Asn Ser Leu Tyr
 65                  70                  75                  80

Leu Gln Met Asn Ser Leu Arg Thr Glu Asp Thr Ala Leu Tyr Tyr Cys
                85                  90                  95

Ala Lys Asp

<210> SEQ ID NO 121
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
                20                  25                  30

Trp Met Ser Trp Val Arg Gln Ala Pro Gly Lys Gly Leu Glu Trp Val
                35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                85                  90                  95

Tyr Cys Thr Thr
            100

<210> SEQ ID NO 122
<211> LENGTH: 100
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 122

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Tyr Thr Ala
    50                  55                  60

Ser Val Lys Gly Arg Phe Thr Ile Ser Arg Asp Gly Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Arg
            100

<210> SEQ ID NO 123
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

Gly Arg Thr Arg Asn Lys Ala Ser Tyr Thr Thr Glu Tyr Ala Ala Ser
    50                  55                  60

Val Lys Gly Arg Phe Thr Ile Ser Arg Asp Asp Ser Lys Asn Ser Leu
65                  70                  75                  80

Tyr Leu Gln Met Asn Ser Leu Lys Thr Glu Asp Thr Ala Val Tyr Tyr
                85                  90                  95

Cys Ala Arg

<210> SEQ ID NO 124
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60
```

```
Ser Val Lys Gly Arg Phe Thr Ile Ser Arg Asp Asp Ser Lys Asn Thr
 65                  70                  75                  80

Ala Tyr Leu Gln Met Asn Ser Leu Lys Thr Glu Asp Thr Ala Val Tyr
                 85                  90                  95

Tyr Cys Thr Arg
            100

<210> SEQ ID NO 125
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys

<210> SEQ ID NO 126
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Glu Val Gln Leu Val Glu Thr Gly Gly Gly Leu Ile Gln Pro Gly Gly
 1               5                  10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg

<210> SEQ ID NO 127
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 127

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg

<210> SEQ ID NO 128
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Glu Val Gln Leu Val Glu Ser Arg Gly Val Leu Val Gln Pro Gly Gly
1               5                   10                  15

Ser Leu Arg Leu Ser Cys Ala Ala Ser Gly Phe Thr Val Ser Ser Asn
            20                  25                  30

Glu Met Ser Trp Val Arg Gln Ala Pro Gly Lys Gly Leu Glu Trp Val
        35                  40                  45

Ser Ser Ile Ser Gly Gly Ser Thr Tyr Tyr Ala Asp Ser Arg Lys Gly
    50                  55                  60

Arg Phe Thr Ile Ser Arg Asp Asn Ser Lys Asn Thr Leu His Leu Gln
65                  70                  75                  80

Met Asn Ser Leu Arg Ala Glu Asp Thr Ala Val Tyr Tyr Cys Lys Lys
                85                  90                  95

<210> SEQ ID NO 129
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asn Ser Val
    50                  55                  60

Lys Gly Arg Phe Thr Ile Ser Arg Asp Asn Ser Lys Asn Thr Leu Tyr
65                  70                  75                  80

Leu Gln Met Gly Ser Leu Arg Ala Glu Asp Met Ala Val Tyr Tyr Cys
                85                  90                  95

Ala Arg

<210> SEQ ID NO 130
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 131
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 132
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr

```
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 133
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 134
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 135
```

```
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 136
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 137
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45
```

-continued

```
Ser Tyr Ile Ser Ser Ser Ser Thr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                 85                  90                  95

Ala Arg
```

<210> SEQ ID NO 138
<211> LENGTH: 97
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 138

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Asp Met His Trp Val Arg Gln Ala Thr Gly Lys Gly Leu Glu Trp Val
             35                  40                  45

Ser Ala Ile Gly Thr Ala Gly Asp Thr Tyr Tyr Pro Gly Ser Val Lys
 50                  55                  60

Gly Arg Phe Thr Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Ala
                 85                  90                  95

Arg
```

<210> SEQ ID NO 139
<211> LENGTH: 98
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 139

```
Glu Val Gln Leu Val Glu Ser Gly Gly Gly Leu Val Gln Pro Gly Gly
 1               5                  10                  15

Ser Leu Arg Leu Ser Cys Ala Ser Gly Phe Thr Phe Ser Ser Tyr
                 20                  25                  30

Trp Met His Trp Val Arg Gln Ala Pro Gly Lys Gly Leu Val Trp Val
             35                  40                  45

Ser Arg Ile Asn Ser Asp Gly Ser Ser Thr Ser Tyr Ala Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg
```

<210> SEQ ID NO 140
<211> LENGTH: 97
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 140

Ser Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Gly Ile Arg Asn
            20                  25                  30

Tyr Leu Ala Trp Tyr Gln Gln Lys Pro Gly Lys Ala Pro Lys Leu Leu
        35                  40                  45

Ile Tyr Ala Ala Ser Thr Leu Gln Ser Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Gln Arg Tyr Asn Arg Ala Pro
                85                  90                  95

Tyr

<210> SEQ ID NO 141
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro
                85                  90                  95

<210> SEQ ID NO 142
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro

```
<210> SEQ ID NO 143
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro
                85                  90                  95

<210> SEQ ID NO 144
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Ala Ile Arg Met Thr Gln Ser Pro Phe Ser Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Gln Lys Pro Ala Lys Ala Pro Lys Leu Phe Ile
        35                  40                  45

Tyr Tyr Ala Ser Ser Leu Gln Ser Gly Val Pro Ser Arg Phe Ser Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Tyr Tyr Ser Thr Pro
                85                  90

<210> SEQ ID NO 145
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Val Ile Trp Met Thr Gln Ser Pro Ser Leu Leu Ser Ala Ser Thr Gly
1               5                   10                  15

Asp Arg Val Thr Ile Ser Cys Arg Met Ser Gln Gly Ile Ser Ser Tyr
            20                  25                  30

Leu Ala Trp Tyr Gln Gln Lys Pro Gly Lys Ala Pro Glu Leu Leu Ile
        35                  40                  45
```

```
Tyr Ala Ala Ser Thr Leu Gln Ser Gly Val Pro Ser Arg Phe Ser Gly
        50                   55                   60

Ser Gly Ser Gly Thr Asp Phe Thr Leu Thr Ile Ser Cys Leu Gln Ser
65                   70                   75                   80

Glu Asp Phe Ala Thr Tyr Tyr Cys Gln Gln Tyr Tyr Ser Phe Pro
                85                   90                   95

<210> SEQ ID NO 146
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Ala Ile Arg Met Thr Gln Ser Pro Ser Ser Phe Ser Ala Ser Thr Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
        50                   55                   60

Ser Gly Ser Gly Thr Asp Phe Thr Leu Thr Ile Ser Cys Leu Gln Ser
65                   70                   75                   80

Glu Asp Phe Ala Thr Tyr Tyr Cys Gln Gln Tyr Tyr Ser Tyr Pro
                85                   90                   95

<210> SEQ ID NO 147
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
        50                   55                   60

Ser Gly Ser Gly Thr Asp Phe Leu Thr Ile Ser Ser Leu Gln Pro Glu
65                   70                   75                   80

Asp Phe Ala Thr Tyr Tyr Cys Gln Gln Ser Tyr Ser Thr Pro
                85                   90

<210> SEQ ID NO 148
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 149
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser
                85                  90                  95

<210> SEQ ID NO 150
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Glu
65                  70                  75                  80

Asp Phe Ala Thr Tyr Tyr Cys Gln Gln Phe Asn Ser Tyr Pro
                85                  90

<210> SEQ ID NO 151
<211> LENGTH: 95
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 151

Ala Ile Gln Leu Thr Gln Ser Pro Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro
                85                  90                  95

<210> SEQ ID NO 152
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro
                85                  90                  95

<210> SEQ ID NO 153
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Leu Gln His Asn Ser Tyr Pro
                85                  90

<210> SEQ ID NO 154
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

```
Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro
                85                  90                  95
```

<210> SEQ ID NO 155
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

```
Asn Ile Gln Met Thr Gln Ser Pro Ser Ala Met Ser Ala Ser Val Gly
1               5                   10                  15

Asp Arg Val Thr Ile Thr Cys Arg Ala Arg Gln Gly Ile Ser Asn Tyr
            20                  25                  30

Leu Ala Trp Phe Gln Gln Lys Pro Gly Lys Val Pro Lys His Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro
                85                  90                  95
```

<210> SEQ ID NO 156
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
```

```
                    50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro
                 85                  90                  95

<210> SEQ ID NO 157
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Trp
                20                  25                  30

Leu Ala Trp Tyr Gln Gln Lys Pro Glu Lys Ala Pro Lys Ser Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro
                 85                  90                  95

<210> SEQ ID NO 158
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro
                 85                  90                  95

<210> SEQ ID NO 159
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Asp Ile Gln Met Thr Gln Ser Pro Ser Ser Val Ser Ala Ser Val Gly
 1               5                  10                  15
```

```
Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Gly Val Pro Ser Arg Phe Ser Gly Ser Gly Ser Gly Thr Asp Phe
50                      55                  60

Thr Leu Thr Ile Ser Ser Leu Gln Pro Glu Asp Phe Ala Thr Tyr Tyr
65                  70                  75                  80

Cys Gln Gln Ala Asn Ser Phe Pro
                85

<210> SEQ ID NO 160
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Arg Asn Tyr Leu Ala Trp Tyr Leu Leu Ile Tyr Ala Ala Ser Thr Leu
1               5                   10                  15

Gln Gln Arg Tyr Asn Arg Ala Pro Tyr
            20                  25

<210> SEQ ID NO 161
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Asp Asp Tyr Ala Met His Trp Val Ser Ala Ile Thr Trp Asn Ser Gly
1               5                   10                  15

His Ile Asp

<210> SEQ ID NO 162
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Ala Lys Val Ser Tyr Leu Ser Thr Ala Ser Ser Leu Asp
1               5                   10

<210> SEQ ID NO 163
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
```

```
                35                  40                  45
Ile Tyr Arg Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Ser Gly

<210> SEQ ID NO 164
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

His Ser Leu Gly Ser Arg Arg Thr Leu Met Leu Leu Ala Gln
 1               5                  10

<210> SEQ ID NO 165
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

His Ser Leu Gly His Arg Arg Thr Met Met Leu Leu Ala Gln
 1               5                  10

<210> SEQ ID NO 166
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

His Ser Leu Ser Asn Arg Arg Thr Leu Met Ile Met Ala Gln
 1               5                  10

<210> SEQ ID NO 167
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

His Ser Leu Gly Asn Arg Arg Ala Leu Ile Leu Leu Ala Gln
 1               5                  10

<210> SEQ ID NO 168
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168
```

```
His Ser Leu Asn Asn Arg Arg Thr Leu Met Leu Met Ala Gln
1               5                   10
```

<210> SEQ ID NO 169
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

```
His Ser Leu Gly Asn Arg Arg Ala Leu Ile Leu Leu Gly Gln
1               5                   10
```

<210> SEQ ID NO 170
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

```
His Ser Leu Arg Asn Arg Arg Ala Leu Ile Leu Leu Ala Gln
1               5                   10
```

<210> SEQ ID NO 171
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

```
His Ser Leu Gly Asn Arg Arg Ala Leu Ile Leu Leu Ala Gln
1               5                   10
```

<210> SEQ ID NO 172
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
cttvrtmatc gtcgtrctmt g                                        21

<210> SEQ ID NO 173
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
cttratmatc gtcgtrctmt g                                        21

<210> SEQ ID NO 174
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 174
cttvgtmatc gtcgtrctmt g                                      21

<210> SEQ ID NO 175
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: a, c, g or t
<220> FEATURE:
<221> NAME/KEY: modified_base
<222> LOCATION: (11)..(11)
<223> OTHER INFORMATION: a, c, g or t
<220> FEATURE:
<221> NAME/KEY: modified_base
<222> LOCATION: (14)..(14)
<223> OTHER INFORMATION: a, c, g or t
<220> FEATURE:
<221> NAME/KEY: modified_base
<222> LOCATION: (17)..(17)
<223> OTHER INFORMATION: a, c, g or t
<220> FEATURE:
<221> NAME/KEY: modified_base
<222> LOCATION: (20)..(20)
<223> OTHER INFORMATION: a, c, g or t
<220> FEATURE:
<221> NAME/KEY: modified_base
<222> LOCATION: (23)..(23)
<223> OTHER INFORMATION: a, c, g or t
<220> FEATURE:
<221> NAME/KEY: modified_base
<222> LOCATION: (26)..(26)
<223> OTHER INFORMATION: a, c, g or t

<400> SEQUENCE: 175
gctcgtbnkb nkbnkbnkbn kbnkbnkwtk gat                         33

<210> SEQ ID NO 176
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: a, c, g or t
<220> FEATURE:
<221> NAME/KEY: modified_base
<222> LOCATION: (11)..(11)
<223> OTHER INFORMATION: a, c, g or t
<220> FEATURE:
<221> NAME/KEY: modified_base
<222> LOCATION: (14)..(14)
<223> OTHER INFORMATION: a, c, g or t
<220> FEATURE:
<221> NAME/KEY: modified_base
<222> LOCATION: (17)..(17)
<223> OTHER INFORMATION: a, c, g or t
<220> FEATURE:
<221> NAME/KEY: modified_base
<222> LOCATION: (20)..(20)
<223> OTHER INFORMATION: a, c, g or t
<220> FEATURE:
<221> NAME/KEY: modified_base
<222> LOCATION: (23)..(23)
<223> OTHER INFORMATION: a, c, g or t
<220> FEATURE:
<221> NAME/KEY: modified_base
<222> LOCATION: (26)..(26)
```

```
<223> OTHER INFORMATION: a, c, g or t

<400> SEQUENCE: 176
gctcgtbnbb nbbnbbnbbn bbnbbnbwtk gat                              33
```